US010611825B2

(12) United States Patent
Bossenmaier et al.

(10) Patent No.: US 10,611,825 B2
(45) Date of Patent: Apr. 7, 2020

(54) MONOVALENT ANTIGEN BINDING PROTEINS

(71) Applicant: Hoffmann-La Roche Inc., Little Falls, NJ (US)

(72) Inventors: Birgit Bossenmaier, Seefeld (DE); Hubert Kettenberger, Munich (DE); Christian Klein, Bonstetten (CH); Klaus-Peter Kuenkele, Benediktbeuern (DE); Joerg Thomas Regula, Munich (DE); Wolfgang Schaefer, Mannheim (DE); Manfred Schwaiger, Wang-Bergen (DE); Claudio Sustmann, Munich (DE)

(73) Assignee: HOFFMANN LA-ROCHE INC., Little Falls, NJ (US)

( * ) Notice: Subject to any disclaimer, the term of this patent is extended or adjusted under 35 U.S.C. 154(b) by 21 days.

(21) Appl. No.: 15/620,456

(22) Filed: Jun. 12, 2017

(65) Prior Publication Data

US 2018/0037633 A1 Feb. 8, 2018

Related U.S. Application Data

(62) Division of application No. 13/406,503, filed on Feb. 27, 2012, now abandoned.

(30) Foreign Application Priority Data

Feb. 28, 2011 (EP) .................................... 11156321

(51) Int. Cl.
*C07K 16/00* (2006.01)
*C07K 16/28* (2006.01)

(52) U.S. Cl.
CPC .......... *C07K 16/00* (2013.01); *C07K 16/2863* (2013.01); *C07K 2317/35* (2013.01); *C07K 2317/64* (2013.01); *C07K 2317/66* (2013.01); *C07K 2317/732* (2013.01); *C07K 2317/76* (2013.01); *C07K 2317/77* (2013.01); *C07K 2317/92* (2013.01); *C07K 2317/94* (2013.01)

(58) Field of Classification Search
CPC ............ C07K 2317/35; C07K 2317/66; C07K 2317/30; C07K 16/00–468
See application file for complete search history.

(56) References Cited

U.S. PATENT DOCUMENTS

| | | |
|---|---|---|
| 4,150,149 A | 4/1979 | Wolfsen et al. |
| 4,361,544 A | 11/1982 | Goldberg |
| 4,444,744 A | 4/1984 | Goldberg |
| 4,737,456 A | 4/1988 | Weng et al. |
| 4,816,567 A | 3/1989 | Cabilly et al. |
| 5,202,238 A | 4/1993 | Fell, Jr. et al. |
| 5,204,244 A | 4/1993 | Fell et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,648,237 A | 7/1997 | Carter |
| 5,648,260 A | 7/1997 | Winter et al. |
| 5,677,425 A | 10/1997 | Bodmer et al. |
| 5,731,168 A | 3/1998 | Carter et al. |
| 5,747,654 A | 5/1998 | Pastan et al. |
| 5,789,199 A | 8/1998 | Joly et al. |
| 5,798,229 A | 8/1998 | Strittmatter et al. |
| 5,821,333 A | 10/1998 | Carter et al. |
| 5,821,337 A | 10/1998 | Carter et al. |
| 5,840,523 A | 11/1998 | Simmons et al. |
| 5,869,046 A | 2/1999 | Presta et al. |
| 5,959,083 A | 9/1999 | Bosslet et al. |
| 5,959,177 A | 9/1999 | Hein et al. |
| 6,040,498 A | 3/2000 | Stomp et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vézina et al. |
| 6,511,663 B1 | 1/2003 | King et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,737,056 B1 | 5/2004 | Presta |
| 6,897,044 B1 | 5/2005 | Braslawsky et al. |
| 6,946,292 B2 | 9/2005 | Kanda et al. |
| 6,982,321 B2 | 1/2006 | Winter |
| 7,125,978 B1 | 10/2006 | Vézina et al. |
| 7,129,330 B1 | 10/2006 | Little et al. |
| 7,183,076 B2 | 2/2007 | Arathoon et al. |
| 7,276,585 B2 | 10/2007 | Lazar et al. |
| 7,317,091 B2 | 1/2008 | Lazar et al. |
| 7,332,581 B2 | 2/2008 | Presta |
| 7,355,008 B2 | 4/2008 | Stavenhagen et al. |
| 7,371,826 B2 | 5/2008 | Presta |
| 7,381,408 B2 | 6/2008 | Mezo et al. |
| 7,504,256 B1 | 3/2009 | Ogawa et al. |
| 7,521,541 B2 | 4/2009 | Eigenbrot et al. |

(Continued)

FOREIGN PATENT DOCUMENTS

| | | |
|---|---|---|
| CA | 2853230 A1 | 5/2013 |
| CN | 1173878 A | 2/1998 |

(Continued)

OTHER PUBLICATIONS

Aggarwal et al. (Jan. 22, 2008). "Fibroblast Activation Protein Peptide Substrates Identified from Human Collagen I Derived Gelatin Cleavage Sites," *Biochemistry* 47(3):1076-1086.

(Continued)

*Primary Examiner* — Jessica H Roark
(74) *Attorney, Agent, or Firm* — Morrison & Foerster LLP

(57) ABSTRACT

The present invention relates to monovalent antigen binding proteins with a CH1-CL domain exchange, methods for their production, pharmaceutical compositions containing said antibodies, and uses thereof.

8 Claims, 20 Drawing Sheets

Specification includes a Sequence Listing.

(56) References Cited

U.S. PATENT DOCUMENTS

| | | |
|---|---|---|
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 7,951,917 B1 | 5/2011 | Arathoon et al. |
| 8,188,231 B2 | 5/2012 | Lazar et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtula et al. |
| 8,313,913 B2 | 11/2012 | Nakamura et al. |
| 8,642,745 B2 | 2/2014 | Arathoon et al. |
| 8,765,412 B2 | 7/2014 | Matsumoto |
| 8,796,424 B2 | 8/2014 | Croasdale et al. |
| 8,945,552 B2 | 2/2015 | Baehner et al. |
| 9,150,639 B2 | 10/2015 | Yamasaki et al. |
| 9,241,994 B2 | 1/2016 | Igawa |
| 9,308,259 B2 | 4/2016 | Epshtein et al. |
| 9,605,084 B2 | 3/2017 | Moore et al. |
| 9,890,204 B2 | 2/2018 | Brinkman et al. |
| 9,982,036 B2 | 5/2018 | Bossenmaier et al. |
| 10,138,293 B2 | 11/2018 | Klein et al. |
| 10,323,099 B2 | 6/2019 | Bruenker |
| 2002/0062010 A1 | 5/2002 | Arathoon et al. |
| 2002/0155537 A1 | 10/2002 | Carter et al. |
| 2002/0164328 A1 | 11/2002 | Shinkawa et al. |
| 2003/0099974 A1 | 5/2003 | Lillie et al. |
| 2003/0115614 A1 | 6/2003 | Kanda et al. |
| 2003/0124129 A1 | 7/2003 | Oliner |
| 2003/0157108 A1 | 8/2003 | Presta |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0073013 A1 | 4/2004 | Fukushima et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0214988 A1 | 10/2004 | Tirrell et al. |
| 2004/0220388 A1 | 11/2004 | Metens et al. |
| 2004/0259075 A1 | 12/2004 | Dimitrove et al. |
| 2004/0259150 A1 | 12/2004 | Nakamura et al. |
| 2005/0014934 A1 | 1/2005 | Hinton et al. |
| 2005/0031613 A1 | 2/2005 | Nakamura et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0123476 A1 | 6/2005 | Bugge et al. |
| 2005/0123546 A1 | 6/2005 | Umana et al. |
| 2005/0152894 A1 | 7/2005 | Krummen et al. |
| 2005/0163782 A1 | 7/2005 | Glaser et al. |
| 2005/0249722 A1 | 11/2005 | Beliard et al. |
| 2005/0260186 A1 | 11/2005 | Bookbinder et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0071675 A1 | 3/2007 | Wu et al. |
| 2007/0071742 A1 | 3/2007 | Fang et al. |
| 2007/0092940 A1 | 4/2007 | Eigenbrot et al. |
| 2007/0134759 A1 | 6/2007 | Nishiya et al. |
| 2007/0141065 A1 | 6/2007 | Fuh et al. |
| 2007/0166305 A1 | 7/2007 | Hanai et al. |
| 2007/0269369 A1 | 11/2007 | Gegg et al. |
| 2007/0274985 A1 | 11/2007 | Dubel et al. |
| 2007/0274998 A1 | 11/2007 | Uktu |
| 2007/0287170 A1 | 12/2007 | Davis et al. |
| 2008/0063641 A1 | 3/2008 | Huang et al. |
| 2008/0187954 A1 | 8/2008 | Kallmeier et al. |
| 2008/0234183 A1 | 9/2008 | Hallbrink et al. |
| 2008/0241884 A1 | 10/2008 | Shitara et al. |
| 2009/0023811 A1 | 1/2009 | Biadatti et al. |
| 2009/0060910 A1 | 3/2009 | Johnson |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0203078 A1 | 8/2009 | Ogawa et al. |
| 2009/0194692 A1 | 9/2009 | Kobaru |
| 2009/0232811 A1 | 9/2009 | Klein et al. |
| 2009/0304715 A1 | 12/2009 | Masuho |
| 2010/0015133 A1 | 1/2010 | Igawa et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256339 A1 | 10/2010 | Bossenmaier |
| 2010/0256340 A1 | 10/2010 | Brinkmann et al. |
| 2010/0286374 A1 | 11/2010 | Kannan et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0149879 A1 | 6/2012 | Brinkmann et al. |
| 2012/0164726 A1 | 6/2012 | Klein et al. |
| 2012/0177637 A1 | 7/2012 | Hoogenboom et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2013/0022601 A1 | 1/2013 | Brinkmann et al. |
| 2013/0045492 A1 | 2/2013 | Babb et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0112914 A1 | 4/2014 | Nezu et al. |
| 2014/0154254 A1 | 6/2014 | Kannan et al. |
| 2014/0199294 A1 | 7/2014 | Mimoto et al. |
| 2014/0249296 A1 | 9/2014 | Ploegh |
| 2014/0294810 A1 | 10/2014 | Lowman et al. |
| 2014/0322756 A1 | 10/2014 | Arathoon et al. |
| 2014/0370019 A1 | 12/2014 | Bruenker et al. |
| 2014/0370020 A1 | 12/2014 | Kuramochi et al. |
| 2015/0166670 A1 | 6/2015 | Castoldi et al. |
| 2015/0274845 A1 | 10/2015 | Bruenker et al. |
| 2015/0291704 A1 | 10/2015 | Beck |
| 2015/0315296 A1 | 11/2015 | Schaefer et al. |
| 2015/0344570 A1 | 12/2015 | Igawa et al. |
| 2016/0168259 A1 | 1/2016 | Igawa |
| 2016/0039937 A1 | 2/2016 | Yamasaki et al. |
| 2016/0075785 A1 | 3/2016 | Ast et al. |
| 2016/0238600 A1 | 4/2016 | Hoogenboom et al. |
| 2016/0130347 A1 | 5/2016 | Bruenker et al. |
| 2016/0208019 A1 | 7/2016 | Bacac et al. |
| 2016/0222132 A1 | 8/2016 | Keyt et al. |
| 2016/0319036 A1 | 11/2016 | Bruenker |
| 2017/0029529 A1 | 2/2017 | Croasdale et al. |
| 2017/0037121 A1 | 2/2017 | Schlothauer |
| 2017/0037153 A1 | 2/2017 | Skolaut et al. |
| 2017/0044246 A1 | 2/2017 | Schlothauer |
| 2017/0096485 A1 | 4/2017 | Bacac et al. |
| 2017/0096495 A1 | 4/2017 | Bacac et al. |
| 2017/0114135 A1 | 4/2017 | Codarri-Deak et al. |
| 2017/0114141 A1 | 4/2017 | Amann et al. |
| 2017/0114146 A1 | 4/2017 | Klein et al. |
| 2017/0129962 A1 | 5/2017 | Regula et al. |
| 2017/0145116 A1 | 5/2017 | Regula et al. |
| 2017/0174786 A1 | 6/2017 | Bacac et al. |
| 2017/0190783 A1 | 7/2017 | Bacac et al. |
| 2017/0247467 A1 | 8/2017 | Amann et al. |
| 2017/0253670 A1 | 9/2017 | Klein et al. |
| 2017/0306018 A1 | 10/2017 | Vu et al. |

(56) References Cited

U.S. PATENT DOCUMENTS

| | | |
|---|---|---|
| 2017/0306036 A1 | 10/2017 | Vu et al. |
| 2017/0349669 A1 | 12/2017 | Sabine et al. |
| 2018/0312573 A1 | 11/2018 | Bossenmaier et al. |
| 2019/0153071 A1 | 5/2019 | Klein |

FOREIGN PATENT DOCUMENTS

| | | | |
|---|---|---|---|
| CN | 1176659 | A | 3/1998 |
| CN | 1232039 | A | 10/1999 |
| CN | 1603345 | A | 4/2005 |
| CN | 101065151 | A | 10/2007 |
| CN | 101205255 | A | 6/2008 |
| CN | 101218251 | A | 7/2008 |
| CN | 101355966 | A | 1/2009 |
| EP | 0 307 434 | B1 | 3/1989 |
| EP | 0 637 593 | A1 | 2/1995 |
| EP | 1 331 266 | A1 | 7/2003 |
| EP | 1 870 458 | A1 | 12/2007 |
| EP | 1 870 459 | A1 | 12/2007 |
| EP | 1 925 319 | A1 | 5/2008 |
| EP | 2 050 764 | A1 | 4/2009 |
| EP | 2 443 154 | B1 | 4/2012 |
| EP | 2 554 669 | A1 | 2/2013 |
| EP | 2 647 707 | A1 | 10/2013 |
| EP | 2 728 002 | A1 | 5/2014 |
| EP | 2 787 078 | A1 | 10/2014 |
| EP | 2 940 135 | A1 | 11/2015 |
| JP | 2008-531049 | A | 8/2008 |
| JP | 2011-506510 | A | 3/2011 |
| JP | 2012-525149 | A | 10/2012 |
| JP | 2013-539461 | A | 10/2013 |
| JP | 2015-502373 | A | 1/2015 |
| RU | 2005/124281 | A | 1/2006 |
| RU | 2295537 | C2 | 3/2007 |
| WO | 0 307 434 | B2 | 3/1989 |
| WO | WO-1993/01161 | A1 | 1/1993 |
| WO | WO-93/06217 | A1 | 4/1993 |
| WO | WO-1993/10819 | A1 | 6/1993 |
| WO | WO-1993/16185 | A2 | 8/1993 |
| WO | WO-1993/16185 | A3 | 8/1993 |
| WO | WO-94/09131 | A1 | 4/1994 |
| WO | WO-94/10202 | A1 | 5/1994 |
| WO | WO-94/29350 | A2 | 12/1994 |
| WO | WO-94/29350 | A3 | 12/1994 |
| WO | WO-1994/29351 | A2 | 12/1994 |
| WO | WO-1994/29351 | A3 | 12/1994 |
| WO | WO-95/09917 | A1 | 4/1995 |
| WO | WO-96/27011 | A1 | 9/1996 |
| WO | WO-96/27612 | A1 | 9/1996 |
| WO | WO-97/01580 | A1 | 1/1997 |
| WO | WO-97/014719 | A1 | 4/1997 |
| WO | WO-97/028267 | A1 | 8/1997 |
| WO | WO-97/028267 | C1 | 8/1997 |
| WO | WO-1997/30087 | A1 | 8/1997 |
| WO | WO-1998/10431 | A2 | 3/1998 |
| WO | WO-1998/10431 | C1 | 3/1998 |
| WO | WO-98/45331 | A2 | 10/1998 |
| WO | WO-98/45331 | A3 | 10/1998 |
| WO | WO-98/45332 | A2 | 10/1998 |
| WO | WO-98/45332 | A3 | 10/1998 |
| WO | WO-1998/48032 | A2 | 10/1998 |
| WO | WO-1998/48032 | A3 | 10/1998 |
| WO | WO-98/50431 | A2 | 11/1998 |
| WO | WO-1998/58964 | A1 | 12/1998 |
| WO | WO-1999/22764 | A1 | 5/1999 |
| WO | WO-99/37791 | A1 | 7/1999 |
| WO | WO-1999/37791 | A1 | 7/1999 |
| WO | WO-99/54342 | A1 | 10/1999 |
| WO | WO-1999/51642 | A1 | 10/1999 |
| WO | WO-99/66951 | A2 | 12/1999 |
| WO | WO-99/66951 | A3 | 12/1999 |
| WO | WO-99/66951 | C1 | 12/1999 |
| WO | WO-00/05265 | A2 | 2/2000 |
| WO | WO-00/35956 | A1 | 6/2000 |
| WO | WO-00/61739 | A1 | 10/2000 |
| WO | WO-2001/29246 | A1 | 4/2001 |
| WO | WO-01/77342 | A1 | 10/2001 |
| WO | WO-01/90192 | A2 | 11/2001 |
| WO | WO-2001/085795 | A1 | 11/2001 |
| WO | WO-02/02781 | A1 | 1/2002 |
| WO | WO-02/33073 | A1 | 4/2002 |
| WO | WO-2002/31140 | A1 | 4/2002 |
| WO | WO-02/096948 | A2 | 12/2002 |
| WO | WO-2003/011878 | A2 | 2/2003 |
| WO | WO-2003/011878 | A3 | 2/2003 |
| WO | WO-03/030833 | A2 | 4/2003 |
| WO | WO-03/030833 | A3 | 4/2003 |
| WO | WO-03/035835 | A2 | 5/2003 |
| WO | WO-03/035835 | A3 | 5/2003 |
| WO | WO-03/055993 | A1 | 7/2003 |
| WO | WO-03/057134 | A2 | 7/2003 |
| WO | WO-2003/073238 | A2 | 9/2003 |
| WO | WO-2003/073238 | A3 | 9/2003 |
| WO | WO-2003/084570 | A1 | 10/2003 |
| WO | WO-2003/085107 | A1 | 10/2003 |
| WO | WO-2003/085119 | A1 | 10/2003 |
| WO | WO-03/097105 | A1 | 11/2003 |
| WO | WO-03/106501 | A1 | 12/2003 |
| WO | WO-2004/003019 | A2 | 1/2004 |
| WO | WO-2004/003019 | A3 | 1/2004 |
| WO | WO-2004/032961 | A1 | 4/2004 |
| WO | WO-2004/056312 | A2 | 7/2004 |
| WO | WO-2004/056312 | A3 | 7/2004 |
| WO | WO-2004/058298 | A2 | 7/2004 |
| WO | WO-2004/065540 | A2 | 8/2004 |
| WO | WO-2004/065540 | A3 | 8/2004 |
| WO | WO-2004/072117 | A2 | 8/2004 |
| WO | WO-2004/072117 | A3 | 8/2004 |
| WO | WO-2004/106375 | A1 | 12/2004 |
| WO | WO-2005/000900 | A1 | 1/2005 |
| WO | WO-2005/001025 | A2 | 1/2005 |
| WO | WO-2005/001025 | A3 | 1/2005 |
| WO | WO-2005/004809 | A2 | 1/2005 |
| WO | WO-2005/004809 | A3 | 1/2005 |
| WO | WO-2005/005635 | A2 | 1/2005 |
| WO | WO-2005/005635 | A3 | 1/2005 |
| WO | WO-2005/011735 | A1 | 2/2005 |
| WO | WO-2005/018572 | A2 | 3/2005 |
| WO | WO-2005/018572 | A3 | 3/2005 |
| WO | WO-2005/027966 | A2 | 3/2005 |
| WO | WO-2005/027966 | A3 | 3/2005 |
| WO | WO-2005/033778 | A2 | 4/2005 |
| WO | WO-2005/033778 | A3 | 4/2005 |
| WO | WO-2005/035586 | A1 | 4/2005 |
| WO | WO-2005/035727 | A2 | 4/2005 |
| WO | WO-2005/035727 | A3 | 4/2005 |
| WO | WO-2005/035778 | A1 | 4/2005 |
| WO | WO-2005/044853 | A2 | 5/2005 |
| WO | WO-2005/044853 | A3 | 5/2005 |
| WO | WO-2005/044859 | A2 | 5/2005 |
| WO | WO-2005/044859 | A3 | 5/2005 |
| WO | WO-2005/051422 | A1 | 6/2005 |
| WO | WO-2005/051976 | A2 | 6/2005 |
| WO | WO-2005/051976 | A3 | 6/2005 |
| WO | WO-2005/053742 | A1 | 6/2005 |
| WO | WO-2005/063816 | A2 | 7/2005 |
| WO | WO-2005/063816 | A3 | 7/2005 |
| WO | WO-2005/074524 | A2 | 8/2005 |
| WO | WO-2005/074524 | A3 | 8/2005 |
| WO | WO-2005/092925 | A2 | 10/2005 |
| WO | WO-2005/092925 | A3 | 10/2005 |
| WO | WO-2005/100402 | A1 | 10/2005 |
| WO | WO-2006/020258 | A2 | 2/2006 |
| WO | WO-2006/020258 | A3 | 2/2006 |
| WO | WO-2006/029879 | A2 | 3/2006 |
| WO | WO-2006/029879 | A3 | 3/2006 |
| WO | WO-2006/031370 | A2 | 3/2006 |
| WO | WO-2006/031370 | A3 | 3/2006 |
| WO | WO-2006/034488 | A2 | 3/2006 |
| WO | WO-2006/034488 | A3 | 3/2006 |
| WO | WO-2006/044908 | A2 | 4/2006 |
| WO | WO-2006/044908 | A3 | 4/2006 |
| WO | WO-2006/045049 | A1 | 4/2006 |
| WO | WO-2006/068953 | A2 | 6/2006 |

(56) References Cited

FOREIGN PATENT DOCUMENTS

| | | |
|---|---|---|
| WO | WO-2006/068953 A3 | 6/2006 |
| WO | WO-2006/082515 A2 | 8/2006 |
| WO | WO-2006/082515 A3 | 8/2006 |
| WO | WO-2006/091209 A2 | 8/2006 |
| WO | WO-2006/091209 A3 | 8/2006 |
| WO | WO-2006/093794 A1 | 8/2006 |
| WO | WO-2006/103100 A2 | 10/2006 |
| WO | WO-2006/103100 A3 | 10/2006 |
| WO | WO-2006/106905 A1 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2006/132352 A1 | 12/2006 |
| WO | WO-2007/024715 A2 | 3/2007 |
| WO | WO-2007/031875 A2 | 3/2007 |
| WO | WO-2007/031875 A3 | 3/2007 |
| WO | WO-2007/044323 A2 | 4/2007 |
| WO | WO-2007/044323 A3 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/146959 A2 | 12/2007 |
| WO | WO-2007/146959 A3 | 12/2007 |
| WO | WO-2007/147901 A1 | 12/2007 |
| WO | WO-2007/149010 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/022349 A2 | 2/2008 |
| WO | WO-2008/027236 A2 | 3/2008 |
| WO | WO-2008/027236 A3 | 3/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2009/126944 A1 | 10/2009 |
| WO | WO2010006060 A2 | 1/2010 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO2010006060 A3 | 6/2010 |
| WO | WO-2010/084197 A1 | 7/2010 |
| WO | WO-2010/087994 A2 | 8/2010 |
| WO | WO-2010/087994 A3 | 8/2010 |
| WO | WO-2010/108127 A1 | 9/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/097603 A1 | 8/2011 |
| WO | WO-2011/118739 A1 | 9/2011 |
| WO | WO-2011/143545 A1 | 11/2011 |
| WO | WO-2012/023053 A2 | 2/2012 |
| WO | WO-2012/023053 A3 | 2/2012 |
| WO | WO-2012/025525 A1 | 3/2012 |
| WO | WO-2012/025530 A1 | 3/2012 |
| WO | WO2012045671 A1 | 4/2012 |
| WO | WO-2012/058768 A1 | 5/2012 |
| WO | WO-2012/073985 A1 | 6/2012 |
| WO | WO-2012/075037 A1 | 6/2012 |
| WO | WO-2012/116927 A1 | 9/2012 |
| WO | WO-2012/131555 A2 | 10/2012 |
| WO | WO-2012/131555 A3 | 10/2012 |
| WO | WO-2012/143379 A1 | 10/2012 |
| WO | WO-2012/148873 A2 | 11/2012 |
| WO | WO-2012/148873 A3 | 11/2012 |
| WO | WO-2012/148873 A4 | 11/2012 |
| WO | WO-2013/002362 A1 | 1/2013 |
| WO | WO-2013/003555 A1 | 1/2013 |
| WO | WO-2013/012733 A1 | 1/2013 |
| WO | WO-2013/026832 A1 | 2/2013 |
| WO | WO-2013/026833 A1 | 2/2013 |
| WO | WO-2013/026835 A1 | 2/2013 |
| WO | WO-2013/065708 A1 | 5/2013 |
| WO | WO-2013/092001 A1 | 6/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/150043 A1 | 10/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/012085 A2 | 1/2014 |
| WO | WO-2014/012085 A3 | 1/2014 |
| WO | WO-2014/049003 A1 | 4/2014 |
| WO | WO-2014/081955 A1 | 5/2014 |
| WO | WO-2014/082179 A1 | 6/2014 |
| WO | WO-2014/104165 A1 | 7/2014 |
| WO | WO-2014/144357 A1 | 9/2014 |
| WO | WO-2015/101588 A1 | 7/2015 |
| WO | WO-2016/016299 A1 | 2/2016 |
| WO | WO-2016/055432 A2 | 4/2016 |
| WO | WO-2016/055432 A3 | 4/2016 |
| WO | WO-2016/087416 A1 | 6/2016 |
| WO | WO-2017/055385 A1 | 4/2017 |
| WO | WO-2017/055392 A1 | 4/2017 |
| WO | WO-2017/055393 A1 | 4/2017 |

OTHER PUBLICATIONS

Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).

Anonymous. "Production in yeasts of stable antibody fragments," *Expert Opinion on Therapeutic Patents* 7(2):179-183, (1997).

(56) References Cited

OTHER PUBLICATIONS

Atwell et al. "Stable heterodimers from remodeling the domain interface of a homodimer using a phage display library," *J. Mol. Biol.* 270 (1):26-35 (1997).
Ausubel et al. *Short Protocols in Molecular Biology*, Greene Publishing and Wiley Interscience, New York, New York, (Table of Contents), (1987).
Avgeris et al. "Kallikrein-related peptidase genes as promising biomarkers for prognosis and monitoring of human malignancies," *Biol. Chem* 391(5):505-511, (May 2010).
Bao et al. "HER2-mediated upregulation of MMP-1 is involved in gastric cancer cell invasion," *Arch Biochem Biophys* 499(1-2):49-55, (Jul. 2010).
Barnes et al., "Advances in animal cell recombinant protein production: GS-NS0 expression system," *Cytotechnology* 32 (2):109-23 (Feb. 2000).
Barnes et al. "Characterization of the stability of recombinant protein production in the GS-NS0 expression system," *Biotechnol Bioeng.* 73(4):261-70 (May 2001).
Baserga et al. (2003). "The IGF-1 Receptor in Cancer Biology," *Int. J. Cancer* 107:873-877.
Beckman et al. "Antibody Constructs in Cancer Therapy. Protein Engineering Strategies to Improve Exposure in Solid Tumors," *Cancer* 109(2):170-179, (Jan. 15, 2007, e-pub. Dec. 11, 2006).
Berkman, R.A. et al. "Expression of the Vascular Permeability Factor/Vascular Endothelial Growth Factor Gene in Central Nervous System Neoplasms," *J. Clin. Invest.* 91:153-159, (Jan. 1993).
Bera et al. "A bivalent disulfide-stabilized Fv with improved antigen binding to erbB2," *J. Mol. Biol.* 281(3):475-483, (Aug. 21, 1998).
Bird et al. "Single-Chain Antigen-Binding Proteins," *Science* 242(4877):423-6, (Oct. 21, 1988).
Bird et al. "Single-Chain Antigen-Binding Proteins," *Science* 244(4903):409, *Erratum*, (Apr. 28, 1989).
Boado et al. "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).
Boerner et al. "Production of Antigen-Specific Human Monoclonal Antibodies From In Vitro-Primed Human Splenocytes," *J. Immunol.* 147(1):86-95, (Jul. 1991).
Borgström et al. "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Bostrom et al. (2009). "Variants of the Antibody Herceptin That Interact With HER2 and VEGF at the Antigen Binding Site," *Science* 323:1610-1614.
Briggs et al. "Cystatin E/M suppresses legumain activity and invasion of human melanoma," *BMC Cancer* 10(17):1-13, (Jan. 2010).
Brinkmann, U. "Disulfide-stabilized Fv fragments," Chapter 14 in *2 In Antibody Engineering*, Kontermaan et al. eds., vol. 2, Springer-Verlag, Berlin Heidelberg, Germany, pp. 181-189, (Apr. 30, 2010).
Brinkmann et al., "A Recombinant Immunotoxin Containing a Disulfide-Stabilized Fv Fragment," *PNAS* 90(16):7538-7542, (1993).
Brocks et al. "A TNF Receptor Antagonistic scFv, Which is Not Secreted in Mammalian Cells, is Expressed as a Soluble Mono- and Bivalent scFv Derivative in Insect Cells," *Immunotechnology* 3:173-184, (1997).
Brorson et al., "Mutational Analysis of Avidity and Fine Specificity of Anti-Levan Antibodies," *J. Immunol.* 163:6694-6701 (1994).
Brown, L.F. et al. "Expression of Vascular Permeability Factor (Vascular Endothelial Growth Factor) and its Receptors in Breast Cancer," *Human Pathol.* 26(1):86-91, (Jan. 1995).
Brown, L.F. et al. "Expression of Vascular Permeability Factor (Vascular Endothelial Growth Factor) and its Receptors in Adenocarcinomas of the Gastrointestinal Tract," *Cancer Res.* 53:4727-4735, (Oct. 1, 1993).
Brüggemann et al. "Comparison of the Effector Functions of Human Immunoglobulins Using a Matched Set of Chimeric Antibodies," *J Exp Med.* 166(5):1351-61, (Nov. 1987).
Brüggemann et al. "Designer Mice: The Production of Human Antibody Repertoires in Transgenic Animals," *Year in Immuno.* 7:33-40, (1993).
Brummell et al. "Probing the Combining Site of an Anti-Carbohydrate Antibody by Saturation-Mutagenesis: Role of the Heavy-Chain CDR3 Residues," *Biochemistry* 32(4):1180-1187 (1993).
Brunhouse et al. "Isotyes of IgG: comparison of the primary structures of three pairs of isotypes which differ in their ability to activate complement," *Mol Immunol.* 16(11):907-917 (Nov. 1979).
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.
Burgess et al. "Possible dissociation of the heparin-binding and mitogenic activities of heparin-binding (acidic fibroblast growth factor-1 from its receptor-binding activities by site-directed mutagenesis of a single lysine residue," *Journal of Cell Biology* 111:2129-2138, (Nov. 1990).
Burks et al. "In vitro scanning saturation mutagenesis of an antibody binding pocket," *PNAS* 94(2):412-417 (1997).
Burton et al. "The C1q Receptor Site on Immunoglobulin G," *Nature* 288(5789):338-344, (Nov. 27, 1980).
Caron et al., "Engineered Humanized Dimeric Forms of IgG Are More Effective Antibodies," *J. Exp. Med.* 176(4):1191-1195, (Oct. 1, 1992).
Carro et al. "Serum Insulin-Like Growth Factor I Regulates Brain Amyloid-βLevels," *Nature Medicine* 8(12):1390-1397, (2002, e-pub. Nov. 4, 2002).
Carter et al. "Humanization of an Anti-P185$^{HER2}$ Antibody for Human Cancer Therapy," *Proc Natl Acad Sci USA.* 89(10):4285-4289 (May 1992).
Carter., "Bispecific human IgG by design," *Immunol. Methods* 248:7-15, (2001).
Casset et al. "A peptide mimetic of an anti-CD4 monoclonal," *Biochem and Biophys Res Comm.* 307:198-205, (2003).
Castoldi et al. (2012). "Molecular Characterization of Novel Trispecific ErbB-cMet-IGF1R Antibodies and Their Antigen-Binding Properties," *Prot. Engin. Des. Selection* 25:551-560.
Céspedes et al. "Mouse Models in Oncogenesis and Cancer Therapy," *Clin. Transl. Oncol.* 8(5):318-329 (2006).
Chan, L.A. et al. "Variable Region Domain Exchange in Human IgGs Promotes Antibody Complex Formulation with Accompanying Structural Changes and Altered Effector Functions," *Molecular Immunology* 41(5):527-538. (2004).
Chernaia, V.I. "Cathepsin L From Human Brain Tumor. Purification and Contents," *Ukr Biokhim Zh.* 70(5):97-103, (Sep.-Oct. 1998). (English Translation of Abstract.) (Article in Russian).
Cheung, A.H. et al. "Endothelial Tie2/Tek Ligands Angiopoietin-1 (ANGPT1) and Angiopoietin-2 (ANGPT2): Regional Localization of the Human Genes to 8q22.3-q23 and 8p23," *Genomics* 48(3):389-391, (Mar. 15, 1998).
Chicheportiche, Y. et al. "TWEAK, a New Secreted Ligand in the Tumor Necrosis Factor Family That Weakly Induces Apoptosis," *J. Biol. Chem.* 272(51):32401-32410, (1997).
Chitnis, M.M. et al. "The Type 1 Insulin-Like Growth Factor Receptor Pathway," *Clin. Cancer Res.* 14(20):6364-6370, (Oct. 16, 2008).
Chung, D.-E. et al. "Development of a Novel Albumin-Binding Prodrug That is Cleaved by Urokinase-Type-Plasminogen Activator (uPA)," *Bioorg. Med. Chem. Lett.* 16(19):5157-5163, (Oct. 1, 2006).
Cohen, S.N. et al. "Nonchromosomal Antibiotic Resistance in Bacteria: Genetic Transformation of *Escherichia coli* by R-factor DNA," *Proc. Natl. Acad. Sci. USA* 69(8):2110-2114, (Aug. 1972).
Cole, S.P.C. et al. "The EBV-Hybridoma Technique and its Application to Human Lung Cancer," *Monoclonal Antibodies and Cancer Therapy*, New York: Alan R. Liss, Inc. pp. 77-96, (1985).
Coleman, P.M. "Effects of Amino Acid Sequence Changes on Antibody-Antigen Interactions," *Research in Immunol.* 145(1):33-38, (1994).

(56) References Cited

OTHER PUBLICATIONS

Coloma, M.J. et al. "Design and Production of Novel Tetravalent Bispecific Antibodies," *Nature Biotechnology* 15(2):159-163, (Feb. 1997).
Connolly, D.T. et al. "Human Vascular Permeability Factor," *J. Biol. Chem.* 264(33):20017-20024, (Nov. 25, 1989).
Cordingley, M.G. et al. "Substrate Requirements of Human Rhinovirus 3C Protease for Peptide Cleavage in Vitro," *J. Biol. Chem.* 265(16):9062-9065, (1990).
Cortesio, C.L. et al. (Mar. 10, 2008). "Calpain 2 and PTP1B Function in a Novel Pathway With Src to Regulate Invadopodia Dynamics and Breast Cancer Cell Invasion," *J. Cell Biol.* 180(5):957-971.
Coxon, A. et al. "Combined Treatment of Angiopoietin and VEGF Pathway Antagonists Enhances Antitumor Activity in Preclinical Models of Colon Carcinoma," *99th AACR Annual Meeting*, Abstract #1113, (Apr. 2008).
Crawford, H.C. et al. "Matrix Metalloproteinase-7 is Expressed by Pancreatic Cancer Precursors and Regulates Acinar-To-Ductal Metaplasia in Exocrine Pancreas," *J. Clin. Invest.* 109(11):1437-1444, (Jun. 2002).
Cudic, M. et al. "Extracellular Proteases as Targets for Drug Development," *Curr. Protein Pept. Sci.* 10(4):297-307, (Aug. 2009).
Cuesta, A.M. et al. "Multivalent Antibodies: When Design Surpasses Evolution," *Trends Biotech.* 28:355-362, (2010).
Cullen, S.P. et al. "Granzymes in Cancer and Immunity," *Cell Death Differ.* 17(4):616-623, (Apr. 2010).
Dall'Acqua, W. et al. "Contribution of Domain Interface Residues to the Stability of Antibody CH3 Domain Homodimers", *Biochemistry* 37:9266-9273, (1998).
Davies, J. et al. "Expression of GnTIII in a Recombinant Anti-CD20 CHO Production Cell Line: Expression of antibodies with Altered Glycoforms Leads To an Increase in ADCC Through Higher Affinity for FcγRIII," *Biotechnol. Bioeng.* 74:288-294, (2001).
Davis, J.H. et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
Dennis, C. "Off by a Whisker," *Nature* 442:739-741, (2006).
Deyev, S.M. "Multivalency: The Hallmark of Antibodies Used for Optimization of Tumor Targeting by Design," *Bioessays* 30(9):904-918, (2008).
Dimmock, N.J. et al. "Valency of Antibody Binding to Virions and its Determination by Surface Plasmon Resonance", *Rev. Med. Virol.*, 14:123-135, (2004).
Donaldson, J.M. et al. "Design and Development of Masked Therapeutic Antibodies to Limit Off-Target Effects: Application to Anti-EGFR Antibodies," *Cancer Biology & Therapy* 8(22):2145-2150, (Nov. 15, 2009).
Dufner, P. et al. "Harnessing Phage and Ribosome Display for Antibody Optimization," *Trends Biotechol.* 24(11):523-529, (2006).
Durocher, Y. et al. "High-level and High-Throughput Recombinant Protein Production by Transient Transfection of Suspension-Growing Human 293-EBNA1 Cells," *Nucleic Acids Research* 30(2 e9), (2002), 9 pages.
Dvorak, H. et al. "Vascular Permeability Factor/Vascular Endothelial Growth Factor, Microvascular Hyperpermeability, and Angiogenesis," *Am. J. Pathol.* 146(5):1029-1039, (May 1995).
Edelman, G.M. et al. "The Covalent Structure of an Entire γG Immunoglobulin Molecule," *Proc. Natl. Acad. Sci. USA* 63:78-85, (1969).
Fenn, S. et al. "Crystal Structure of an Anti-Ang2 CrossFab Demonstrates Complete Structural and Functional Integrity of the Variable Domain," PLOS ONE 8(4):e61953, (Apr. 1, 2013).
Ferrara, N. et al. "The Biology of Vascular Endothelial Growth Factor," *Endocr. Rev.* 18(1):4-25, (1997).
Fiedler, M. et al. "Purification and Characterisation of His-Tagged Antibody Fragments," Chapter 17 in *Antibody Engineering*, Kontermann and Dubel (Eds.), Springer Lab Manuals, pp. 243-256, (2001).
Fischer, N. et al. "Bispecific Antibodies: Molecules That Enable Novel Therapeutic Strategies," *Pathobiology* 74:3-14, (2007).
Flatman, S. et al. "Process Analytics for Purification of Monoclonal Antibodies," *J. Chromatogr B* 848:79-87, (2007).
Fujimori, K. et al. "A Modeling Analysis of Monoclonal Antibody Percolation Through Tumors: A Binding-Site Barrier," *J. Nuc. Med.* 31(7):1191-1198, (Jul. 1990).
Galamb, O. et al. "Inflammation, Adenoma and Cancer: Objective Classification of Colon Biopsy Specimens With Gene Expression Signature," *Dis. Markers* 25(1):1-16, (2008).
Geisse, S. et al. "Eukaryotic Expression Systems: A Comparison," *Protein Expression and Purification* 8:271-282, (1996).
Gerspach, J. et al. "Target-Selective Activation of a TNF Prodrug by Urokinase-Type Plasminogen Activator (uPA) Mediated Proteolytic Processing At the Cell Surface," *Cancer Immunol. Immunother* 55:1590-1600 (2006).
Gold, D.V. et al. "A Novel Bispecific, Trivalent Antibody Construct for Targeting Pancreatic Carcinoma," *Cancer Res.* 68(12):4819-4826, (2008).
Goldenberg, D. et al. "Bi-Specific Antibodies that Bind Specific Target Tissue and Targeted Conjugates," Derwent Information Ltd., 12 pages, (2012).
Graham, F.L. et al. "A New Technique for the Assay of Infectivity of Human Adenovirus 5 DNA," *Virology* 52 (2):456-467, (1973).
Greenwood, J. et al. "Structural Motifs Involved in Human IgG Antibody Effector Functions," *Eur. J. Immunology* 23(5):1098-1104, (May 1993).
Grote, M. et al. "Bispecific Antibody Derivatives Based on Full-Length IgG Formats," Chapter 16 in *Methods in Molecular Biology* 901:247-263, (2012).
Gunasekaran, K. et al. "Enhancing Antibody Fc Heterodimer Formation Through Electrostatic Steering Effects: Applications to Bispecific Molecules and Monovalent IgG," *The Journal of Biological Chemistry* 285(25):19637-19646, (Jun. 18, 2010, e-pub. Apr. 16, 2010).
Hartog, H. et al., "The Insulin-Like Growth Factor 1 Receptor in Cancer: Old focus, New Future," *European Journal of Cancer*, 43(13):1895-1904, (Aug. 23, 2007).
Hellings, P.W. et al. "Interleukin-17 Orchestrates the Granulocyte Influx Into Airways After Allergen Inhalation in a Mouse Model of Allergic Asthma" *Am. J. Respir. Cell Mol. Biol.* 28:42-50, (2003).
Henry, L.R. et al. "Clinical Implications of Fibroblast Activation Protein in Patients With Colon Cancer," *Clin. Cancer Res.* 13(6):1736-1741, (Mar. 15, 2007).
Hezareh, M. et al. "Effector Function Activities of a Panel of Mutants of a Broadly Neutralizing Antibody against Human Immunodeficiency Virus Type 1," *Journal of Virology* 75(24):12161-12168, (Dec. 2001).
Hollander, N. "Bispecific Antibodies for Cancer Therapy," *Immunotherapy* 1(2):211-222, (Mar. 2009).
Holliger, P. et al. "Engineered Antibody Fragments and the Rise of Single Domains," *Nat. Biotechnol.* 23(9):1126-1136, (Sep. 2005).
Hoogenboom, H.R. "By-Passing Immunisation: Human antibodies from synthetic repertoires of germline $V_H$ gene segments rearranged in vitro," *J Mol. Biol.* 227(2):381-388, (Sep. 20, 1992).
Hust, M. et al. "Single Chain Fab (scFab) Fragment," *BMC Biotechnology* 7(14):1-15, (Mar. 8, 2007).
Huston, J.S. et al. "Protein Engineering of Antibody Binding Sites: Recovery of Specific Activity in an Anti-Digoxin Single-Chain Fv analogue Produced in *Escherichia coli*," *Proc. Natl. Acad. Sci. U.S.A.* 85(16):5879-5883, (Aug. 1988).
Huston, J.S. et al. "Medical Applications of Single-Chain Antibodies," *Intern. Rev. Immunol.* 10(2-3):195-217, (1993).
Ibragimova, G.T. et al. "Stability of the β-Sheet of the WW Domain: A Molecular Dynamics Simulation Study," *Biophysical Journal* 77:2191-2198, (Oct. 1999).
Idusogie, E.E. et al. "Mapping of the C1q Binding Site on Rituxan, a Chimeric Antibody with a Human IgG1Fc," *The Journal of Immunology* 164:4178-4184, (2000).
International Search Report dated Jul. 29, 2013, for PCT Patent Application No. PCT/EP2013/060529, filed on May 22, 2013, seven pages.

(56) References Cited

OTHER PUBLICATIONS

International Search Report dated Dec. 6, 2011, for PCT Patent Application No. PCT/EP2011/064476 filed on Aug. 23, 2011, seven pages.
International Search Report dated Dec. 6, 2011, for PCT Patent Application No. PCT/EP2011/064468 filed on Aug. 23, 2011, seven pages.
International Search Report dated Sep. 29, 2015, for PCT Patent Application No. PCT/EP2015/067369 filed on Jul. 29, 2015, four pages.
International Search Report dated Sep. 9, 2015, for PCT Application No. PCT/EP2015/057165, filed on Apr. 1, 2015, 5 pages. (339.xx ISR).
Jackman, J. et al. "Development of a Two-Part Strategy to Identify a Therapeutic Human Bispecific Antibody That Inhibits IgE Receptor Signaling," *The Journal of Biological Chemistry* 285(27):20850-20859, (Jul. 2, 2010).
Jakobovits, A. et al. "Germ-line Transmission and Expression of a Human-Derived Yeast Artificial Chromosome," *Nature* 362:255-258, (Mar. 1993).
Jakobovits, A. et al. "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).
Jang, Y.-J. et al. "The Structural Basis for DNA Binding by an Anti-DNA Autoantibody," *Mol. Immunol.* 35(18):1207-1217, (1998).
Jefferis, R. et al. "IgG-Fc-Mediated Effector Functions: Molecular Definition of interaction Sites for Effector Ligands and the Role of Glycosylation," *Immunol. Rev.* 163:59-76, (1998).
Jendreyko, n. et al. "Simultaneous, Phenotypic Knockout of VEGF-R2 and Tie-2 With an Intradiabody Enhances Antiangiogenic Effects In Vivo," *Therapieoptimierung and Risikostratifizierung*, Scripps Research Institute, 218:143-151, (2006).
Jia, L. et al. "A Novel Trifunctional IgG-Like Bispecific Antibody to Inhibit HIV-1 Infection and Enhance Lysis of HIV by Targeting Activation of Complement," *Virology Journal* 7(142):1-4, (Jun. 29, 2010).
Johnson, S. et al. "Construction of Single-Chain Fv Derivatives Monoclonal Antibodies and their Production in *Escherichia coli,*" *Methods Enzymol.* 203:88-98, (1991).
Johnson, G. et al. "Kabat Database and Its Applications: 30 Years After the First Variability Plot," *Nucleic Acids Research* 28(1):214-218, (2000).
Kabat, E.A. et al. "Evolutionary and Structural Influences on Light Chain Constant ($C_L$) Region of Human and Mouse Immunoglobulins," *Proc. Natl. Acad. Sci. USA* 72(7):2785-2788, (Jul. 1975).
Kabat, E.A. et al. Sequences of Proteins of Immunological Interest, (Table of Contents and Introduction), 5th edition, Bethesda, MD: Public Health Service, NIH, vol. 1, (1991).
Karadag, A. et al. "ADAM-9 (MDC-9/meltrin-γ), A Member of the A Disintegrin and Metalloproteinase Family, Regulates Myeloma-Cell-Induced Interleukin-6 Production in Osteoblasts by Direct Interaction with the αvβ5 Integrin," *Blood* 107(8):3271-3278, (Apr. 2006, e-pub. Dec. 22, 2005).
Kaufman, R.J. "Overview of Vector Design for Mammalian Gene Expression," *Molecular Biotechnology* 16:151-160, (2000).
Kazama, Y. et al. "Hepsin, A Putative Membrane-Associated Serine Protease, Activates Human Factor VII and Initiates a Pathway of Blood Coagulation on the Cell Surface Leading to Thrombin Formation," *J. Biol. Chem.* 270:66-72, (Jan. 6, 1995).
Keck, P.J. et al. "Vascular Permeability Factor, An Endothelial Cell Mitogen Related to PDGF," *Science* 246:1309-1312, (Dec. 8, 1989).
Kim, I. et al. "Inhibition of Vascular Endothelial Growth Factor-Induced Angiogenesis Suppresses Tumour Growth In Vivo," *Nature* 362:841-844, (Apr. 29, 1993).
Kim, I. et al. "Molecular Cloning and Characterization of a Novel Angiopoietin Family Protein, Angiopoietin-3," *FEBS Let.* 443:353-56, (1999).
Kim, I. et al. "Molecular Cloning, Expression, and Characterization of Angiopoietin-Related Protein. Angiopoietin-Related Protein Induces Endothelial Cell Sprouting," *J. Biol. Chem.* 274(37):26523-26528, (Sep. 10, 1999).
Klein, C. et al. "Progress in Overcoming the Chain Association Issue in Bispecific Heterodimeric IgG Antibodies," *mAbs* 4(6):653-663, (2012).
Kleinschmidt, M. et al. "Design of a Modular Immunotoxin Connected by Polyionic Adapter Peptides," *J. Mol. Biol.* 327(2):445-452, (Mar. 21, 2003).
Kobayashi, H. et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi, H. et al. "Tryptophan H33 Plays an Important Role in Pyrimidine (6-4) Pyrimidone Photoproduct Binding by a High-Affinity Antibody," *Protein Engineering* 12(10):879-844, (1999).
Kodukula, K. et al. "Biosynthesis of Phosphatidylinositol Glycan-Anchored Membrane Proteins: Design of a Simple Protein Substrate to Characterize the Enzyme that Cleaves the COOH-Terminal Signal Peptide," *The Journal of Biological Chemistry* 266(7):4464-4470 (Mar. 5, 1991).
Komiyama, Y. et al. "IL-17 Plays an Important Role in the Developoment of Experimental Autoimmune Encephalomyelitis," *J. Immunol.* 177:566-573, (2006).
Kotake, S. et al. "IL-17 in Synovial Fluids From Patients With Rheumatoid Arthritis is a Potent Stimulator of Osteoclastogenesis,"*J. Clin. Invest.* 103(9):1345-1352, (May 1999).
Krugmann, S. et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Kumar, S. et al. "Molecular Cloning and Expression of the Fabs of Human Autoantibodies in *Escherichia coli,*" *J. Biol. Chem.* 275(45):35129-35136, (Nov. 10, 2000).
Lamkanfi, M. et al. "Inflammasomes: Guardians of Cytosolic Sanctity," *Immunol. Rev.* 227(1):95-105, (Jan. 2009).
Lazar, E. et al. "Transforming Growth Factor α: Mutation of Aspartic Acid 47 and Leucine 48 Results in Different Biological Activities," *Molecular and Cellular Biology* 8(3):1247-1252, (Mar. 1988).
Lee, K.N. et al. "Using Substrate Specificity of Antiplasmin-Cleaving Enzyme for Fibroblast Activation Protein Inhibitor Design," *Biochemistry* 48(23):5149-5158, (Jun. 16, 2009).
Leeman, M.F. et al. "The Structure, Regulation, and Function of Human Matrix Metalloproteinase-13," *Crit. Rev. Biochem. Mol. Biol.* 37(3):149-166, (2002).
Leitzgen, K. et al. "Assembly of Immunoglobulin Light Chains as a Prerequisite for Secretion," *Journal of Biological Chemistry* 272(5):3117-3123, (Jan. 31, 1997).
Leung, D.W. et al. "Vascular Endothelial Growth Factor is a Secreted Angiogenic Mitogen," *Science* 246:1306-1309, (Dec. 8, 1989).
Lewis, M.L. et al. "Generation of Bispecific IgG Antibodies by Structure-Based Design on an Orthogonal Fab Interface," *Nature Biotechnology* 32(2):191-198, (Feb. 1, 2014, e-pub. Jan. 26, 2014).
Liang, W.-C. et al. "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (Jan. 13, 2006).
Lifely, M.R. et al. "Glycosylation and Biological Activity of CAMPATH-1H Expressed in Different Cell Lines and Grown Under Different Culture Conditions," *Glycobiology* 5(8):813-822, (Dec. 1995).
Lin, M.C. et al. "Structure-Function Relationships in Glucagon: Properties of Highly Purified Des-His[1]-, Monoiodo-, and [Des-Asn[28], Thr[29]](Homoserine Lactone[27])-Glucagon," *Biochemistry USA* 14(8):1559-1563, (1975).
Liotta, L.A et al. "Metastatic Potential Correlates with Enzymatic Degradation of Basement Membrane Collagen," *Nature* 284(5751) 67-68, (Mar. 6, 1980).

(56) References Cited

OTHER PUBLICATIONS

Liu, F.-Y. et al. "Clinical and Imaging Diagnosis of Primary Hepatic Lymphoma," *J First Mil Med. Univ,* 25(10):1290-1292, three pages, (2005). (Translation of the Abstract Only.).

Lodish, H. et al. "Post-Translational Modifications and Quality Control in the Rough ER," Chapter 17, Section 17.6 in *Molecular Cell Biology,* 4th edition, W.H. Freeman and Company, New York, pp. 707-712, (1999).

Lopez-Otin, C. et al. "The Regulatory Crosstalk Between Kinases and Proteases in Cancer," *Nat. Rev. Cancer* 10(4):278-292, (Apr. 2010, e-pub. Mar. 19, 2010).

Love, T.W. et al. "Recombinant Antibodies Possessing Novel Effector Functions," *Methods in Enzymology* 178:515-527, (1989).

Lu, D. et al. "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).

Lu, X. et al., "ADAMTS1 and MMP1 Proteolytically Engage EGF-Like Ligands in an Osteolytic Signaling Cascade for Bone Metastasis," *Genes Dev.* 23(16):1882-1894, (Aug. 2009).

Lukas, T.J. et al. "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).

Lund, J. et al. "Oligosaccharide-Protein Interactions in IgG Can Modulate Recognition by Fcγ Receptors," *FASEB Journal* 9:115-119, (1995).

Lynch, C.N. et al. "TWEAK Induces Angiogenesis and Proliferation of Endothelial Cells," *J. Biol. Chem.* 274(13):8455-8459, (Mar. 26, 1999).

Maisonpierre, P.C. et al. "Angiopoietin-2, a Natural Antagonist for Tie2 that Disrupts in vivo Angiogenesis," *Science* 277:55-60, (Jul. 4, 1997).

Makrides, S.C. "Components of Vectors for Gene Transfer and Expression in Mammalian Cells," *Protein Expression and Purification* 17:183-202, (1999).

Mamoune, A. et al., "Calpain-2 as a Target for Limiting Prostate Cancer Invasion," *Cancer Res.* 63(15):4632-4640, (Aug. 2003).

Marks, J.D. et al. "By-Passing Immunization: Human Antibodies From V-gene Libraries Displayed on Phage," *J. Mol. Biol.* 222(3):581-597, (Dec. 5, 1991).

Marsters, S.A. et al. "Identification of a Ligand for the Death-Domain-Containing Receptor Apo3," *Curr. Biol.* 8(9):525-528, (Apr. 13, 1998).

Marvin et al. "Recombinant Approaches to IgG-Like Bispecific Antibodies," *Acta Pharmacol. Sin.* 26:649-658, (2005).

Marvin, J.S. et al. "Bispecific Antibodies for Dual-Modality Cancer Therapy: Killing Two Signaling Cascades with One Stone," *Curr. Opin. Drug Discov. Dev.* 9:184-193, (2006).

Matrisian, L.M. "Cancer Biology: Extracellular Proteinases in Malignancy," *Curr. Biol.* 9(20):R776-R778, (Oct. 1999).

Mattern, J. et al. "Association of Vascular Endothelial Growth Factor Expression With Intratumoral Microvessel Density and Tumour Cell Proliferation in Human Epidermoid Lung Carcinoma," *Brit. J. Cancer* 73:931-934, (1996).

Matusevicius, D. et al. "Interleukin-17 mRNA Expression in Blood and CSF Mononuclear Cells is Augmented in Multiple Sclerosis," *Multiple Sclerosis* 5:101-104, (1999).

McLean, G.R. et al. "A Point Mutation in the CH3 Domain of Human IgG3 Inhibits Antibody Secretion Without Affecting Antigen Specificity", *Molecular Immunology,* 42:1111-1119, (2005).

Meissner, P. et al. "Transient Gene Expression: Recombinant Protein Production with Suspension-Adapted HEK293-EBNA Cells," *Biotechnology and Bioengineering* 75:197-203, (2001).

Melnyk, O. et al. "Vascular Endothelial Growth Factor Promotes Tumor Dissemination by a Mechanism Distinct from Its Effect on Primary Tumor Growth," *Cancer Research* 56:921-924, (Feb. 15, 1996).

Merchant, A.M. et al. "An Efficient Route to Human Bispecific IgG," *Nature Biotechnology* 16:677-681, (Jul. 1998).

Metz, S. et al. "Bispecific Antibody Derivatives with Restricted Binding Functionalities that are Activated by Proteolytic Processing," *Prot. Eng. Des. Sel.* 25(10):571-580. (2012, e-pub. Sep. 13, 2012).

Michaelson, J.S. et al. "Anti-Tumor Activity of Stability-Engineered IgG-like Bispecific Antibodies Targeting TRAIL-R2 and LTβR," *MAbs* 1(2):128-141, (Mar. 2009, e-pub. Mar. 11, 2009).

Miller, K. et al. "Design, Construction, and In Vitro Analyses of Multivalent Antibodies," *J. Immunol.* 170:4854-4861, (2003).

Milstein, C. et al. "Hybrid Hybridomas and Their Use in Immunohistochemistry," *Nature* 305:537-540, (Oct. 6, 1983).

Mimura, Y. et al. "Role of Oligosaccharide Residues of IgG1-Fc in FcγRIIb Binding," *The Journal of Biological Chemistry* 276(49):45539-45547, (Dec. 7, 2001, e-pub. Sep. 20, 2001).

Minn, A.J. et al. "Genes that Mediate Breast Cancer Metastasis to Lung," *Nature* 436(7050):518-524, (Jul. 28, 2005).

Mirny, L. et al. "Protein Folding Theory: From Lattice to All-Atom Models," *Annu. Rev. Biophys. Biomol. Struct.* 30:361-96, (2001).

Morgan, A. et al. "The N-terminal End of the $C_H2$ Domain of Chimeric Human IgG1 anti-HLA-DR is Necessary for C1q, FcγRI and FcγRIII Binding," *Immunology* 86:319-324, (1995).

Morrison, S.L. et al. "Chimeric Human Antibody Molecules: Mouse Antigen-Binding Domains with Human Constant Region Domains," *Proc. Natl. Acad. Sci. USA* 81(21):6851-6855, (Nov. 1984).

Morrison, S.L. "Success in Specification," *Nature* 368:812-813, (Apr. 28, 1994).

Morrison, S.L. et al. "Variable Region Domain Exchange Influences the Functional Properties of IgG," *Journal of Immunology, American Association of Immunologists* 160:2802-2808, (Jan. 1, 1998).

Morrison, S.L. "Two Heads are Better than One," *Nature Biotechnology* 25(11):1233-1234, (Nov. 2007).

Mukhopadhyay, S. et al. "Matrix Metalloproteinase-12 is a Therapeutic Target for Asthma in Children and Young Adults," *J. Allergy Clin. Immunol.* 126(1):70-76, (Jul. 2010, e-pub. May 24, 2010).

Müller, K.M. et al. "The First Constant Domain ($C_H1$ and $C_L$) of an Antibody Used as Heterodimerization Domain for Bispecific Miniantibodies," *FEBS Letters* 422:259-264, (1998).

Müller, D. et al. "Recombinant Bispecific Antibodies for Cellular Cancer Immunotherapy," *Current Opinion in Molecular Therapeutics* 9(4):319-326, (2007).

Müller, D. et al. "Bispecific Antibodies," Chapter 2 in *Handbook of Therapeutic Antibodies*, Dübel, S. ed., Wiley-VCH Verlag GmbH & Company KGaA, Weinheim, pp. 345-378, (2007).

Myatt, E.A. et al. "Pathogenic Potential of Human Monoclonal Immunoglobulin Light Chains: Relationship of in vitro Aggregation to in vivo Organ Deposition," *Proc. Natl. Acad. Sci. USA* 91:3034-3038, (Apr. 1994).

Nagaoka, M. et al. "Single Amino Acid Substitution in the Mouse IgG1 Fc Region Induces Drastic Enhancement of the Affinity to Protein A," *Protein Engineering* 16(4):243-245, (2003).

Netzel-Arnett, S. et al. "Sequence Specificities of Human Fibroblast and Neutrophil Collagenases," *J. Biol. Chem.* 266(11):6747-6755, (Apr. 15, 1991).

Netzel-Arnett, S. et al. "Comparative Sequence Specificities of Human 72- and 92-kDa Gelatinases (Type IV Collagenases) and PUMP (Matrilysin)," *Biochemistry* 32(25):6427-6432, (Jun. 29, 1993).

Neuberger, M.S. et al. "A Hapten-Specific Chimaeric IgE Antibody with Human Physiological Effector Function," *Nature* 314:268-270, (Mar. 21, 1985).

Niwa, R. et al. "IgG Subclass-Independent Improvement of Antibody-Dependent Cellular Cytotoxicity by Fucose Removal from $Asn^{297}$-Linked Oligosaccharides," *J. Immunol. Methods* 306:151-160, (2005, e-pub. Sep. 22, 2005).

Norderhaug, L. et al. "Versatile Vectors for Transient and Stable Expression of Recombinant Antibody Molecules in Mammalian Cells," *Journal of Immunological Methods* 204:77-87, (1997).

Novotný, J. et al. "Structural Invariants of Antigen Binding: Comparison of Immunoglobulin $V_L$-$V_H$ and $V_L$-$V_L$ Domain Dimmers", *Proc. Natl. Acad. Sci. USA,* 82:4592-4596, (Jul. 1985).

(56) References Cited

OTHER PUBLICATIONS

Ohno, S. et al. "Antigen-Binding Specificities of Antibodies are Primarily Determined by Seven Residues of $V_H$," *Proc. Natl. Acad. Sci. USA* 82(9):2945-2949, (May 1985).

Oliner, J. et al. "Suppression of Angiogenesis and Tumor Growth by Selective Inhibition of Angiopoietin-2," *Cancer Cell* 6:507-516, (Nov. 2004).

Orcutt, K.D. et al. "A Modular IgG-scFv Bispecific Antibody Topology," *Protein Engineering, Design & Selection* 23(4):221-228, (Apr. 2010, e-pub. Dec. 17, 2009).

Orlandi, R. et al. "Cloning Immunoglobulin Variable Domains for Expression by the Polymerase Chain Reaction," *Proc. Natl. Acad. Sci. USA* 86:3833-3837, (May 1989).

Pace, C.N. et al. "How to Measure and Predict the Molar Absorption Coefficient of a Protein," *Protein Science* 4(11):2411-2423, (Nov. 1995).

Pakula, A.A. et al. "Genetic Analysis of Protein Stability and Function," *Annu. Rev. Genet.* 23:289-310, (1989).

Pan, Q. et al. "Blocking Neuropilin-1 Function Has an Additive Effect with nti-VEGF to Inhibit Tumor Growth," *Cancer Cell* 11:53-67, (Jan. 2007).

Patentee's Submission of Jun. 11, 2012, for European Patent No. 1 957 533, filed on Oct. 23, 2006, Reply to Communication Pursuant to Article 94(3) EPC dated Dec. 2, 2011, 7 pages.

Paul, W.E. "Immunoglobulins: Structure and Function," in *Fundamental Immunology*, Jeske, D.D. et al. New York, New York, Raven Press, p. 131-165. (1 page translation of 7.9.1 Disculfide Bonds), (1984).).

Pleass, R.J. et al. "Identification of Residues in the CH2/CH3 Domain Interface of IgA Essential for Interaction With the Human Fcα Receptor (Fcα R) CD89," *The Journal of Biology Chemistry* 274(33):23508-23514, (Aug. 13, 1999).

Plückthun, A. et al. "New Protein Engineering Approaches to Multivalent and Bispecific Antibody Fragments," *Immunotechnology* 3:83-105, (1997).

Prescission Protease, GE Healthcare Catalogue No. 27-0843-01, located at <http://www.gelifesciences.com/webapp/wcs/stores/servlet/productById/en/GELifeScience>, last visited on Jul. 10, 2013, one page.

Radaev, S. et al. "Recognition of IgG by Fcγ Receptor," *The Journal of Biological Chemistry* 276(19):16478-16483, (May 11, 2001).

Rajagopal, V. et al. "A Form of Anti-Tac(Fv) Which is Both Single-Chain and Disulfide Stabilized: Comparison with its Single-Chain and Disulfide-Stabilized Homologs," *Protein Engineering* 10(12):1453-1459, (1997).

Raju, T.S. "Glycosylation Variations with Expression Systems and Their Impact on Biological Activity of Therapeutic Immunoglobulins," *BioProcess International* 1(4):44-53, (Apr. 2003).

Rawlings, N.D. "A Large and Accurate Collection of Peptidase Cleavages in the MEROPS Database," *Database* 2009:1-14, (2009, e-pub. Nov. 2, 2009).

Reiter, Y. et al. "Cytotoxic and Antitumor Activity of a Recombinant Immunotoxin Composed of Disulfide-Stabilized Anti-Tac Fv Fragment and Truncated *Pseudomonas* Exotoxin," *International Journal of Cancer* 58:142-149, (1994).

Reiter, Y. et al. "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704, (May 1994).

Reiter, Y. et al. "Antitumor Activity and Pharmacokinetics in Mice of a Recombinant Immunotoxin Containing a Disulfide-Stabilized Fv Fragment," *Cancer Research* 54:2714-2718, (May 15, 1994).

Reiter, Y. et al. "Stabilization of the Fv Fragments in Recombinant Immunotoxins by Disulfide Bonds Engineered into Conserved Framework Regions," *Biochemistry* 33:5451-5449, (1994).

Reiter, Y. et al. "Improved Binding and Antitumor Activity of a Recombinant Anti-erbB2 Immunotoxin by Disulfide Stabilization of the Fv Fragment," *JBC* 269:18327-18331, (Jul. 15, 1994).

Reiter, Y. et al. "Construction of a Functional Disulfide-Stabilized TCR Fv Indicates That Antibody and TCR Fv frameworks Are Very Similar in Structure," *Immunity* 2:281-287, (Mar. 1995).

Reiter, Y. et al. "Disulfide Stabilization of Antibody Fv: Computer Predictions and Experimental Evaluation," *Protein Engineering* 8(12):1323-1331, (1995).

Reiter, Y. et al. "Antibody Engineering of Recombinant Fv Immunotoxins for Improved Targeting of Cancer: Disulfide-Stabilized Fv Immunotoxins," *Clin. Cancer Res.* 2(2):245-252, (Feb. 1, 1996).

Reiter, Y. et al. "Engineering Antibody Fv Fragments for Cancer Detection and Therapy: Disulfide-Stabilized Fv Fragments," *Nature Biotechnology* 14:1239-1245, (Oct. 1996).

Reyes, A.E. et al. "Pharmacokinetics of a Novel One Armed Antibody to C-Met in Mice, Rats and Monkeys," Genentech, Inc., *Amer. Assn. Pharm. Sci.* 10:S1, (2008).

Ridgway, J.B.B. et al. "'Knobs-into-holes' Engineering of Antibody $C_H3$ Domains for Heavy Chain Heterodimerization," *Protein Engineering* 9(7):617-621, (1996).

Riechmann, L. et al. "Reshaping Human Antibodies for Therapy," *Nature* 332:323-327, (Mar. 24, 1988).

Roitt, A. et al. "Immunology," English Translation by McElroy Translation Company, Moscow "Mir" (2000), p. 110-111, eight pages.

Roitt, A. et al. "Multispecific Antibodies Comprising Full Length Antibodies and Single Chain Fab Fragments," *Immunology*, English Translation, Moscow:Mir, pp. 388-389, (2000).

Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 108(11):707A, Poster Board No. Session 673-II, Abstract No. 2495, from 48th Annual Meeting of the American Society of Hematology, Orland, Florida, Dec. 9-12, 2006, (2006), 3 pages.

Routier, F.H. et al. "The Glycosylation Pattern of a Humanized IgGI Antibody (D1.3) Expressed in CHO Cells," *Glycoconjugate Journal* 14:201-207, (1997).

Rudikoff, S. et al. "Single Amino Acid Substitution Altering Antigen-Binding Specificity," *Proc. Natl. Acad. Sci. USA* 79: 1979-1983, (Mar. 1982).

Rudnick, S.I. et al. "Affinity and Avidity in Antibody-Based Tumor Targeting," *Cancer Biotherapy & Radiopharmaceuticals* 24(2):155-161, (2009).

Ruppert, C. et al. "Protease Levels in Breast, Ovary and other Gynecological Tumor Tissues: Prognostic Importance in Breast Cancer," *Cancer Detect. Prev.* 21(5):452-459, (1997).

Sambrook, J. et al. *Molecular Cloning: A Laboratory Manual* "The Table of Contents" Cold Spring Harbor, New York: Cold Spring Harbor Laboratory Press, (1989).

Schaefer, W. et al. "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).

Schlaeger, E.-J. "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).

Schlaeger, E.-J. et al. "Transient Gene Expression in Mammalian Cells Grown in Serum-free Suspension Culture," *Cytotechnology* 30:71-83, (1999).

Schlatter, S. et al. "On the Optimal Ratio of Heavy to Light Chain Genes for Efficient Recombinant Antibody Production by CHO Cells," *Biotechnol. Prog.* 21:122-133, (2005).

Schmidt, M. et al. "Suppression of Metastasis Formation by a Recombinant Single Chain Antibody-Toxin Targeted to Full-length and Oncogenic Variant EGF Receptors," *Oncogene* 18:1711-1721, (1999).

Schmiedl, A. et al. "Effects of Unpaired Cysteines on Yield, Solubility and Activity of Different Recombinant Antibody Constructs Expressed in *E. coli*" *Journal of Immunological Methods* 242:101-114, (2000).

(56) References Cited

OTHER PUBLICATIONS

Schmiedl, A. et al. "Expression of a Bispecific dsFv-dsFv" Antibody Fragment in Escherichia coli," *Protein Engineering* 13(10):725-734, (Oct. 2000).
Schoonjans, R. et al. "Fab Chains as an Efficient Heterodimerization Scaffold for The Production of Recombinant Bispecific and Trispecific Antibody Derivatives," *Journal of Immunology* 165:7050-7057, (2000).
Schwartz, G.P. et al. "A Superactive Insulin: [B10-Aspartic Acid] Insulin(Human)," *Proc. Natl. Acad. Sci. USA* 84:6408-6411, (Sep. 1987).
Scott, C.J. et al. "Biologic Protease Inhibitors as Novel Therapeutic Agents," *Biochimie*. 92(11):1681-1688, (Nov. 2010, e-pub. Mar. 24, 2010).
Shen, J. et al. "Single Variable Domain-IgG fusion: A Novel Recombinant Approach to Fc Domain-Containing Bispecific Antibodies," *J. of Biological Chemistry* 281(16):10706-10714, (Apr. 21, 2006, e-pub. Feb. 15, 2006).
Shen, J. et al. "Single Variable Domain Antibody as a Versatile Building Block for the Construction of IgG-Like Bispecific Antibodies," *Journal of Immunological Methods* 318:65-74, (2007, e-pub. Oct. 26, 2006).
Shields, R.L. et al. "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (Mar. 2, 2001).
Shields, R.L. et al. "Lack of Fucose on Human IgG1 N-Linked Oligosaccharide Improves Binding to Human FcγRIII and Antibody-dependent Cellular Toxicity," *J. Biol. Chem.* 277(30):26733-26740, (Jul. 26, 2002).
Shinkawa, T. et al. "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity," *J. Biol. Chem.* 278 (5) 3466-3473, (Jan. 31, 2003).
Simmons, L.C. et al. "Expression of Full-Length Immunoglobulins in *Escherichia coli*: Rapid and Efficient Production of Aglycosylated Antibodies," *Journal of Immunological Methods* 263:133-147, (2002).
Simon, T. et al. "Antibody Domain Mutants Demonstrate Autonomy of the Antigen Binding Site," *The EMBO Journal* 9(4):1051-1056, (1990).
Singer, M. et al. "Genes and Genomes," *Moscoer, MIR* 1(1998) 63-64 (With English Translation).
Smith-Gill, S.J. et al. "Contributions of Immunoglobulin Heavy and Light Chains to Antibody Specificity for Lysozyme and Two Haptens," *J. Immunol.* 139(12):4135-4144, (Dec. 15, 1987).
Song, M.-K. et al. "Light Chain of Natural Antibody Plays a Dominant Role in Protein Antigen Binding," *Biochem. Biophys. Res. Comm.* 268(2):390-394, (Feb. 16, 2000).
Stetler-Stevenson, W.G. et al. "Progelatinase A Activation During Tumor Cell Invasion," *Invasion Metastasis* 14(1-6):259-268, (1994-1995).
Stevenson, G.T. et al. "A Chimeric Antibody With Dual Fc Regions (bisFabFc) Prepared by Manipulations at the IgG Hinge," *Anti-cancer Drug Des.* 3(4):219-230, (Mar. 1989).
Stork, R. et al. "A Novel Tri-Functional Antibody Fusion Protein with Improved Pharmacokinetic Properties Generated by Fusing a Bispecific Single-Chain Diabody with an Albumin-Binding Domain from Streptococcal Protein G," *Protein Eng. Des. Sel.* 20(11):569-576, (Nov. 2007, e-pub. Nov. 3, 2007).
Surati, M. et al. "Role of MetMAb (OA-5D5) in c-MET Active Lung Malignancies," *Expert Opin. Biol. Ther.* 11(12):1655-1662, (2011).
Talmadge, J.E. et al. "Murine Models to Evaluate Novel and Conventional Therapeutic Strategies for Cancer," *Am. J. Pathol.* 170(3):793-804, (Mar. 2007).
Tao, M.-H. et al. "The Differential Ability of Human IgG1 and IgG4 to Activate Complement is Determined by the COOH-terminal Sequence of the $C_H2$ Domain," *J. Exp. Med.* 173:1025-1028, (Apr. 1991).

Terpe, K. "Overview of Tag Protein Fusions: From Molecular and Biochemical Fundamentals to Commercial Systems," *Appl. Microbiol. Biotechnol.* 60:523-533, (2003; e-pub. Nov. 7, 2002).
Thommesen, J.E. et al. "Lysine 322 in the Human IgG3 $C_H2$ Domain is Crucial for Antibody Dependent Complement Activation," *Molecular Immunology* 37:995-1004, (2000).
Thurber, G.M. et al. "Antibody Tumor Penetration: Transport Opposed by Systemic and Antigen-Mediated Clearance," *Adv. Drug Deliv. Rev.* 60(12):1421-1434, (Sep. 2008, e-Pub. Apr. 24, 2008).
Torres, M. et al. "Variable-Region-Identical Antibodies Differing in Isotype Demonstrate Differences in Fine Specificity and Idiotype," *The Journal of Immunology,* 174:2132-2142, (2005).
Tripathi, M. et al. "Laminin-332 is a Substrate for Hepsin, a Protease Associated with Prostate Cancer Progression," *JBC* 283(45):30576-30584, (Nov. 7, 2008, e-pub. Sep. 9, 2008).
Ueki, T. et al. "Expression of Hepatocyte Growth Factor and its Receptor c-met Proto-Oncogene in Hepatocellular Carcinoma," *Hepatology* 25(4):862-866, (1997).
Umaña, P. et al. "Engineered Glycoforms of an Antineuroblastoma IgG1 with Optimized Antibody-Dependent Cellular Cytotoxic Activity," *Nature Biotechnology* 17(2):176-180 (Feb. 1999).
Van Dijk, M.A. et al. "Human Antibodies as Next Generation Therapeutics," *Curr. Opin. Chem. Biol.* 5(4):368-74, (Aug. 2001).
Van Spriel, A.B. et al. "Immunotherapeutic Perspective for Bispecific Antibodies," *Immunology Today* 21(8):391-397, (Aug. 2000).
Van't Veer, L.J. et al. "Gene Expression Profiling Predicts Clinical Outcome of Breast Cancer," *Nature* 415(6871):530-536, (Jan. 2002).
Vazquez-Ortiz, G. et al. "Overexpression of Cathepsin F, Matrix Metalloproteinases 11 and 12 in Cervical Cancer," *BMC Cancer* 5:68, (Jun. 30, 2005).
Velasco, G. et al. "Human Cathepsin O: Molecular Cloning from a Breast Carcinoma, Production of the Active Enzyme in *Escherichia coli*, and Expression Analysis in Human Tissues," *J. Biol. Chem.* 269(43):27136-27142, (Oct. 28, 1994).
Veveris-Lowe, T.L. et al. "Seminal Fluid Characterization for Male Fertility and Prostate Cancer: Kallikrein-Related Serine Proteases and whole Proteome Approaches," *Semin. Thromb. Hemost.* 33(1):87-99, (2007).
Vijayalakshmi, M.A. "Antibody Purification Methods," *Applied Biochemistry and Biotechnology* 75:93-102, (1998).
Voskoglou-Nomikos, T. et al. "Clinical Predictive Value of the in Vitro Cell Line, Human Xenograft, and Mouse Allograft Preclinical Cancer Models," *Clin. Can. Res.* 9:4227-4239, (Sep. 15, 2003).
Walker, P.A. et al. "Efficient and Rapid Affinity Purification of Proteins Using Recombinant Fusion Proteases," *Bio/Technology* 12:601-605, (Jun. 12, 1994).
Wallash, C. et al. "Heregulin-Dependent Regulation of HER2/neu Oncogenic Signaling by Heterodimerization With HER3," *EMBO J.* 14(17):4267-4275, (1995).
Ward, E.S. et al. "Binding Activities of a Repertoire of Single Immunoglobulin Variable Domains Secreted From *Escherichia coli*," *Nature* 341:544-546, (Oct. 12, 1989).
Warren, R.S. et al. "Regulation by Vascular Endothelial Growth Factor of Human Colon Cancer Tumorigenesis in a Mouse Model of Experimental Liver Metastasis," *J. Clin. Invest.* 95:1789-1797, (1995).
Webber, K.O. et al. "Preparation and Characterization of a Disulfide-Stabilized Fv Fragment of the Anti-Tac Antibody: Comparison with its Single-Chain Analog," *Molecular Immunology* 32(4):249-258, (1995).
Werner, R.G. et al. "Appropriate Mammalian Expression Systems for Biopharmaceuticals," *Drug Research* 48(8):870-880, (1998).
Wielockx, B. et al. "Matrilysin (Matrix Metalloproteinase-7): A New Promising Drug Target in Cancer and Inflammation?" *Cytokine Growth Factor Rev.* 15(2-3):111-115, (Apr.-Jun. 2004).
Willems, A. et al. "Optimizing Expression and Purification from Cell Culture Medium of Trispecific Recombinant Antibody Derivatives," *Journal of Chromatography B* 786:161-176, (2003).
Woof, J.M. et al. "Human Antibody-FC Receptor Interactions Illuminated by Crystal Structures," *Nat. Rev. Immunol.* 4:1-11, (Feb. 2004).

(56) References Cited

OTHER PUBLICATIONS

Wright, A. et al. "Effect of Glycosylation on Antibody Function: Implications for Genetic Engineering," *Trends in Biotechnology* 15:26-32, (Jan. 1997).
Wright, C.M. et al. "ADAM28: A Potential Oncogene Involved in Asbestos-Related Lung Adenocarcinomas," *Genes Chromosomes Cancer* 49(8):688-698, (Aug. 2010).
Written Opinion of the International Searching Authority dated Dec. 6, 2011, for PCT Patent Application No. PCT/EP2011/064468 filed on Aug. 23, 2011, four pages.
Written Opinion of the International Searching Authority dated Dec. 6, 2011, for PCT Patent Application No. PCT/EP2011/064476 filed on Aug. 23, 2011, four pages.
Written Opinion of the International Searching Authority dated Jul. 29, 2013, for PCT Patent Application No. PCT/EP2013/060529, filed on May 22, 2013, seven pages.
Written Opinion of the International Searching Authority dated Sep. 9, 2015, for PCT Application No. PCT/EP2015/057165, filed on Apr. 1, 2015, 7 pages.
Written Opinion of the International Searching Authority dated Sep. 29, 2015, for PCT Patent Application No. PCT/EP2015/067369 filed on Jul. 29, 2015, four pages.
Wu, C. et al. "Simultaneous Targeting of Multiple Disease Mediators by a Dual-Variable-Domain Immunoglobulin," *Nature Biotechnology* 25(11):1290-1297, (Nov. 2007).
Xie, Z. et al. "A New Format of Bispecific Antibody: Highly Efficient Heterodimerization, Expression and Tumor Cell Lysis," *J. of Immunol. Methods* 296:95-101, (2005).
Yancopoulos, G.D. et al. "Vascular-Specific Growth Factors and Blood Vessel Formation," *Nature* 407:242-248, (Sep. 14, 2000).
Zeidler, R. et al. "Simultaneous Activation of T Cells and Accessory Cells by a New Class of Intact Bispecific Antibody Results in Efficient Tumor Cell Killing," *Journal of Immunology* 163:1246-1252, (1999).
Ziolkowska, M. et al. "High Levels of IL-17 in Rheumatoid Arthritis Patients: IL-15 Triggers In Vitro IL-17 Production Via Cyclosporin A-Sensitive Mechanism," *J. Immunol.* 164:2832-2838, (2000).
Zuo, Z. et al. "An Efficient Route to the Production of an IgG-Like Bispecific Antibody," *Protein Engineering* 13(5):361-367, (2000).
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
Taiwanese Search Report for Taiwanese Patent Application No. 099110151, filed on Apr. 1, 2010, Completion of Search Sep. 12, 2012, 1 page.
International Search Report dated Aug. 5, 2010, for PCT Application No. PCT/EP2010/003559, filed on Jun. 14, 2010, 10 pages.
Russian Office Action dated Apr. 18, 2013, for Russian Patent Application No. 2010 129 539, 3 pages.
Russian Office Action dated Oct. 8, 2014, for Russian Patent Application No. 2012 100 865, 3 pages.
Declaration and Curriculum Vitae for Josh T. Pearson, dated Jan. 17, 2018, 13 pages.

Robbie, G. J. et a l. (Dec. 2013, e-pub. Sep. 30, 2013). "A Novel Investigational Fc-Modified Modified Humanized Monoclonal Antibody, Motavizumab-YTE, Has an Extended Half-Life in Healthy Adults," *Antimicrobial Agents and Chemotherapy* 57(12):6147-6153.
Wang. J. et al. (2016, e-pub. May 15, 2015). "Projected Human Pharmacokinetics of Monoclonal Antibodies From Nonclinical Data: Comparative Evaluation of Prediction Approaches in Early Drug Development," *Biopharm. Drug Dispos.* 37:51-65.
Agata et al. "Expression of the PD-1 Antigen on the Surface of Stimulated Mouse T and B Lymphoctes," *Int. Immunology* 8(5):765-772, (1996).
Anthony, R.M. et al. "A Recombinant IgG Fc That Recapitulates the Antiinflammatory Activity of IVIG," *Science*, 320(5874):373-376, (2008).
Armour, K.L. et al. "Recombinant Human IgG Molecules Lacking Fcγ Receptor I Binding and Monocyte Triggering Activities," *Eur. J. Immunol.* 29:2613-2624, (1999).
Bacac et al. "A Novel Carcinoembryonic Antigen T-Cell Bispecific Antibody (CEA TCB) for the Treatment of Solid Tumors," *Clin. Cancer Res.* 22(13):3286-3297, (2016, e-pub. Feb. 9, 2016).
Bendig. "Humanization of Rodent Monoclonal Antibodies by CDR Grafting," *Methods: A companion to Methods in Enzymology* 8:83-93, (1995).
Boado, R.J. et al. "Engineering and Expression of a Chimeric Transferrin Receptor Monoclonal Antibody for Blood-Brain Barrier Delivery in the Mouse," *Biotechnology and Bioengineering* 102(4):1251-1258, Mar. 1, 2009.
Boado, R.J. et al. "Selective Targeting of a TNFR Decoy Receeptor Pharmaceutical to the Primate Brain As a Receptor-Specific IgG Fusion Protein," *J. Of Biotechnology* 146(1-2):84-91, (Mar. 1, 2010).
Boado, R.J. et al. "Drug Targeting of Erythropoietin Across the Primate Blood-Brain Barrier With an IgG Molecular Trojan Horse," *J. Pharmacology and Experimental Therapeutics* 333(3):961-969, (Jun. 1, 2010).
Brünker et al. "RG7386, A Novel Tetravalent FAP-DR5 Antibody, Effectively Triggers FAP-Dependent, Avidity-Driven DR5 Hyperclustering and Tumor Cell Apoptosis," *Mol. Cancer Ther.* 15(5):946-957, (May 2016, e-pub. Apr. 1. 2016).
Carter, P.J. "Potent Antibody Therapeutics by Design," *Nature Reviews Immunology* 6:343-357, (May 2006).
Castoldi et al. "TetraMabs: Simultaneous Targeting of Four Oncogenic Receptor Tyrosine Kinases for Tumor Growth Inhibition in Heterogeneous Tumor Cell Populations," *Protein Engineering, Design & Selection* 29(10):467-475, (2016, e-pub Aug. 29, 2016).
Chames P. et al. "Bispecific Antibodies for Cancer Therapy," *Current Opinion in Drug Discovery & Development*, 12(2):276-283, (2009).
Chan, A.C. et al. "Therapeutic Antibodies for Autoimmunity and Inflammation," *Nat. Rev. Immunol.* 10(5):301-316, (May 2010).
Charlton. "Expression and Isolation of Recombinant Antibody Fragments in *E. coli*," Chapter 14 in *Methods in Molecular Biology*, B.K.C. Lo, ed. Humana Press, Totowa, NJ, 248:245-254, (2003).
Chen et al. "Improved Variants of SrtA for Site-Specific Conjugation on Antibodies and Proteins With High Efficiency," *Scientific Reports* 6(31899):1-12, (Aug. 18, 2016).
Chin, J.W. et al. "Addition of p-azido-L-Phenylalanine to the Genetic Code of *Escherichia coli*," *J. Am. Chem. Soc.* 124(31):9026-9027, (2002).
Chin, J.W. et al. "In vivo Photocrosslinking With Unnatural Amino Acid Mutagenesis," *ChemBioChem.* 3(11):1135-1137, (2002).
Chin, J.W. et al. (2002). "Addition of a Photocrosslinking Amino Acid to the Genetic Code of *Escherichia coli*," *Proc. Natl. Acad. Sci. U.S.A.* 99(17):11020-11024.
Chinai et al. "New Immunotherapies Targeting the PD-1 Pathway," *Trends in Pharmacological Sciences* 36(9):587-595, (Sep. 2015), 21 pages.
Chowdhury. "Engineering Hot Spots for Affinity Enhancement of Antibodies," Chapter 11 in *Methods in Molecular Biology*, Welschof, M. et al. ed. Humana Press, Totowa, NJ, 207:179-196, (2008).

(56) References Cited

OTHER PUBLICATIONS

Clancy, K.W. et al. "Sortase Transpeptidases: Insights Into Mechanism, Substrate Specificity, and Inhibition," *Biopolymers*, 94(4):385-396, (2010).
Clynes et al. "Fc Receptors are Required in Passive and Active Immunity to Melanoma," *Proc. Natl. Acad. Sci. USA* 95:652-656, (1998).
Cragg et al. "Complement-Mediated Lysis by Anti-CD20 mAb Correlates with Segregation Into Lipid Rafts," *Blood* 101(3):1045-1052, (Feb. 1, 2003.).
Cragg, et al. "Antibody Specificity Controls in Vivo Effector Mechanisms of Anti-CD20 Reagents," *Blood* 103(7):2738-2743, (Apr. 1, 2004).
Croasdale et al. "Development of Tetravalent IgG 1 Dual Targeting IGF-1 R-EGFR Antibodies With Potent Tumor Inhibition," *Archives of Biochemistry and Biophysics* 526:206-218, (2012, e-pub. Mar. 21, 2012).
Cruse, J.M. et al. 2nd ed. CRC Press (2003) p. 37, 316-317.
Cunningham et al. "High-Resolution Epitope Mapping of hGH-Receptor Interactions by Alanine-Scanning Mutagenesis," *Science* 244:1081-1085, (Jun. 2, 1989).
Daëron. "Fe Receptor Biology," *Annu. Rev. Immunol.* 15:203-234, (1997).
De Haard et al. "A large Non-Immunized Human Fab Fragment Phage Library That Permits Rapid Isolation and Kinetic Analysis of High Affinity Antibodies," *The Journal of Biological Chemistry* 274(26):18218-18230, (Jun. 25, 1999).
De Haas et al. "Fcγ Receptors of Phagocytes," *J. Lab. Clin. Med.* 126(4):330-341, (Oct. 1995).
Duncan et al. "The Binding Site for C1q on IgG," *Nature* 332:738-40, (Apr. 21, 1988).
Friend, P.J. et al. "Phase I Study of an Engineered Aglycosylated Humanized CD3 Antibody in Renal Transplant Rejection," *Transplantation.* 68(11):1632-1637, (1999).
Gazzano-Santoro et al. "A Non-Radioactive Complement-dependent Cytotoxicity Assay for Anti-CD20 Monoclonal Antibody," *J. Immunol. Methods* 202:163-171, (1997).
Gerngross. "Advances in the Production of Human Therapeutic Proteins in Yeasts and Filamentous Fungi," *Nat. Biotech.* 22(11):1409-1414, (Nov. 2004).
Graham et al. "Characteristics of a Human Cell Line Transformed by DNA from Human Adenovirus Type 5," *J. Gen Virol.* 36:59-72, (1977).
Guyer et al. "Immunoglobulin Binding by Mouse Intestinal Epithelial Cell Receptors," *J. Immunol.* 117(2):587-593, (Aug. 1976).
Hatfield, K.J. et al. "Antiangiogenic therapy in Acute Myelogenous Leukemia: Targeting of Vascular Endothelial Growth Factor and Interleukin 8 As Possible Antileukemic Strategies," *Curr. Cancer Drug Targets.* 5(4):229-248, (2005).
Hellstrom et al. "Antitumor Effects of L6, an IgG2a Antibody That Reacts with Most Human Carcinomas," *Proc. Natl. Acad. Sci. USA* 83:7059-7063, (Sep. 1986).
Hellstrom et al. "Strong Antitumor Activities of IgG3 Antibodies to a Human Melanoma-Associated Ganglioside," *Proc. Natl. Acad. Sci. USA* 82:1499-1502, (Mar. 1985).
Herberman, "Immunodiagnosis of Cancer," in Fleisher (ed.), "The Clinical Biochemistry of Cancer," p. 347 (American Association of Clinical Chemists (1979).
Hoogenboom et al. "Overview of Antibody Phage-Display Technology and Its Applications," Chapter 1 in *Methods in Molecular Biology*, O'Brien et al. ed. Human Press, Totowa, NJ, 178:1-37, (2001).
Huber, R. et al. "Crystallographic structure studies of an IgG molecule and an Fc fragment," *Nature*, 264:415-420, (1976).
Hudson et al. "Engineered Antibodies," *Nat. Med.* 9:129-134, (2003).
Ilangovan, U. et al. "Structure of Sortase, The Transpeptidase That Anchors Proteins to the Cell Wall of *Staphylococcus aureus*," *Proc. Natl. Acad. Sci. U.S.A.* 98(11):6056-6061, (2001).

Ishida et al. "Induced Expression of PD-1, A Novel Member of the immunoglobulin Gene Superfamily, Upon Programmed Cell Death," *EMBO J.* 11(11):3887-3895, (1992).
Jiang, X.R. et al. "Advances in the assessment and control of the effector functions of therapeutic antibodies," *Nat. Rev. Drug Discov.* 10(2):101-111, (2011).
Kabat et al. "Sequences of Proteins of Immunological Interest," National Institutes of Health, vol. 1, Fifth Edition, pp. 647-723, (1991).
Kam et al. "Carbon Nanotubes as Multifunctional Biological Transporters and Near-Infrared Agents for Selective Cancer Cell Destruction," *Proc. Natl. Acad. Sci. USA* 102(33):11600-11605, (Aug. 16, 2005).
Kanda et al. "Comparison of Cell Lines for Stable Production of Fucose-Negative Antibodies With Enhanced ADCC," *Biotechnol. Bioeng.* 94(4):680-688, (Jul. 5, 2006; e-published Apr. 11, 2006).
Kim et al. "Localization of the Site of the Murine IgG1 Molecule that is Involved in Binding to the Murine Intestinal Fc Receptor," *Eur. J. Immunol.* 24:2429-2434, (1994).
Klein et al. "The Use of CrossMAb Technology for the Generation of Bi- and Multispecific Antibodies," *MABS.* 8(6):1010-1020, (2016).
Labrijn et al. "Species-Specific Determinants in the IgG CH3 Domain Enable Fab-Arm Exchange by Affecting the Noncovalent CH3—CH3 Interaction Strength," *The Journal of Immunology* 187:3238-3246, (2011, e-pub. Aug. 12, 2011).
Lee et al. "Generation and Characterization of a Novel Single-Gene-Encoded Single-Chain Immunoglobulin Molecule With Antigen Binding Activity and Effector Functions" *Mol Immunol.* 36(1):61-71, (1999).
Levary et al. "Protein-Protein fusion catalyzed by sortase A," *PLOS One* 6:e18342.1-e18342.6, (2011).
Lifely et al. "Glycosylation and Biological Activity of CAMPATH-1H Expressed in Different Cell Lines and Grown Under Different Culture Conditions," *Glycobiology* 5(8):813-822, (Dec. 1995).
Madej, M.P. et al. "Engineering of an anti-epidermal growth factor receptor antibody to single chain format and labeling by sortase A-mediated protein ligation," *Biotechnology and Bioengineering* 109(6):1461-1470, (2012).
Mallender et al "Comparative Properties of the Single Chain Antibody and Fv Derivatives of mAb 4-4-20. Relationship Between Interdomain Interactions and the High Affinity for Fluorescein Ligand," *Journal of Biological Chemistry* 271(10):5338-5346, (Mar. 8, 1996).
Mather. "Establishment and Characterization of Two Distinct Mouse Testicular Epithelial Cell Lines," *Biol. Reprod.* 23:243-251, (1980).
Mather et al. "Culture of Testicular Cells in Hormone-Supplemented Serum-Free Medium," *Annals N.Y. Acad. Sci.* 383:44-68, (1982).
Metz, S. et al. "Bispecific Digoxigenin-Binding Antibodies for targeted Payload Delivery," *Proc. Natl. Acad. Sci. U.S.A.* 108 (20):8194-8199, (May 17, 2011).
Mizukami, Y. et al. "Induction of interleukin-8 preserves the angiogenic response in HIf-1α-deficient colon cancer cells," *Nat. Med.* 11(9):992-997, (2005).
Möhlmann S. et al. "In Vitro Sortagging of an Antibody Fab Fragment: Overcoming Unproductive Reactions of Sortase With Water and Lysine Side Chains," *Chembiochem: A European Journal of Chemical Biology.* 12(11):1774-1780, (2011).
Noren, C.J. et al. "A General Method for Site-Specific Incorporation of Unnatural Amino Acids into Proteins," *Science.* 244:182-188, (1989).
Novellino, L. et al. "A Listing of Human Tumor Antigens Recognized by T Cells: Mar. 2004 Update," *Cancer Immunol. Immunother.* 54(3):187-207, (2005).
Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).
Olafsen, T. et al. "Complement-Mediated lysis of Cultured Osteosarcoma Cell Lines Using Chimeric Mouse/Human TP-1 IgG1 and IgG3 Antibodies," *Cancer Immunol. Immunother.* 48:411-418, (1999).
Pardridge, W.M. "Drug Transport Across the Blood-Brain Barrier," *J. Of Cerebral Blood Flow & Metabolism* 32(11):1959-1972, (Aug. 29, 2012).

(56) References Cited

OTHER PUBLICATIONS

Parmiani, G. et al. "Unique Human Tumor Antigens: Immunobiology and Use in Clinical Trials," *J. Immunol*, 178(4):1975-1979, (2007).
Paul. "Structure and Function of Immunoglobulins," Chapter 9 in *Fundamental Immunology*, Third Edition, Raven Press, New York, New York, pp. 292-295, (1993).
Petkova et al. "Enhanced Half-Life of Genetically Engineered Human IgG1 Antibodies in a Humanized FcRn Mouse Model: Potential Application in Humorally Mediated Autoimmune Disease," *Int'l. Immunol.* 18(12):1759-1769, (2006).
Pluckthun. "Antibodies from *Escherichia coli*" Chapter 11 in *The Pharmacology of Monoclonal Antibodies: Handbook of Pharmacology*, Rosenberg and Moore, eds. Berlin:Springer-Verlag, vol. 113, pp. 269-315, (1994).
Popp M.W. et al. "Making and Breaking Peptide Bonds: Protein Engineering Using Sortase," *Angewandte Chemie.* 50(22):5024-5032, (2011).
Presta, L.G. "Molecular Engineering and Design of Therapeutic Antibodies," *Current Opinion in Immunology* 20:460-470, (2008).
Ravetch et al. "Fc Receptors," *Annu. Rev. Immunol.* 9:457-92, (1991).
Ren, Y. et al. "Macrophage Migration Inhibitory Factor Stimulates Angiogenic Factor Expression and Correlates With Differentiation and Lymph Node Status in Patients With Esophageal Squamous Cell Carcinoma," *Ann. Surg.* 242:55-63, (2005).
Remington's Pharmaceutical Sciences, Table of Contents, 2 pages, (1980).
Ripka et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).
Rose et al. "Quantitative Analysis of the Interaction Strength and Dynamics of Human IgG4 Half Molecules by Native Mass Spectrometry," *Structure* 19:1274-1282, (Sep. 7, 2011).
Routledge, E.G. et al. "The Effect of Aglycosylation on the Immunogenicity of a Humanized Therapeutic CD3 Monoclonal Antibody," *Transplantation*, 60(8):847-853, (1995).
Roux, K.H. et al. "Comparisons of the ability of human IgG3 hinge mutants, IgM, IgE, and IgA2, to form small immune complexes: a role for flexibility and geometry," *J. Immunol.* 161(8):4083-4090, (1998).
Sakamoto et al. "Enzyme-Mediated Site-Specific Antibody-Protein Modification Using a ZZ Domain as a Linker,"*BioConjugate Chem.* 21:2227-2293 (2010, e-pub. Nov. 11, 2010).
Salfeld, J.G. "Isotype Selection in Antibody Engineering," *Nat. Biotechnol.* 25(12):1369-1372, (Dec. 2007).
Schaefer et al. "Heavy and light Chain Pairing of Bivalent Quadroma and Knobs-Into-Holes Antibodies Analyzed by UHR-ESI-QTOF Mass Spectrometry," *mAbs* 8(1):49-55, (Jan. 2016).
Schanzer et al. "XGFR, a Novel Affinity-Matured Bispecific Antibody Targeting IGF-1 R and EGFR With Combined Signaling Inhibition and Enhanced Immune Activation for the Treatment of Pancreatic Cancer," *MABS* 8(4):811-827, (2016).
Scheuer et al. "Anti-Tumoral, Anti-Angiogenic and Anti-Metastatic Efficacy of a Tetravalent Bispecific Antibody (TAvi6) Targeting VEGF-A and Angiopoietin-2," *MABS* 8(3):562-573, (2016).
Sensi, M. et al. "Unique tumor antigens: evidence for immune control of genome integrity and immunogenic targets for T cell-mediated patient-specific immunotherapy," *Clin. Cancer Res.* 12(17):5023-5032, (2006).
Sondermann, P. et al. "The 3.2-A Crystal Structure of the Human IgG1 Fc Fragment-FcγRIII Complex,"*Nature*, 406:267-273, (2000).
Strop, P. et al. "Generating Bispecific Human IgG1 and IgG2 Antibodies from Any Antibody Pair," *Journal of Molecular Biology*, 420(3):204-219, (2012).
Ta, H.T. et al. "Enzymatic Single-Chain Antibody Tagging a Universal Approach to Targeted Molecular Imaging and Cell Homing in Cardiovascular Disease," *Circulation Research*, 109(4):365-373, (2011).

Thies, M.J. et al. "Folding and association of the antibody domain $C_H3$: prolyl isomerization preceeds dimerization," *J. Mol. Biol.* 293:67-79, (1999).
Ton-That, H. et al. "Purification and Characterization of Sortase, The Transpeptidase That Cleaves Surface Proteins of *Staphylococcus aureus* at the Lptxg Motif," Proc. Natl. Acad. Sci. U.S.A. 96(22):12424-12429, (1999).
Tsukiji S. et al. "Sortase-Mediated Ligation: A Gift from Gram-Positive Bacteria to Protein Engineering," *Chembiochem.* 10(5):787-798, (2009).
Urlaub et al. "Isolation of Chinese Hamster Cell Mutants Deficient in Dihydrofolate Reductase Activity," *Proc. Natl. Acad. Sci. USA* 77(7):4216-4220, (Jul. 1980).
Vallböhmer, D. et al. "Molecular Determinants of Cetuximab Efficacy," *J Clin. Oncol.* 23(15):3536-3544, (2005).
Virnekäs et al. "Trinucleotide Phosphoramidites: Ideal Reagents for the Synthesis of Mixed Oligonucleotides for Random Mutagenesis," *Nucleic Acids Res.* 22(25):5600-5607, (Dec. 25, 1994).
Wagner et al. "Bispecific Antibody Generated With Sortase and Click Chemistry Has Broad Antiinfluenza Virus Activity," *Proc. Natl. Acad. Sci. USA* 111:16820-16825, (Nov. 25, 2014).
Wang, L. et al. "Expanding the genetic code," *Chem. Commun (Camb.)* 7:1-11, (2002).
Ward, E.S. et al. "The effector functions of immunoglobulins: implications for therapy,," Ther. *Immunol.* 2:77-94, (1995).
Witte M.D. et al. "Preparation of Unnatural N-To-N And C-To-C Protein Fusions," *Proceedings of the National Academy of Sciences of the United States of America*, 109(30):11993-11998, (2012).
Yamane-Ohnuki et al. "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotech. Bioeng.* 87:614-622, (2004, e-pub. Aug. 6, 2004).
Yazaki et al. "Expression of Recombinant Antibodies in Mammalian Cell Lines," Chapter 15 in *Methods in Molecular Biology*, B.K.C. Lo, ed. Humana Press, Totowa, NJ, 248:255-268, (2003).
Yu, Y.J. et al. "Developing Therapeutic Antibodies for Neurodegenerative Disease," *Neurotherapeutics* 10(3):459-472, (Apr. 3, 2013).
International Search Report dated Jan. 16, 2015, for PCT Application No. PCT/EP2014/071531, filed on Oct. 8, 2014, 6 pages.
International Preliminary Report on Patentability for PCT Application No. PCT/EP2014/079353, dated Jul. 12, 2016, filed Dec. 29, 2014, 9 pages.
International Search Report for PCT Application No. PCT/EP2014/079353, dated Apr. 20, 2015, filed Dec. 29, 2014, 6 pages.
Written Opinion International for PCT Application No. PCT/EP2014/079353, dated Apr. 20, 2015, filed Dec. 29, 2014, 8 pages.
Written Opinion dated Jan. 16, 2015, for PCT Application No. PCT/EP2014/071531, filed on Oct. 8, 2014, 5 pages.
Zhang, Z. et al. "Human Polyvalent Immunoglobulin for Treatment," Foreign Medicine Blood, Transfusion and Hematology 23(6):365, (Dec. 31, 2000). Abstract No. 229. With English Translation.
Gong, S. et al. (2017). "Fabs-In-Tandem Immunoglobulin Is a Novel and Versatile Bispecific Design for Engaging Multiple Therapeutic Targets," Accepted Manuscript EpimAb Biotherapeutics, Shanghi, China, pp. 1-36.
Houdebine, L-M. et al. (1994). "Minireview. Production of Pharmaceutical Proteins from Transgenic Animals," Journal of Biotechnology 34:269-287.
Kappell, C.A. et al. (1992). "Regulating Gene Expression in Transgenic Animals," Current Opinions in Biotechnology 3:548-553.
Klement, M. et al. (2015, e-pub. Feb. 16, 2015). "Effect of Linker Flexibility and Length on the Functionality of a Cytotoxic Engineered Antibody Fragment," J. of Biothechnology 1999:90-97.
Todorovska, A. et al. (2001). "Design and Application of Diabodies, Triabodies and Tetrabodies for Cancer Targeting," J. of Immunological Methods 248 :47-66.
Wall, R.J. et al. (1996). "Trangenic Livestock: Progress and Prospects for the Future," Theriogenology 45:57-68.

FIG. 8A
FIG. 8B
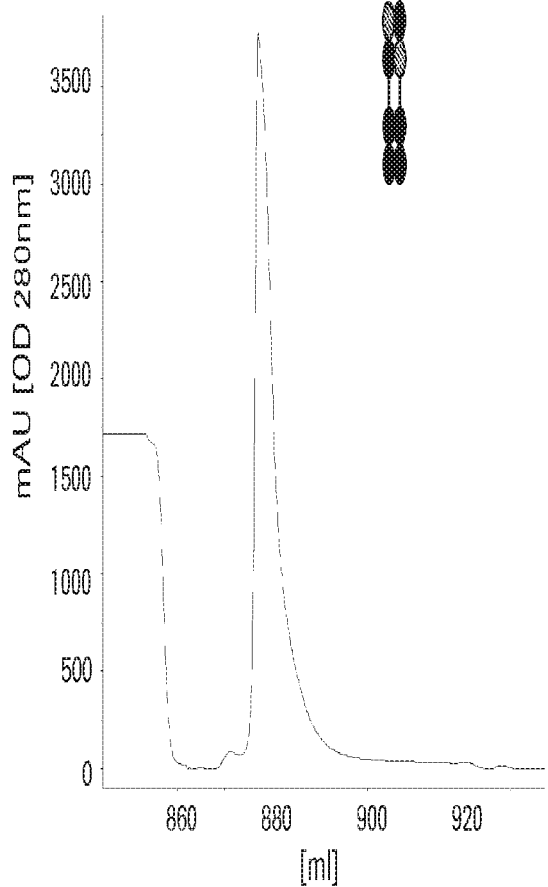
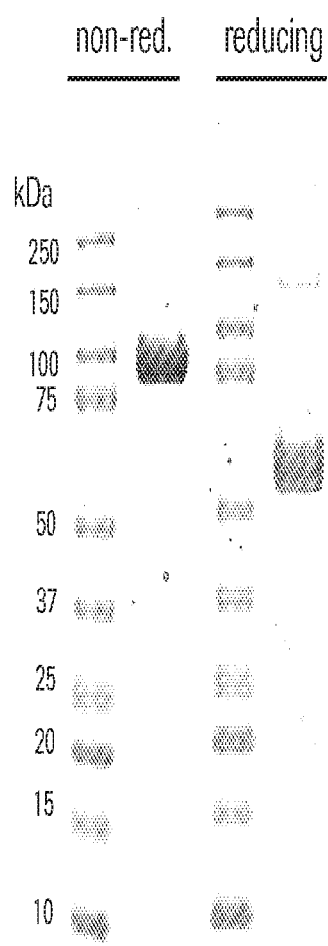

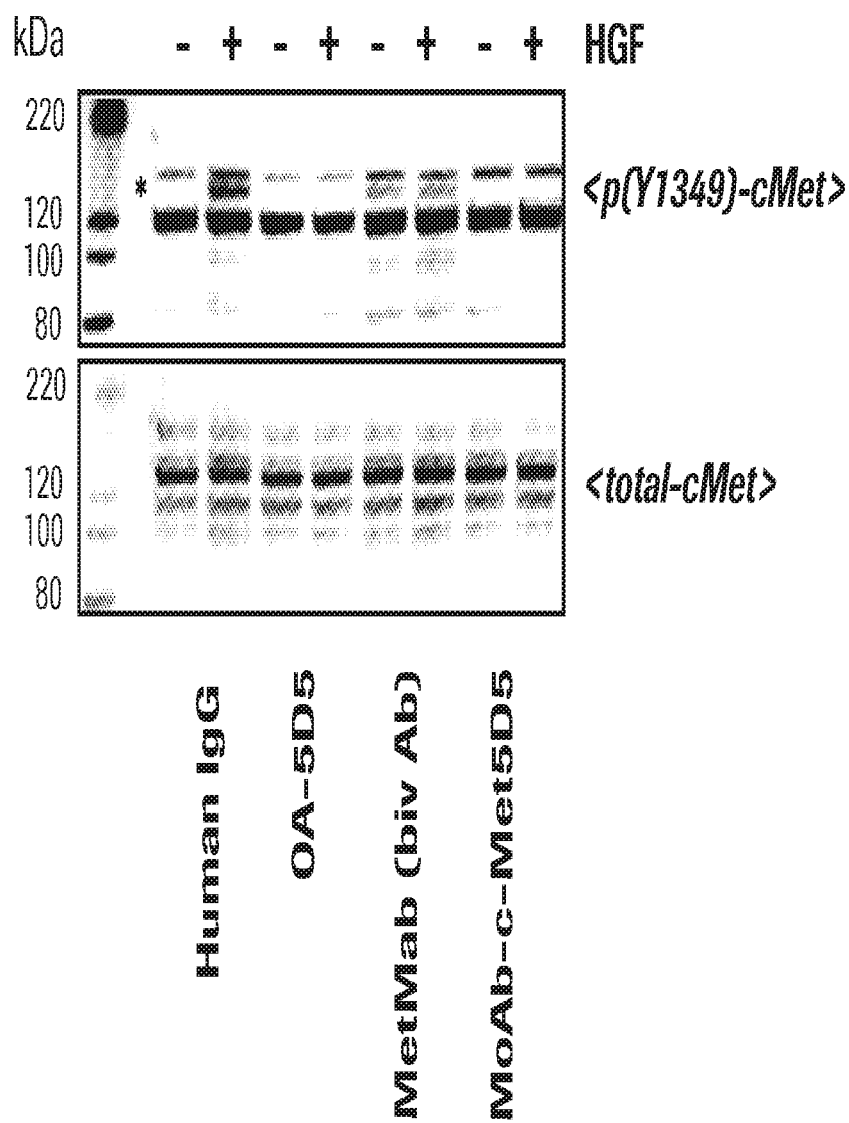

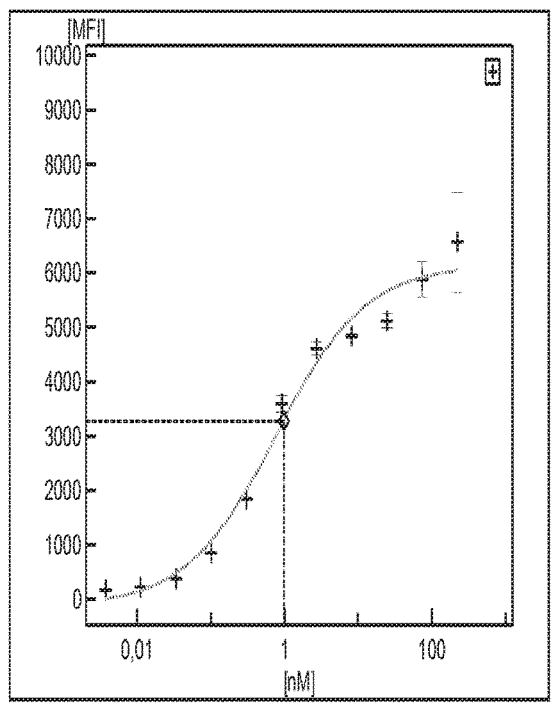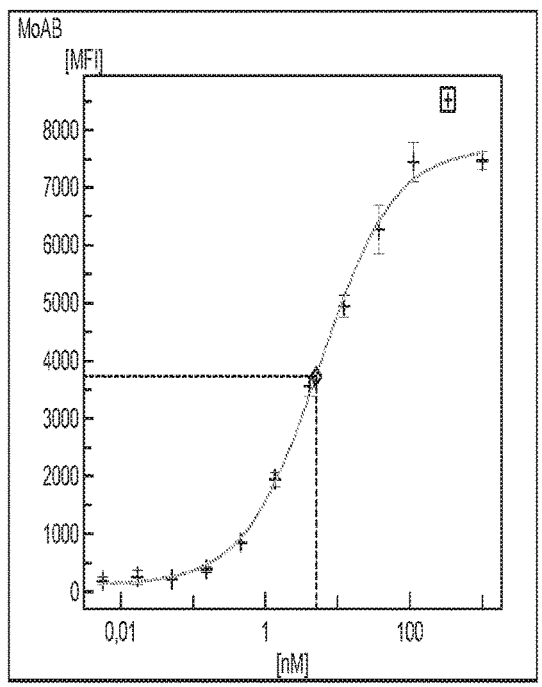
Fig. 12

Fig. 17
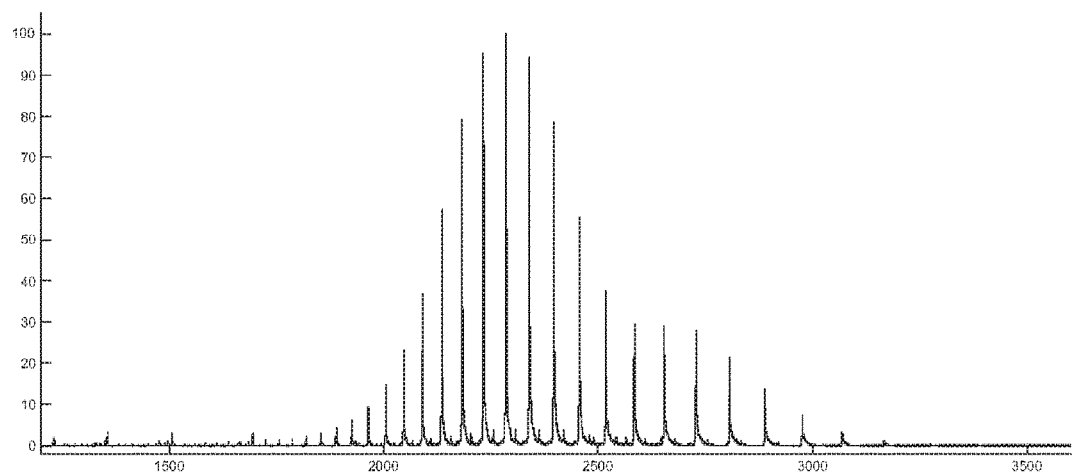
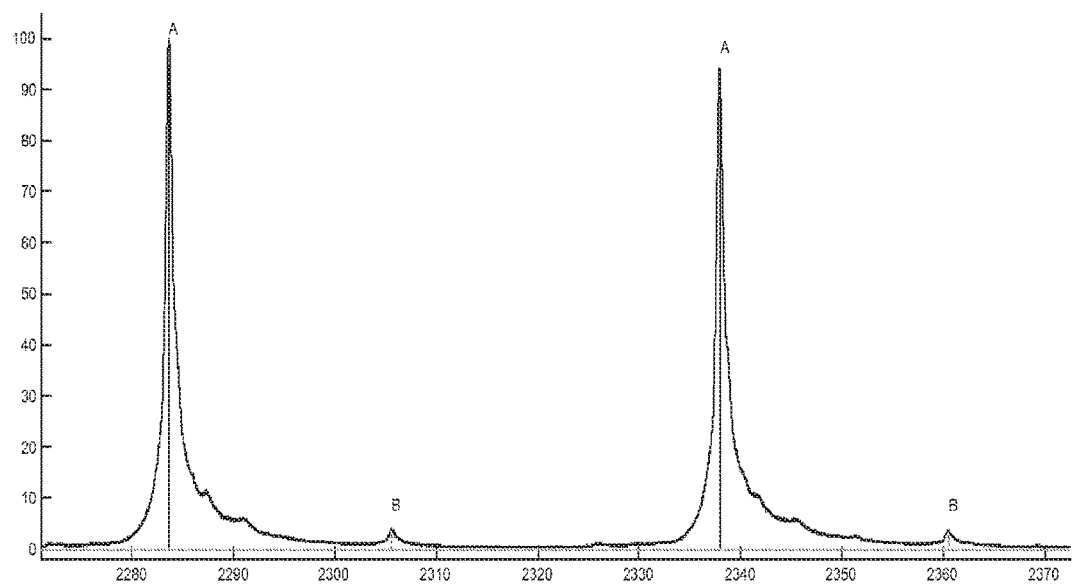

SEQUENCE LISTING

<160> NUMBER OF SEQ ID NOS: 13

<210> SEQ ID NO 1
<211> LENGTH: 445
<212> TYPE: PRT
<213> ORGANISM: Artificial Sequence
<220> FEATURE:
<223> OTHER INFORMATION: Description of Artificial Sequence: Synthetic
      c-Met 5D5 MoAb ("wt") - modified heavy chain a)
      VL-CH1-CH2-CH3 polypeptide

```
<400> SEQUENCE: 1

Asp Ile Gln Met Thr Gln Ser Pro Ser Leu Ser Ala Ser Val Gly
  1               5                  10                  15

Asp Arg Val Thr Ile Thr Cys Lys Ser Gln Ser Leu Leu Tyr Thr
             20                  25                  30

Ser Ser Gln Lys Asn Tyr Leu Ala Trp Tyr Gln Gln Lys Pro Gly Lys
         35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
                100                 105                 110

Lys Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

-continued

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic
      c-Met 5D5 MoAb ("wt") - modified heavy chain b)
      VH-CL-CH2-CH3 polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

```
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 3
<211> LENGTH: 440
<212> TYPE: PRT
<213> ORGANISM: Artificial Sequence
<220> FEATURE:
<223> OTHER INFORMATION: Description of Artificial Sequence: Synthetic
      IGF1R AK18 MoAb ("wt") - modified heavy chain a)
      VL-CH1-CH2-CH3 polypeptide

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205
```

```
Glu Pro Lys Ser Cys Asp Lys Thr His Thr Cys Pro Cys Pro Ala
    210             215                 220
Pro Glu Leu Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser His Glu Asp Pro Glu Val Lys Phe Asn Trp Tyr Val
            260                 265                 270
Asp Gly Val Glu Val His Asn Ala Lys Thr Lys Pro Arg Glu Glu Gln
        275                 280                 285
Tyr Asn Ser Thr Tyr Arg Val Val Ser Val Leu Thr Val Leu His Gln
    290                 295                 300
Asp Trp Leu Asn Gly Lys Glu Tyr Lys Cys Lys Val Ser Asn Lys Ala
305                 310                 315                 320
Leu Pro Ala Pro Ile Glu Lys Thr Ile Ser Lys Ala Lys Gly Gln Pro
                325                 330                 335
Arg Glu Pro Gln Val Tyr Thr Leu Pro Pro Ser Arg Asp Glu Leu Thr
            340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
    370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn His Tyr Thr Gln Lys
            420                 425                 430
Ser Leu Ser Leu Ser Pro Gly Lys
        435                 440

<210> SEQ ID NO 4
<211> LENGTH: 452
<212> TYPE: PRT
<213> ORGANISM: Artificial Sequence
<220> FEATURE:
<223> OTHER INFORMATION: Description of Artificial Sequence: Synthetic
      IGF1R AK18 MoAb ("wt") - modified heavy chain b)
      VH-CL-CH2-CH3 polypeptide

<400> SEQUENCE: 4

Gln Val Glu Leu Val Glu Ser Gly Gly Gly Val Val Gln Pro Gly Arg
1               5                   10                  15
Ser Gln Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ile Ile Trp Phe Asp Gly Ser Ser Thr Tyr Tyr Ala Asp Ser Val
    50                  55                  60
Arg Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Phe Cys
                85                  90                  95
Ala Arg Glu Leu Gly Arg Arg Tyr Phe Asp Leu Trp Gly Arg Gly Thr
            100                 105                 110
```

```
Leu Val Ser Val Ser Ser Ala Ser Val Ala Ala Pro Ser Val Phe Ile
            115                 120                 125

Phe Pro Pro Ser Asp Glu Gln Leu Lys Ser Gly Thr Ala Ser Val Val
130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
            165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
            195                 200                 205

His Gln Gly Leu Ser Ser Pro Val Thr Lys Ser Phe Asn Arg Gly Glu
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 5
<211> LENGTH: 445
<212> TYPE: PRT
<213> ORGANISM: Artificial Sequence
<220> FEATURE:
<223> OTHER INFORMATION: Description of Artificial Sequence: Synthetic
      Her3 205 MoAb ("wt") - modified heavy chain a)
      VL-CH1-CH2-CH3 polypeptide
```

<400> SEQUENCE: 5

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Description of Artificial Sequence: Synthetic
      Her3 205 MoAb ("wt") - modified heavy chain b)
      VH-CL-CH2-CH3 polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
210                 215                 220

Gly Glu Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 7
<211> LENGTH: 445
<212> TYPE: PRT
<213> ORGANISM: Artificial Sequence
<220> FEATURE:
<223> OTHER INFORMATION: Description of Artificial Sequence: Synthetic
      c-Met 5D5 MoAb KiH modified heavy chain a)
      VL-CH1-CH2-CH3 knob T366W, S354C polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Tyr Tyr Ala Tyr Pro Trp Thr Phe Gly Gln Gly Thr Lys Val Glu Ile
        100                 105                 110

Lys Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205
```

```
Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 8
<211> LENGTH: 453
<212> TYPE: PRT
<213> ORGANISM: Artificial Sequence
<220> FEATURE:
<223> OTHER INFORMATION: Description of Artificial Sequence: Synthetic
      c-Met 5D5  MoAb KiH modified heavy chain b)
      VH-CL-CH2-CH3 hole L368A, Y407V, T366S, Y349C
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110
```

```
Thr Leu Val Thr Val Ser Ser Ala Ser Val Ala Ala Pro Ser Val Phe
            115                 120                 125
Ile Phe Pro Pro Ser Asp Glu Gln Leu Lys Ser Gly Thr Ala Ser Val
130                 135                 140
Val Cys Leu Leu Asn Asn Phe Tyr Pro Arg Glu Ala Lys Val Gln Trp
145                 150                 155                 160
Lys Val Asp Asn Ala Leu Gln Ser Gly Asn Ser Gln Glu Ser Val Thr
                165                 170                 175
Glu Gln Asp Ser Lys Asp Ser Thr Tyr Ser Leu Ser Ser Thr Leu Thr
            180                 185                 190
Leu Ser Lys Ala Asp Tyr Glu Lys His Lys Val Tyr Ala Cys Glu Val
        195                 200                 205
Thr His Gln Gly Leu Ser Ser Pro Val Thr Lys Ser Phe Asn Arg Gly
    210                 215                 220
Glu Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Cys Thr Leu Pro Pro Ser Arg Asp Glu Leu Thr Lys Asn Gln
        355                 360                 365
Val Ser Leu Ser Cys Ala Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Val Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 9
<211> LENGTH: 440
<212> TYPE: PRT
<213> ORGANISM: Artificial Sequence
<220> FEATURE:
<223> OTHER INFORMATION: Description of Artificial Sequence: Synthetic
      IGF1R AK18 MoAb KiH modified heavy chain a)
      VL-CH1-CH2-CH3 knob T366W, S354C polypeptide
```

```
<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415
```

```
Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 10
<211> LENGTH: 452
<212> TYPE: PRT
<213> ORGANISM: Artificial Sequence
<220> FEATURE:
<223> OTHER INFORMATION: Description of Artificial Sequence: Synthetic
      IGF1R AK18 MoAb KiH modified heavy chain b)
      VH-CL-CH2-CH3 hole L368A, Y407V, T366S, Y349C
      polypeptide

<400> SEQUENCE: 10

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Cys Thr Leu Pro Pro Ser Arg Asp Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 11
<211> LENGTH: 445
<212> TYPE: PRT
<213> ORGANISM: Artificial Sequence
<220> FEATURE:
<223> OTHER INFORMATION: Description of Artificial Sequence: Synthetic
      Her3 205 MoAb KiH modified heavy chain a)
      VL-CH1-CH2-CH3 knob T366W, S354C polypeptide

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

```
Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 12
<211> LENGTH: 454
<212> TYPE: PRT
<213> ORGANISM: Artificial Sequence
<220> FEATURE:
<223> OTHER INFORMATION: Description of Artificial Sequence: Synthetic
      Her3 205 MoAb KiH modified heavy chain b)
      VH-CL-CH2-CH3 hole L368A, Y407V, T366S,
      Y349C polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
                20                  25                  30

Tyr Ile Ser Trp Val Arg Gln Ala Pro Gly Gln Gly Leu Glu Trp Met
            35                  40                  45

Gly Trp Ile Tyr Ala Gly Thr Gly Ser Pro Ser Tyr Asn Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg His Arg Asp Tyr Tyr Ser Asn Ser Leu Thr Tyr Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag
```

```
<400> SEQUENCE: 13

His His His His His
1               5
```

MONOVALENT ANTIGEN BINDING PROTEINS

CROSS-REFERENCE TO RELATED APPLICATIONS

The application is a divisional application of U.S. patent application Ser. No. 13/406,503, filed Feb. 27, 2012, now abandoned, which claims the benefit of priority under 35 USC § 119(a) to European Patent Application No. EP 11156321.9, filed Feb. 28, 2011, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392015310SeqList.txt, date recorded: Jun. 12, 2017, size: 49 KB).

TECHNICAL FIELD

The present invention relates to monovalent antigen binding proteins with a CHI-CL domain exchange, methods for their production, pharmaceutical compositions containing said antibodies, and uses thereof.

BACKGROUND OF THE INVENTION

In the last two decades various engineered antibody derivatives, either mono or -multispecific, either mono- or multivalent have been developed and evaluated (see e.g. Holliger, P., et al., Nature Biotech 23 (2005) 1126-1136; Fischer N., and Léger O., Pathobiology 74 (2007) 3-14).

For certain antigens as e.g. c-Met monovalent antibodies have different properties such as lack of agonistic function or reduced receptor internalization upon antibody binding than their corresponding bivalent forms and therefore represent attractive formats for therapeutic use. E.g. WO 2005/063816 refers to monovalent antibody fragments as therapeutics.

US 2004/0033561 describes a method for the generation of monovalent antibodies based on the co-expression of a VH-CH1-CH2-CH3 antibody chain with a VL-CL-CH2-CH3 antibody chain; however, a disadvantage of this method is the formation of a binding inactive homodimer of VL-CL-CH2-CH3 chains as depicted in FIG. 2. Due the similar molecular weight such homodimeric by-products are the difficult to separate.

WO 2007/048037 also refers to monovalent antibodies based on the co-expression of a VH-CH1-CH2-CH3 antibody chain with a VL-CL-CH2-CH3 antibody chain, but having a tagging moiety attached to the heavy chain for easier purification of the heterodimer from the difficult-to-separate homodimeric by-product.

WO 2009/089004 describes another possibility to generate a heterodimeric monovalent antibody using electrostatic steering effects.

WO 2010/145792 relates tetravalent bispecific antibodies, wherein mismatched byproducts of similar weight are reduced resulting in higher yields of the desired bispecific antibody.

SUMMARY OF THE INVENTION

The invention comprises a monovalent antigen binding protein comprising a) a modified heavy chain of an antibody which specifically binds to an antigen, wherein the VH domain is replaced by the VL domain of said antibody; and b) a modified heavy chain of said antibody, wherein the CH1 domain is replaced by the CL domain of said antibody.

In one embodiment of the invention the monovalent antigen binding protein according to the invention is characterized in that the CH3 domain of the modified heavy chain of the antibody of a) and the CH3 domain of the modified heavy chain of the antibody of b) each meet at an interface which comprises an original interface between the antibody CH3 domains;

wherein said interface is altered to promote the formation of the monovalent antigen binding protein, wherein the alteration is characterized in that:

i) the CH3 domain of one heavy chain is altered, so that within the original interface the CH3 domain of one heavy chain that meets the original interface of the CH3 domain of the other heavy chain within the monovalent antigen binding protein, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the monovalent antigen binding protein, an amino acid residue is replaced with an amino acid residue having a smaller side chain volume, thereby generating a cavity within the interface of the second CH3 domain within which a protuberance within the interface of the first CH3 domain is positionable.

In one embodiment of the invention this monovalent antigen binding protein according to the invention is characterized in that said amino acid residue having a larger side chain volume is selected from the group consisting of arginine (R), phenylalanine (F), tyrosine (Y), tryptophan (W), and said amino acid residue having a smaller side chain volume is selected from the group consisting of alanine (A), serine (S), threonine (T), valine (V).

In one embodiment of the invention this monovalent antigen binding protein according to the invention is further characterized in that both CH3 domains are further altered by the introduction of cysteine (C) as amino acid in the corresponding positions of each CH3 domain such that a disulfide bridge between both CH3 domains can be formed.

In one embodiment the monovalent antigen binding protein according to the invention is characterized in that is of human IgG isotype.

In one embodiment the monovalent antigen binding protein according to the invention is characterized in comprising a) a modified heavy chain comprising the amino acid sequence of SEQ ID NO:1; and b) a modified heavy chain comprising the amino acid sequence of SEQ ID NO:2;

or a) a modified heavy chain comprising the amino acid sequence of SEQ ID NO:3; and b) a modified heavy chain comprising the amino acid sequence of SEQ ID NO:4;

or a) a modified heavy chain comprising the amino acid sequence of SEQ ID NO:5; and b) a modified heavy chain comprising the amino acid sequence of SEQ ID NO:6;

or a) a modified heavy chain comprising the amino acid sequence of SEQ ID NO:7; and b) a modified heavy chain comprising the amino acid sequence of SEQ ID NO:8;

or a) a modified heavy chain comprising the amino acid sequence of SEQ ID NO:9; and b) a modified heavy chain comprising the amino acid sequence of SEQ ID NO:10;

or a) a modified heavy chain comprising the amino acid sequence of SEQ ID NO: 11; and b) a modified heavy chain comprising the amino acid sequence of SEQ ID NO: 12.

In one aspect of the invention the monovalent antigen binding protein according to the invention is characterized in that the modified heavy chains of a) and b) are of IgG1 isotype, and the antigen binding protein is afucosylated with an the amount of fucose of 80% or less (preferably of 65% to 5%) of the total amount of oligosaccharides (sugars) at Asn297.

The invention further comprises a method for the preparation of a monovalent antigen binding protein according to the invention comprising the steps of a) transforming a host cell with vectors comprising nucleic acid molecules encoding a monovalent antigen binding protein according to the invention b) culturing the host cell under conditions that allow synthesis of said monovalent antigen binding protein molecule; and c) recovering said monovalent antigen binding protein molecule from said culture.

The invention further comprises nucleic acid encoding the monovalent antigen binding protein according to the invention.

The invention further comprises vectors comprising nucleic acid encoding the monovalent antigen binding protein according to the invention.

The invention further comprises host cell comprising said vectors.

The invention further comprises composition, preferably a pharmaceutical or a diagnostic composition of a monovalent antigen binding protein according to the invention.

The invention further comprises pharmaceutical composition comprising a monovalent antigen binding protein according to the invention and at least one pharmaceutically acceptable excipient.

The invention further comprises method for the treatment of a patient in need of therapy, characterized by administering to the patient a therapeutically effective amount of a monovalent antigen binding protein according to the invention.

The antigen binding proteins according to the invention are based on the principle that a VL-CH1-CH2-CH3 and VH-CL-CH2-CH3 chain only forms heterodimers and cannot form a difficult-to-separate homodimeric by-product of similar structure and molecular weight. The effect of this modification lays not primarily in a reduction of by-products, but in that the only by-product which is formed is changed from a homodimeric by-product of similar size into a High-Molecular weight tetramer (FIG. 1C). This High-Molecular weight tetramer then can be easily removed with SEC or other MW separation techniques.

The formed dimeric byproduct (FIG. 1C) can be easily separated due to the different molecular weight (the molecular weight is approximately doubled) and structure. Therefore the purification without the introduction of further modifications (like e.g. genetic introductions of tags) is possible.

It has further been found that the monovalent antigen binding proteins according to the invention have valuable characteristics such as biological or pharmacological activities (as e.g. ADCC, or antagonistic biological activity as well as lack of agonistic activities). They can be used e.g. for the treatment of diseases such as cancer. The monovalent antigen binding proteins have furthermore highly valuable pharmacokinetic properties (like e.g. halftime (term t½) or AUC).

DESCRIPTION OF THE FIGURES

(FIG. 3A) Protein A purified antigen binding protein was separated on a Superdex 200 26/60 column. Individual peaks correspond to MoAb (3), MoAb Dimer (2) and an aggregate fraction (1). (FIG. 3B) Peak fractions (1, 2, 3) were pooled and subjected to SDS-PAGE under non-reducing and reducing conditions. Polyacrylamide gels were stained with Coomassie Blue dye.

(FIG. 4A) Protein A purified antigen binding protein was separated on an Superdex 200 26/60 column. Individual peaks correspond to MoAb (2) and MoAb Dimer (1). (FIG. 4B) Peak fractions (1, 2) were pooled and subjected to SDS-PAGE under non-reducing and reducing conditions. Polyacrylamide gels were stained with Coomassie Blue dye. (FIG. 4C) The molecular mass of the peaks fractions 1 and 2 was investigated by SEC-MALLS. Peak 2 was identified as monovalent antigen binding protein MoAb IGF1R.

(FIG. 5A) Protein A purified antibody was separated on an Superdex 200 26/60 column. Individual peaks correspond to MoAb (3), MoAb Dimer (2) and an aggregate fraction (1). (FIG. 5B) Peak fractions (1, 2, 3) were pooled and subjected to SDS-PAGE under non-reducing and reducing conditions. Polyacrylamide gels were stained with Coomassie Blue dye.

(FIG. 6A)

Protein A purified antigen binding protein was separated on an Superdex 200 26/60 column. (FIG. 6B) Peak fraction was pooled and subjected to SDS-PAGE under non-reducing and reducing conditions. Polyacrylamide gels were stained with Coomassie Blue dye.

(FIG. 7A) Protein A purified antibody was separated on an Superdex 200 26/60 column. Individual peaks correspond to MoAb (2) and MoAb Dimer (1). (FIG. 7B) Peak fractions (1, 2) were pooled and subjected to SDS-PAGE under non-reducing and reducing conditions. Polyacrylamide gels were stained with Coomassie Blue dye.

FIGS. 8A and 8B Biochemical characterization of MoAb c-Met with KiH mutations (c-Met 5D5 MoAb KiH). (FIG. 8A) Protein A purified antibody was separated on an Superdex 200 26/60 column. (FIG. 8B) Peak fraction was pooled and subjected to SDS-PAGE under non-reducing and reducing conditions. Polyacrylamide gels were stained with Coomassie Blue dye.

FIG. 9 c-Met receptor phosphorylation assay in A549 cells. A549 cells were stimulated with HGF in the absence or presence of c-Met binding antibodies or c-Met 5D5 MoAb ("wt")). Total cell lysates were subjected to immunoblot analysis. Asterisk marks phospho-c-Met band in between two unspecific bands.

FIG. 12 Cellular binding of MoAb IGF-1R (IGF1R AK18 MoAb ("wt")) to A549 cells with flow cytometric analysis. A549 cells were incubated with a dilution series of the indicated antibodies. Bound antibodies were visualized with an Fc-binding secondary fluorophor coupled antibody.

FIG. 17 ESI-MS spectrum of the monovalent antigen binding protein IGF1R MoAb (IGF1R AK18 MoAb ("wt")) after deglycosylation and under non-reducing conditions.

DETAILED DESCRIPTION OF THE INVENTION

Figure 1A:
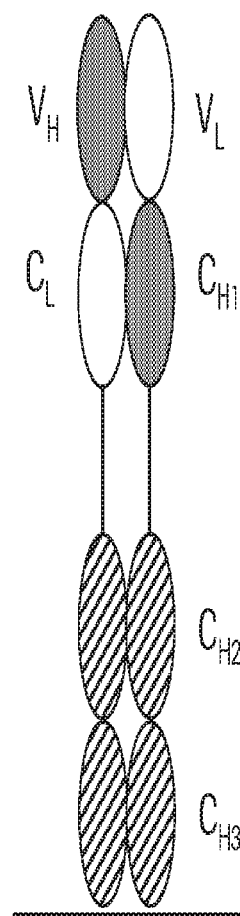
FIG. 1A) Scheme of the monovalent antigen binding protein according to the invention with CH1-CL domain exchange based on VL-CH1-CH2-CH3 and VH-CL-CH2-CH3 chains (abbreviated as MoAb).

The invention comprises a monovalent antigen binding protein comprising
a) a modified heavy chain of an antibody which specifically binds to an antigen, wherein the VH domain is replaced by the VL domain of said antibody; and
b) a modified heavy chain of said antibody, wherein the CH1 domain is replaced by the CL domain of said antibody.

In one preferred embodiment of the invention the CH3 domains of said monovalent antigen binding protein according to the invention can be altered by the "knobs-into-holes" (KiH) technology which is described in detail with several examples in e.g. WO 96/027011, Ridgway, J. B., et al., Protein Eng. 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The effect of this modification is that the High-Molecular weight tetramer by-product, is reduced significantly.

The introduction of a disulfide bridge further stabilizes the heterodimers (Merchant, A. M., et al., Nature Biotech 16 (1998) 677-681; Atwell, S., et al. J. Mol. Biol. 270 (1997) 26-35) and increases the yield.

Thus in one aspect of the invention said monovalent antigen binding protein is further characterized in that
the CH3 domain of the heavy chain of the full length antibody of a) and the CH3 domain of the modified heavy chain of the full length antibody of b) each meet at an interface which comprises an original interface between the antibody CH3 domains;
wherein said interface is altered to promote the formation of the monovalent antigen binding protein, wherein the alteration is characterized in that:
i) the CH3 domain of one heavy chain is altered,
so that within the original interface the CH3 domain of one heavy chain that meets the original interface of the CH3 domain of the other heavy chain within the monovalent antigen binding protein,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
ii) the CH3 domain of the other heavy chain is altered,
so that within the original interface of the second CH3 domain that meets the original interface of the first CH3 domain within the monovalent antigen binding protein,
an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said monovalent antigen binding protein comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M., et al., Nature Biotech 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, said monovalent antigen binding protein comprises Y349C, T366W mutations in one of the two CH3 domains and E356C, T366S, L368A, Y407V mutations in the other of the two CH3 domains or said monovalent antigen binding protein comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1 870 459 A1, can be used alternatively or additionally. A preferred example for said monovalent antigen binding protein are R409D; K370E mutations in the CH3 domain of the "knobs chain" and D399K; E357K mutations in the CH3 domain of the "hole chain" (numbering always according to EU index of Kabat).

In another preferred embodiment said monovalent antigen binding protein comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another preferred embodiment said monovalent antigen binding protein comprises Y349C, T366W mutations in one of the two CH3 domains and S354C, T366S, L368A, Y407V mutations in the other of the two CH3 domains or said monovalent antigen binding protein comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

In one embodiment the monovalent antigen binding protein according to the invention is characterized in comprising
a) a modified heavy chain comprising the amino acid sequence of SEQ ID NO: 1; and
b) a modified heavy chain comprising the amino acid sequence of SEQ ID NO:2.

In one embodiment the monovalent antigen binding protein according to the invention is characterized in comprising
a) a modified heavy chain comprising the amino acid sequence of SEQ ID NO:3; and
b) a modified heavy chain comprising the amino acid sequence of SEQ ID NO:4.

In one embodiment the monovalent antigen binding protein according to the invention is characterized in comprising
a) a modified heavy chain comprising the amino acid sequence of SEQ ID NO:5; and
b) a modified heavy chain comprising the amino acid sequence of SEQ ID NO:6.

In one embodiment the monovalent antigen binding protein according to the invention is characterized in comprising
a) a modified heavy chain comprising the amino acid sequence of SEQ ID NO:7; and
b) a modified heavy chain comprising the amino acid sequence of SEQ ID NO:8.

In one embodiment the monovalent antigen binding protein according to the invention is characterized in comprising
a) a modified heavy chain comprising the amino acid sequence of SEQ ID NO:9; and
b) a modified heavy chain comprising the amino acid sequence of SEQ ID NO: 10.

In one embodiment the monovalent antigen binding protein according to the invention is characterized in comprising
a) a modified heavy chain comprising the amino acid sequence of SEQ ID NO:11; and
b) a modified heavy chain comprising the amino acid sequence of SEQ ID NO: 12.

Figure 1B:
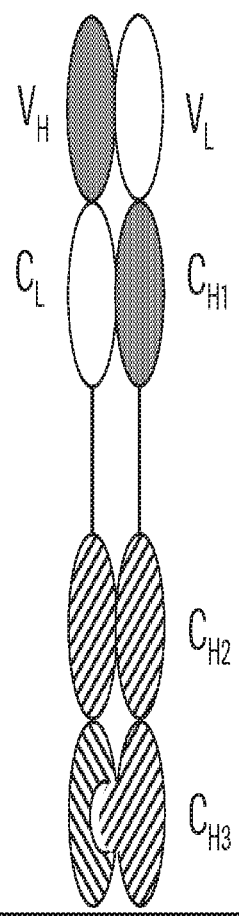
FIG. 1B) Scheme of a MoAb according to the invention including knobs-into-holes in the CH3 domains.

The term "antibody" as used herein denotes a full length antibody consisting of two antibody heavy chains and two antibody light chains (see FIG. 1). A heavy chain of full length antibody is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the heavy chain of full length antibody is a polypeptide consisting in N-terminal to C-terminal direction of VH, CH1, HR, CH2 and CH3. The light chain of full length antibody is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The antibody chains are linked together via inter-polypeptide disulfide bonds between the CL domain and the CH1 domain (i.e. between the light and heavy chain) and between the hinge regions of the full length antibody heavy chains. Examples of typical full length antibodies are natural antibodies like IgG (e.g. IgG1 and IgG2), IgM, IgA, IgD, and IgE.) The antibodies according to the invention can be from a single species e.g. human, or they can be chimerized or humanized antibodies. The full length antibodies according to the invention comprise two antigen binding sites each formed by a pair of VH and VL, which both specifically bind to the same (first) antigen. From the these full length antibodies the monovalent antigen binding proteins of the invention are derived by modifying: a) the first heavy chain of said antibody by replacing the VH domain by the VL domain of said antibody; and by modifying b) the second heavy chain of said antibody by replacing the CH1 domain by the CL domain of said antibody. Thus the resulting monovalent antigen binding protein comprise two modified heavy chains and no light chains.

The C-terminus of the heavy or light chain of said full length antibody denotes the last amino acid at the C-terminus of said heavy or light chain.

The terms "binding site" or "antigen-binding site" as used herein denotes the region(s) of antigen binding protein according to the invention to which a ligand (e.g. the antigen or antigen fragment of it) actually binds and which is derived from antibody molecule or a fragment thereof (e.g. a Fab fragment). The antigen-binding site according to the invention comprise an antibody heavy chain variable domains (VH) and an antibody light chain variable domains (VL).

The antigen-binding sites (i. the pairs of VH/VL) that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of a monovalent antigen binding protein of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. Bispecific antibodies are antibodies which have two different antigen-binding specificities. The monovalent antigen binding proteins according to the invention are "monospecific" and specifically bind to an epitope of the respective antigen.

The term "valent" as used within the current application denotes the presence of a specified number of binding sites in an antibody molecule. A natural antibody for example has two binding sites and is bivalent. The term "monovalent antigen binding protein" denotes the a polypeptide containing only one antigen binding site.

The full length antibodies of the invention comprise immunoglobulin constant regions of one or more immunoglobulin classes. Immunoglobulin classes include IgG, IgM, IgA, IgD, and IgE class (or isotypes) and, in the case of IgG and IgA, their subclasses (or subtypes). In a preferred embodiment, an full length antibody of the invention and thus a monovalent antigen binding protein of the invention has a constant domain structure of an IgG class antibody.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the monovalent antigen binding protein to an epitope of the antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity ($K_D$) of $10^{-8}$ mol/l or less, preferably $10^{-9}$ M to $10^{-13}$ mol/l. Thus, a monovalent antigen binding protein according to the invention is specifically binding to each antigen for which it is specific with a binding affinity ($K_D$) of $10^{-8}$ mol/l or less, preferably $10^{-9}$ M to $10^{-13}$ mol/l.

Binding of the monovalent antigen binding protein to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$($k_D$/ka).

The term "epitope" includes any polypeptide determinant capable of specific binding to a monovalent antigen binding proteins. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by a monovalent antigen binding protein.

In certain embodiments, an antibody is said to specifically bind an antigen when it preferentially recognizes its target antigen in a complex mixture of proteins and/or macromolecules.

In a further embodiment the monovalent antigen binding protein according to the invention is characterized in that said full length antibody is of human IgG1 subclass, or of human IgG1 subclass with the mutations L234A and L235A.

In a further embodiment the monovalent antigen binding protein according to the invention is characterized in that said full length antibody is of human IgG2 subclass.

In a further embodiment the monovalent antigen binding protein according to the invention is characterized in that said full length antibody is of human IgG3 subclass.

In a further embodiment the monovalent antigen binding protein according to the invention is characterized in that said full length antibody is of human IgG4 subclass or, of human IgG4 subclass with the additional mutations S228P and L235E (also named IgG4 SPLE).

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes (also named isotypes): IgA, IgD, IgE, IgG and IgM, and several of these may be further divided into subclasses (also named isotypes), such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and L235E and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Bunkhouse, R. and Cobra, J. J., Mol. Immunol. 16 (1979) 907-917; Burton, D. R., et al., Nature 288 (1980) 338-344; Thomason, J. E., et al., Mol. Immunol. 37 (2000) 995-1004; Idiocies, E. E., et al., J. Immunol. 164 (2000) 4178-4184; Hearer, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

Surprisingly it has been found out that an antigen binding protein according to the invention show improved ADCC properties compared to its parent full length antibody. These improved ADCC effects achieved without further modification of the Fc part like glycoengineering. The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S., L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R., L., et al., J. Biol. Chem. 276 (2001) 6591-6604; Shields, R., L., et al., J. Biol. Chem. 277 (2002) 26733-26740; Simmons, L., C., et al., J. Immunol. Methods 263 (2002) 133-147).

In one aspect of the invention the monovalent antigen binding protein according to the invention is characterized in that the modified heavy chains of a) and b) are of IgG1 isotype, and the antigen binding protein is afucosylated with an the amount of fucose of 80% or less of the total amount of oligosaccharides (sugars) at Asn297.

In one embodiment the antigen binding protein is afucosylated with an the amount of fucose of 65% to 5% of the total amount of oligosaccharides (sugars) at Asn297.

The term "afucosylated antigen binding protein" refers to an antigen binding proteins of IgG1 or IgG3 isotype (preferably of IgG1 isotype) with an altered pattern of glycosylation in the Fc region at Asn297 having a reduced level of fucose residues. Glycosylation of human IgG1 or IgG3 occurs at Asn297 as core fucosylated bianntennary complex oligosaccharide glycosylation terminated with up to 2 Gal residues. These structures are designated as G0, G1 (α1,6 or α1,3) or G2 glycan residues, depending from the amount of terminal Gal residues (Raju, T. S., BioProcess Int. 1 (2003) 44-53). CHO type glycosylation of antibody Fc parts is e.g. described by Routier, F. H., Glycoconjugate J. 14 (1997) 201-207. Antibodies which are recombinantely expressed in non glycomodified CHO host cells usually are fucosylated at Asn297 in an amount of at least 85%. It should be understood that the term an afucosylated antibody as used herein includes an antibody having no fucose in its glycosylation pattern. It is commonly known that typical glycosylated residue position in an antibody is the asparagine at position 297 according to the EU numbering system ("Asn297").

Thus an afucosylated antigen binding protein according to the invention means an antibody of IgG1 or IgG3 isotype (preferably of IgG1 isotype) wherein the amount of fucose is 80% or less (e.g. of 80% to 1%) of the total amount of oligosaccharides (sugars) at Asn297 (which means that at least 20% or more of the oligosaccharides of the Fc region at Asn297 are afucosylated). In one embodiment the amount of fucose is 65% or less (e.g. of 65% to 1%), in one embodiment from 65% to 5%, in one embodiment from 40% to 20% of the oligosaccharides of the Fc region at Asn297. According to the invention "amount of fucose" means the amount of said oligosaccharide (fucose) within the oligosaccharide (sugar) chain at Asn297, related to the sum of all oligosaccharides (sugars) attached to Asn 297 (e.g. complex, hybrid and high mannose structures) measured by MALDI-TOF mass spectrometry and calculated as average value (for a detailed procedure to determine the amount of fucose, see e.g. WO 2008/077546). Furthermore in one embodiment, the oligosaccharides of the Fc region are bisected. The afucosylated antibody according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antibody fucosylation can be predetermined e.g. either by fermentation conditions (e.g. fermentation time) or by combination of at least two antibodies with different fucosylation amount. Such afucosylated antigen binding proteins and respective glycoengineering methods are described in WO 2005/044859, WO 2004/065540, WO 2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antigen binding proteins according to the invention have an increased ADCC (compared to the parent antigen binding proteins). Other glycoengineering methods yielding afucosylated antigen binding proteins according to the invention are described e.g. in Niwa, R. et al., J. Immunol. Methods 306 (2005) 151-160; Shinkawa, T., et al., J. Biol. Chem, 278 (2003) 3466-3473; WO 03/055993 or US 2005/0249722.

Thus one aspect of the invention is an afucosylated antigen binding protein according to the invention which of IgG1 isotype or IgG3 isotype (preferably of IgG1 isotype) with an amount of fucose of 60% or less (e.g. of 60% to 1%) of the total amount of oligosaccharides (sugars) at Asn297, for the treatment of cancer in. In another aspect of the invention is the use of an afucosylated anti-CD20 antibody of IgG1 or IgG3 isotype (preferably of IgG1 isotype) specifically binding to CD20 with an amount of fucose of 60% or less of the total amount of oligosaccharides (sugars) at Asn297, for the manufacture of a medicament for the treatment of cancer. In one embodiment the amount of fucose is between 60% and 20% of the total amount of oligosaccharides (sugars) at Asn297. In one embodiment the amount of fucose is between 60% and 40% of the total amount of oligosaccharides (sugars) at Asn297. In one embodiment the amount of fucose is between 0% of the total amount of oligosaccharides (sugars) at Asn297.

The "EU numbering system" or "EU index (according to Kabat)" is generally used when referring to a residue or position in an immunoglobulin heavy chain constant region (e.g., the EU index is reported in Kabat et al., Sequences of Proteins of Immunological Interest, 5th ed., Public Health Service, National Institutes of Health, Bethesda, Md. (1991) expressly incorporated herein by reference).

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The monovalent antigen binding proteins according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the monovalent antigen binding protein are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of monovalent antigen binding proteins is performed in order to eliminate cellular components or other contaminants, e.g. other cellular nucleic acids or proteins (e.g. byproducts) by standard techniques, including alkaline/SDS treatment, CsCl banding, column chromatography, agarose gel electrophoresis, and others well known in the art (see Ausubel, F., et al. (eds.), Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102). An example of a purification is described in Example 1 and the corresponding FIGS. 3 to 8.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the monovalent antigen binding protein according to the invention for the treatment of cancer.

Another aspect of the invention is said pharmaceutical composition for the treatment of cancer.

One embodiment of the invention is the monovalent antigen binding protein according to the invention for use in the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al., PNAS. 69 (1972) 7110.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO:1 c-Met 5D5 MoAb ("wt")—modified heavy chain a) VL-CH1-CH2-CH3

SEQ ID NO:2 c-Met 5D5 MoAb ("wt")—modified heavy chain b) VH-CL-CH2-CH3

SEQ ID NO:3 IGF1R AK18 MoAb ("wt")—modified heavy chain a) VL-CH1-CH2-CH3

SEQ ID NO:4 IGF1R AK18 MoAb ("wt")—modified heavy chain b) VH-CL-CH2-CH3

SEQ ID NO:5 Her3 205 MoAb ("wt")—modified heavy chain a) VL-CH1-CH2-CH3

SEQ ID NO:6 Her3 205 MoAb ("wt")—modified heavy chain b) VH-CL-CH2-CH3

SEQ ID NO:7 c-Met 5D5 MoAb KiH modified heavy chain a) VL-CH1-CH2-CH3 knob T366W, S354C SEQ ID NO:8 c-Met 5D5 MoAb KiH modified heavy chain b) VH-CL-CH2-CH3 hole L368A, Y407V, T366S, Y349C SEQ ID NO:9 IGF1R AK18 MoAb KiH modified heavy chain a) VL-CH1-CH2-CH3 knob T366W, S354C SEQ ID NO:10 IGF1R AK18 MoAb KiH modified heavy chain b) VH-CL-CH2-CH3 hole L368A, Y407V, T366S, Y349C SEQ ID NO: 11 Her3 205 MoAb KiH modified heavy chain a) VL-CH1-CH2-CH3 knob T366W, S354C SEQ ID NO:12 Her3 205 MoAb KiH modified heavy chain b) VH-CL-CH2-CH3 hole L368A, Y407V, T366S, Y349C

EXAMPLES

The present invention is described in further detain in the following examples which are not in any way intended to limit the scope of the invention as claimed. All references cited are herein specifically incorporated by reference for all that is described therein. The following examples are offered to illustrate, but not to limit the claimed invention.

Experimental Procedures

A. Materials and Methods

Recombinant DNA Techniques

Standard methods were used to manipulate DNA as described in Sambrook, J., et al., Molecular cloning: A laboratory manual; Cold Spring Harbor Laboratory Press, Cold Spring Harbor, N.Y. (1989). The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of subcloned gene fragments was confirmed by DNA sequencing. DNA sequences encoding for the two antibody chains (VH-CL-CH2-CH3 and VL-CH1-CH2-CH3) were prepared as whole fragments by gene synthesis with flanking 5'HpaI and 3'NaeI restriction sites. Gene Segments coding "knobs-into-hole", meaning one antibody heavy chain carrying a T366W mutation in the CH3 domain as well as a second antibody heavy chain carrying T366S, L368A and Y407V mutations in the CH3 domain were synthesized with 5'-BclI and 3'-NaeI restriction sites. In a similar manner, DNA sequences coding "knobs-into-hole" antibody heavy chain carrying S354C and T366W mutations in the CH3 domain as well as a second antibody heavy chain carrying Y349C, T366S, L368A and Y407V mutations were prepared by gene synthesis with flanking BclI and NaeI restriction sites. All constructs were designed with a 5'-end DNA sequence coding for a leader peptide, which targets proteins for secretion in eukaryotic cells.

Construction of the Expression Plasmids

A Roche expression vector was used for the construction of all antibody chains. The vector is composed of the following elements:
an origin of replication, oriP, of Epstein-Barr virus (EBV),
an origin of replication from the vector pUC18 which allows replication of this plasmid in E. coli
a beta-lactamase gene which confers ampicillin resistance in E. coli,
the immediate early enhancer and promoter from the human cytomegalovirus (HCMV),
the human 1-immunoglobulin polyadenylation ("poly A") signal sequence, and
unique HpaI, BclI, and NaeI restriction sites.

The immunoglobulin genes in the order of VH-CL-CH2-CH3 and VL-CH1-CH2-CH3 as well as "knobs-into-hole" constructs were prepared by gene synthesis and cloned into pGA18 (ampR) plasmids as described. The pG18 (ampR) plasmids carrying the synthesized DNA segments and the Roche expression vector were digested either with HpaI and NaeI or with BclI and NaeI restriction enzymes (Roche Molecular Biochemicals) and subjected to agarose gel electrophoresis. Purified DNA segments were then ligated to the isolated Roche expression vector HpaI/NaeI or BclI/NaeI fragment resulting in the final expression vectors. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$. Cells were seeded in fresh medium at a density of $1-2\times10^6$ viable cells/ml on the day of transfection. DNA-293Fectin™ complexes were prepared in Opti-MEM® I medium (Invitrogen, USA) using 325 µl of 293Fectin™ (Invitrogen, Germany) and 250 µg of each plasmid DNA in a 1:1 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Alternatively, antibodies were generated by transient transfection in HEK293-EBNA cells. Antibodies were expressed by transient co-transfection of the respective expression plasmids in adherently growing HEK293-EBNA cells (human embryonic kidney cell line 293 expressing Epstein-Barr-Virus nuclear antigen; American type culture collection deposit number ATCC # CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 µg/ml Geneticin (Gibco). For transfection FuGENE™ 6 Transfection Reagent (Roche Molecular Biochemicals) was used in a ratio of FuGENE™ reagent (µl) to DNA (µg) of 4:1 (ranging from 3:1 to 6:1). Proteins were expressed from the respective plasmids using an equimolar ratio of plasmids. Cells were feeded at day 3 with L-Glutamine ad 4 mM, Glucose [Sigma] and NAA [Gibco]. Bispecific antibody containing cell culture supernatants were harvested from day 5 to 11 after transfection by centrifugation and stored at −200C. General information regarding the recombinant expression of human immunoglobulins in e.g. HEK293 cells is given in: Meissner, P. et al., Biotechnol. Bioeng. 75 (2001) 197-203.

Purification of Antibodies

Antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 or 26/60 gel filtration column (GE Healthcare, Sweden) equilibrated with 20 mM Histidin, 140 mM NaCl, pH 6.0. Fractions containing purified antibodies with less than 5% high molecular weight aggregates were pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-12% Tris-Glycine gels). The aggregate content of antibody samples was analyzed by high-performance SEC using a Superdex 200 analytical size-exclusion column (GE Healthcare, Sweden) in 200 mM $KH_2PO_4$, 250 mM KCl, pH 7.0 running buffer at 25° C. 25 μg protein were injected on the column at a flow rate of 0.5 mL/min and eluted isocratic over 50 minutes. For stability analysis, concentrations of 1 mg/ml of purified proteins were incubated at 4° C. and 40° C. for 7 days and then evaluated by high-performance SEC (e.g. HP SEC Analysis (Purified Protein). The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Mass Spectrometry and SEC-MALLS

Mass Spectrometry

The total deglycosylated mass of antibodies was determined and confirmed via electrospray ionization mass spectrometry (ESI-MS). Briefly, 100 μg purified antibodies were deglycosylated with 50 mU N-Glycosidase F (PNGaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 μg antibody in 115 μl were incubated with 60 μl 1M TCEP and 50 μl 8 M Guanidine-hydrochloride subsequently desalted. The total mass and the mass of the reduced heavy and light chains was determined via ESI-MS on a Q-Star Elite MS system equipped with a NanoMate source. The mass range recorded depends on the samples molecular weight. In general for reduced antibodies the mass range was set from 600-2000 m/z and for non reduced antibodies or bispecific molecules from 1000-3600 m/z.

SEC-MALLS

SEC-MALLS (size-exclusion chromatography with multi-angle laser light scattering) was used to determine the approximate molecular weight of proteins in solution. According to the light scattering theory, MALLS allows molecular weight estimation of macromolecules irrespective of their molecular shape or other presumptions. SEC-MALLS is based on a separation of proteins according to their size (hydrodynamic radius) via SEC chromatography, followed by concentration- and scattered light-sensitive detectors. SEC-MALLS typically gives rise to molecular weight estimates with an accuracy that allows clear discrimination between monomers, dimers, trimers etc., provided the SEC separation is sufficient.

In this work, the following instrumentation was used: Dionex Ultimate 3000 HPLC; column: Superose6 10/300 (GE Healthcare); eluent: 1×PBS; flow rate: 0.25 mL/min; detectors: OptiLab REX (Wyatt Inc., Dernbach), MiniDawn Treos (Wyatt Inc., Dernbach). Molecular weights were calculated with the Astra software, version 5.3.2.13. Protein amounts between 50 and 150 μg were loaded on the column and BSA (Sigma Aldrich) was used as a reference protein.

Dynamic Light Scattering (DLS) Timecourse

Samples (30 μL) at a concentration of approx. 1 mg/mL in 20 mM His/HisCl, 140 mM NaCl, pH 6.0, were filtered via a 384-well filter plate (0.45 μm pore size) into a 384-well optical plate (Corning) and covered with 20 μL paraffin oil (Sigma). Dynamic light scattering data were collected repeatedly during a period of 5 days with a DynaPro DLS plate reader (Wyatt) at a constant temperature of 40° C. Data were processed with Dynamics V6.10 (Wyatt).

c-Met Phosphorylation Assay

5×10e5 A549 cells were seeded per well of a 6-well plate the day prior HGF stimulation in RPMI with 0.5% FCS (fetal calf serum). The next day, growth medium was replaced for one hour with RPMI containing 0.2% BSA (bovine serum albumine). 12.5 μg/mL of the bispecific antibody was then added to the medium and cells were incubated for 15 minutes upon which HGF (R&D, 294-HGN) was added for further 10 minutes in a final concentration of 25 ng/mL. Cells were washed once with ice cold PBS containing 1 mM sodium vanadate upon which they were placed on ice and lysed in the cell culture plate with 100 μL lysis buffer (50 mM Tris-Cl pH7.5, 150 mM NaCl, 1% NP40, 0.5% DOC, aprotinine, 0.5 mM PMSF, 1 mM sodium-vanadate). Cell lysates were transferred to eppendorf tubes and lysis was allowed to proceed for 30 minutes on ice. Protein concentration was determined using the BCA method (Pierce). 30-50 μg of the lysate was separated on a 4-12% Bis-Tris NuPage gel (Invitrogen) and proteins on the gel were transferred to a nitrocellulose membrane. Membranes were blocked for one hour with TBS-T containing 5% BSA and developed with a phospho-specific c-Met antibody directed against Y1349 (Epitomics, 2319-1) according to the manufacturer's instructions. Immunoblots were reprobed with an antibody binding to unphosphorylated c-Met (Santa Cruz, sc-161).

Her3 (ErbB3) Phosphorylation Assay

2×10e5 MCF7 cells were seeded per well of a 12-well plate in complete growth medium (RPMI 1640, 10% FCS). Cells were allowed to grow to 90% confluency within two days. Medium was then replaced with starvation medium containing 0.5% FCS. The next day the respective antibodies were supplemented at the indicated concentrations 1 hour prior addition of 500 ng/mL Heregulin (R&D). Upon addition of Heregulin cells were cultivated further 10 minutes before the cells were harvested and lysed. Protein concentration was determined using the BCA method (Pierce). 30-50 μg of the lysate was separated on a 4-12% Bis-Tris NuPage gel (Invitrogen) and proteins on the gel were transferred to a nitrocellulose membrane. Membranes were blocked for one hour with TBS-T containing 5% BSA and developed with a phospho-specific Her3/ErbB3 antibody specifically recognizing Tyr1289 (4791, Cell Signaling).

FACS

A549 were detached and counted. 1.5×10e5 cells were seeded per well of a conical 96-well plate. Cells were spun down (1500 rpm, 4° C., 5 min) and incubated for 30 min on ice in 50 μL of a dilution series of the respective bispecific antibody in PBS with 2% FCS (fetal calf serum). Cells were again spun down and washed once with 200 μL PBS containing 2% FCS followed by a second incubation of 30 min with 5 μg/mL of Alexa488-coupled antibody directed against human Fc which was diluted in PBS containing 2% FCS (Jackson Immunoresearch, 109116098). Cells were spun down washed twice with 200 μL PBS containing 2% FCS, resuspended in BD CellFix solution (BD Biosciences) and incubated for at least 10 min on ice. Mean fluorescence intensity (mfi) of the cells was determined by flow cytometry (FACS Canto, BD). Mfi was determined at least in duplicates of two independent stainings. Flow cytometry spectra were further processed using the FlowJo software (TreeStar). Half-maximal binding was determined using XLFit 4.0 (IDBS) and the dose response one site model 205.

Surface Plasmon Resonance

The binding properties of monovalent anti-IGF-1R antibodies were analyzed by surface plasmon resonance (SPR) technology using a Biacore instrument (Biacore, GE-Healthcare, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases. For capturing anti-human IgG antibody was immobilized on the surface of a CM5 biosensorchip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 μl/min. Anti-human IgG antibody was injected in sodium acetate, pH 5.0 at 10 μg/ml. A reference control flow cell was treated in the same way but with vehicle buffers only instead of the capturing antibody. Surfaces were blocked with an injection of 1 M ethanolamine/HCl pH 8.5. The IGF-1R antibodies were diluted in HBS-P and injected. All interactions were performed at 25° C. (standard temperature). The regeneration solution of 3 M Magnesium chloride was injected for 60 s at 5 μl/min flow to remove any non-covalently bound protein after each binding cycle. Signals were detected at a rate of one signal per second. Samples were injected at increasing concentrations. FIG. 17 depicts the applied assay format. A low loading density with capturing antibody density and IGF-1R antibody was chosen to enforce monovalent binding.

For affinity measurements, human FcgIIIa was immobilized to a CM-5 sensor chip by capturing the His-tagged receptor to an anti-His antibody (Penta-His, Qiagen) which was coupled to the surface by standard amine-coupling and blocking chemistry on a SPR instrument (Biacore T100). After FcgRIIIa capturing, 50 nM IGF1R antibodies were injected at 25° C. at a flow rate of 5 μL/min. The chip was afterwards regenerated with a 60 s pulse of 10 mM glycine-HCl, pH 2.0 solution.

Antibody-Dependent Cellular Cytotoxicity Assay (ADCC)

Determination of antibody mediated effector functions by anti-IGF-1R antibodies. In order to determine the capacity of the generated antibodies to elicit immune effector mechanisms antibody-dependent cell cytotoxicity (ADCC) studies were performed. To study the effects of the antibodies in ADCC, DU145 IGF-IR expressing cells (1×106 cells/ml) were labeled with 1 μl per ml BATDA solution (Perkin Elmer) for 25 minutes at 37° C. in a cell incubator. Afterwards, cells were washed four times with 10 ml of RPMI-FM/PenStrep and spun down for 10 minutes at 200× g. Before the last centrifugation step, cell numbers were determined and cells diluted to 1×10e5 cells/ml in RPMI-FM/PenStrep medium from the pellet afterwards. The cells were plated 5,000 per well in a round bottom plate, in a volume of 50 μl. HuMAb antibodies were added at a final concentration ranging from 25-0.1 μg/ml in a volume of 50 μl cell culture medium to 50 μl cell suspension. Subsequently, 50 μl of effector cells, freshly isolated PBMC were added at an E:T ratio of 25:1. The plates were centrifuged for 1 minutes at 200× g, followed by an incubation step of 2 hours at 37° C. After incubation the cells were spun down for 10 minutes at 200× g and 20 μl of supernatant was harvested and transferred to an Optiplate 96-F plate. 200 μl of Europium solution (Perkin Elmer, at room temperature) were added and plates were incubated for 15 minutes on a shaker table. Fluorescence is quantified in a time-resolved fluorometer (Victor 3, Perkin Elmer) using the Eu-TDA protocol from Perkin Elmer. The magnitude of cell lysis by ADCC is expressed as % of the maximum release of TDA fluorescence enhancer from the target cells lysed by detergent corrected for spontaneous release of TDA from the respective target cells.

IGF-1R Internalization Assay

The binding of antibodies and antigen binding protein according the invention to the IGF-1R results in internalization and degradation of the receptor. This process can be monitored by incubating IGF-1R expressing HT29 CRC cells with IGF-1R targeting antibodies followed by a quantification of remaining IGF-1R protein levels in cell lysates by ELISA.

For this purpose, HT29 cells at 1.5×104 cells/well were incubated in a 96 well MTP in RPMI with 10% FCS over night at 37° C. and 5% CO2 in order to allow attachment of the cells. Next morning, the medium was aspirated and 100 μl anti IGF-1R antibody diluted in RPMI+10% FCS was added in concentrations from 10 nM to 2 pM in 1:3 dilution steps. The cells were incubated with antibody for 18 hours at 37° C. Afterwards, the medium was again removed and 120 μl MES lysis buffer (25 mM MES pH 6.5+Complete) were added.

For ELISA, 96-Well streptavidin coated polystyrene plates (Nunc) were loaded with 100 μl MAK<hu IGF-1Rα>hu-1a-IgG-Bi (Ch.10) diluted 1:200 in 3% BSA/PBST (final concentration 2.4 μg/ml) and incubated under constant agitation for 1 hour at room temperature. Afterwards, the well content was removed and each well was washed three times with 200 μl PBST. 100 μl of the cell lysate solution were added per well, again incubated for 1 hour at room temperature on a plate shaker, and washed three times with 200 μl PBST. After removal of the supernatant, 100 μl/well PAK<human IGF-1Rα>Ra-C20-IgG (Santa Cruz #sc-713) diluted 1:750 in 3% BSA/PBST was added followed by the same incubation and washing intervals as described above. In order to detect the specific antibody bound to IGF-1R, 100 μl/well of a polyclonal horse-radish-peroxidase-coupled rabbit antibody (Cell Signaling #7074) diluted 1:4000 in 3% BSA/PBST were added. After another hour, unbound antibody was again removed by washing thoroughly 6 times as described above. For quantification of bound antibody, 100 μL/well 3,3'-5,5'-Tetramethylbenzidin (Roche, BM-Blue ID.-Nr. 11484281) was added and incubated for 30 minutes at room temperature. The colorigenic reaction is finally stopped by adding 25 μl/well 1M H2SO4 and the light absorption is measured at 450 nm wavelength. Cells not treated with antibody are used as a control for 0% down-regulation, lysis buffer as background control.

IGF-1R Autophosphorylation Assay (IGF-1 Stimulation)

Targeting IGF-1R by IGF-1R antibodies results in inhibition of IGF-1 induced autophosphorylation. We investigated the inhibition of autophosphorylation of the monovalent IGF-1R antibody without knobs-into-holes compared to the parental IGF.-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of monovalent and bivalent IGF-1R antibody. After lysis of the cells, the levels of phosphorylated IGF-1R protein were determined by a phospho-IGF-1R specific ELISA, combining a human IGF-1R specific capture antibody and a phospho-Tyrosine specific detection antibody.

Determination of PK Properties: Single Dose Kinetics in Mice

Methods

Animals:

NMRI mice, female, fed, 23-32 g body weight at the time point of compound administration.

Study Protocol:

For a single i.v. dose of 10 mg/kg the mice were allocated to 3 groups with 2-3 animals each. Blood samples are taken from group 1 at 0.5, 168 and 672 hours, from group 2 at 24 and 336 hours and from group 3 at 48 and 504 hours after dosing.

Blood samples of about 100 µL were obtained by retrobulbar puncture. Serum samples of at least 40 µl were obtained from blood after 1 hour at room temperature by centrifugation (9300×g) at room temperature for 2.5 min. Serum samples were frozen directly after centrifugation and stored frozen at −20° C. until analysis.

Analytics:

The concentrations of the human antibodies in mice serum were determined with an enzyme linked immunosorbent assay (ELISA) using 1% mouse serum. Biotinylated monoclonal antibody against human Fcγ (mAb<hFcγ$_{PAN}$>IgG-Bi) was bound to streptavidin coated microtiterplates in the first step. In the next step serum samples (in various dilutions) and reference standards, respectively, were added and bound to the immobilized mAb<hFcγ$_{PAN}$>IgG-Bi. Then digoxigenylated monoclonal antibody against human Fcγ (mAb<hFcγ$_{PAN}$>IgG-Dig) was added. The human antibodies were detected via anti-Dig-horseradish-peroxidase antibody-conjugate. ABTS-solution was used as the substrate for horseradish-peroxidase. The specificity of the used capture and detection antibody, which does not cross react with mouse IgG, enables quantitative determination of human antibodies in mouse serum samples.

Calculations:

The pharmacokinetic parameters were calculated by non-compartmental analysis, using the pharmacokinetic evaluation program WinNonlin™, version 5.2.1.

TABLE 1

| Computed Pharmacokinetic Parameters: | | |
|---|---|---|
| Abbreviations of Pharmacokinetic Parameters | Pharmacokinetic Parameters | Units |
| C0 | initial concentration estimated only for bolus IV models | µg/mL |
| C0_NORM | initial concentration estimated only for bolus IV models, dose-normalized | µg/mL/mg/kg |
| T0 | time at initial concentration estimated only for bolus IV models | h |
| TMAX | time of maximum observed concentration | h |
| CMAX | maximum observed concentration, occurring at TMAX | µg/mL |
| CMAX_NORM | Cmax, dose-normalized | µg/mL/mg/kg |
| AUC_0_INF | AUC extrapolated | h*µg/mL |
| AUC_0_LST | AUC observed | h*µg/mL |
| TLAST | Time of last observed concentration > 0 | h |
| AUC_0_INF_NORM | AUC extrapolated, dose-normalized | h*µg/mL/mg/kg |
| AUC_0_LST_NORM | AUC observed, dose-normalized | h*µg/mL/mg/kg |
| PCT_AUC_EXTRA | percentage AUC extrapolated | % |
| CL_TOTAL | total clearance | mL/min/kg |
| CL_TOTAL_CTG | total clearance categories | L, M, H |
| VSS | steady state distribution volume | L/kg |
| VSS_CTG | steady state distribution volume categories | L, M, H |
| VZ | terminal distribution volume | L/kg |
| CL/F | total clearance after non IV routes or after IV route of prodrug | mL/min/kg |
| VZ/F | terminal distribution volume after non IV routes or after IV route of prodrug | L/kg |
| MRT_INF | mean residence time (extrapolated) | h |
| MRT_LST | mean residence time (observed) | h |
| HALFLIFE_Z | terminal halflife | h |
| F | bioavailability after non IV routes or after IV route of prodrug | % |

The following pharmacokinetic parameters were used for assessing the human antibodies:

The initial concentration estimated for bolus IV models (C0).

The maximum observed concentration ($C_{max}$), occurring at ($T_{max}$).

The time of maximum observed concentration ($T_{max}$).

The area under the concentration/time curve AUC(0-Inf) was calculated by linear trapezoidal rule (with linear interpolation) from time 0 to infinity.

The apparent terminal half-life ($T_{1/2}$) was derived from the equation: $T_{1/2}$=ln 2/λz.

Total body clearance (CL) was calculated as Dose/AUC (0-inf).

Volume of distribution at steady state (Vss), calculated as MRT(0-inf)× CL (MRT(0-inf), defined as AUMC(0-inf)/AUC(0-inf).

B. Examples

Example 1

Generation of Monovalent Antibody

We designed monovalent antigen binding proteins against c-Met (SEQ ID NO:1 and SEQ ID NO:2; c-Met 5D5 MoAb ("wt")), IGF-1R (SEQ 1D NO:3 and SEQ ID NO:4.; IGF1R AK18 MoAb ("wt")) and HER3 (SEQ ID NO:5 and SEQ ID NO:6; Her3 205 MoAb ("wt")) based on the design principle as shown in FIG. 1A. In addition, the same monovalent antibodies against c-Met (SEQ ID NO:7 and SEQ ID NO:8; c-Met 5D5 MoAb KiH), IGF-1R (SEQ ID NO:9 and SEQ ID NO:10; IGF1R AK18 MoAb KiH) and HER3 (SEQ ID NO:11 and SEQ ID NO:12; Her3 205 MoAb KiH) were designed incorporating mutations in the CH3 parts to support heterodimerization by the knobs-into-holes (KiH) technology (Merchant, A. M., et al., Nat. Biotechnol. 16 (1998) 677-681). All monovalent antibodies were transiently expressed in HEK293 cells as described above, and subsequently purified via Protein A affinity chromatography followed by size exclusion.

FIGS. 3A, 3B, 4A, 4C, 5A, and 5B depict the chromatograms of the size exclusion chromatography of the three different monovalent antigen binding proteins without knobs-into-holes as well as the corresponding SDS-PAGE under non-reducing and reducing conditions.

Figure 1C:
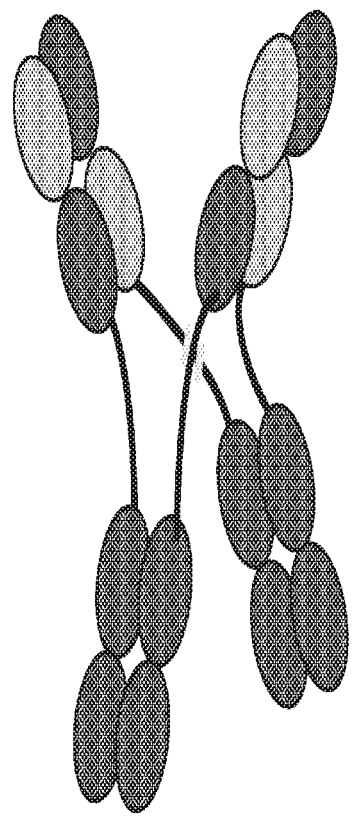
FIG. 1C) Scheme of the dimeric bivalent antigen binding protein (MoAb-Dimer that is formed as a byproduct which can be easily separated due to different structure and molecular weight).
Figure 2A:
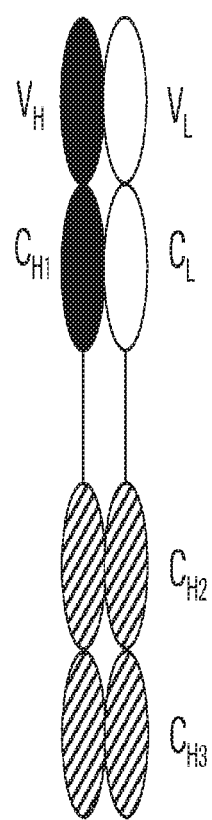
FIG. 2A) Scheme of a monovalent antibody of VL-CL-CH2-CH3 and of VH-CH1-CH2-CH3 chains (described e.g. in US 2004/0033561) and FIG. 2B) the binding inactive difficult-to-separate homodimer byproduct of VL-CL-CH2-CH3 chains (described e.g. in WO 2007/048037).
Figure 2B:
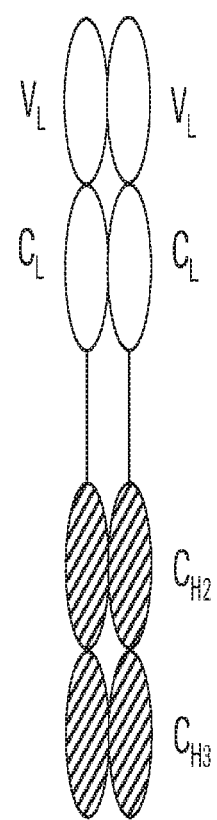
Figure 3A:
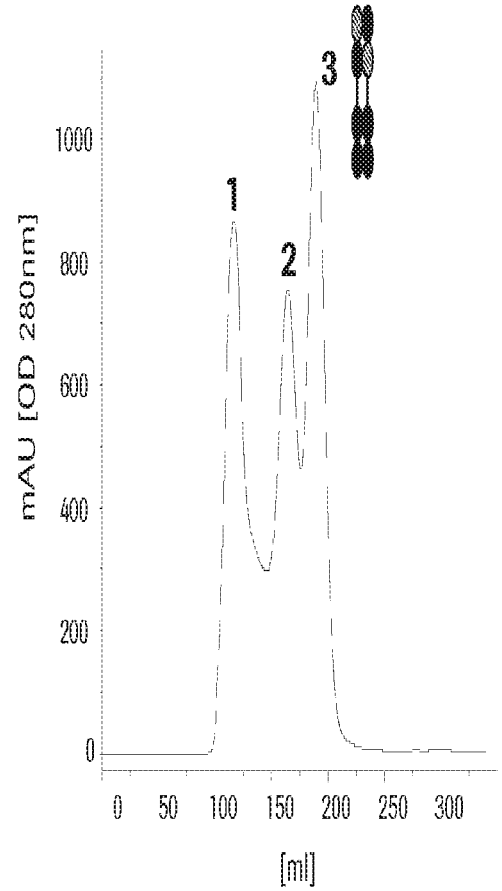
FIGS. 3A and 3B Biochemical characterization of MoAb c-Met (c-Met 5D5 MoAb ("wt")).
Figure 3B:
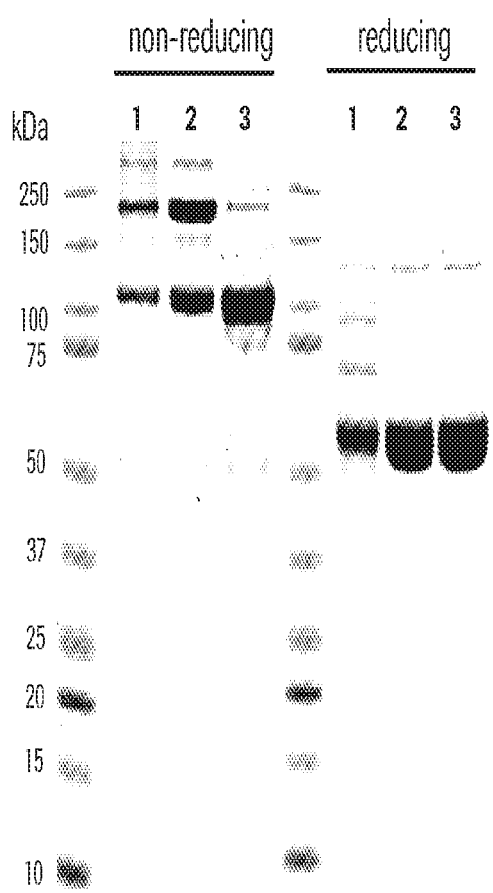
Figure 4A:
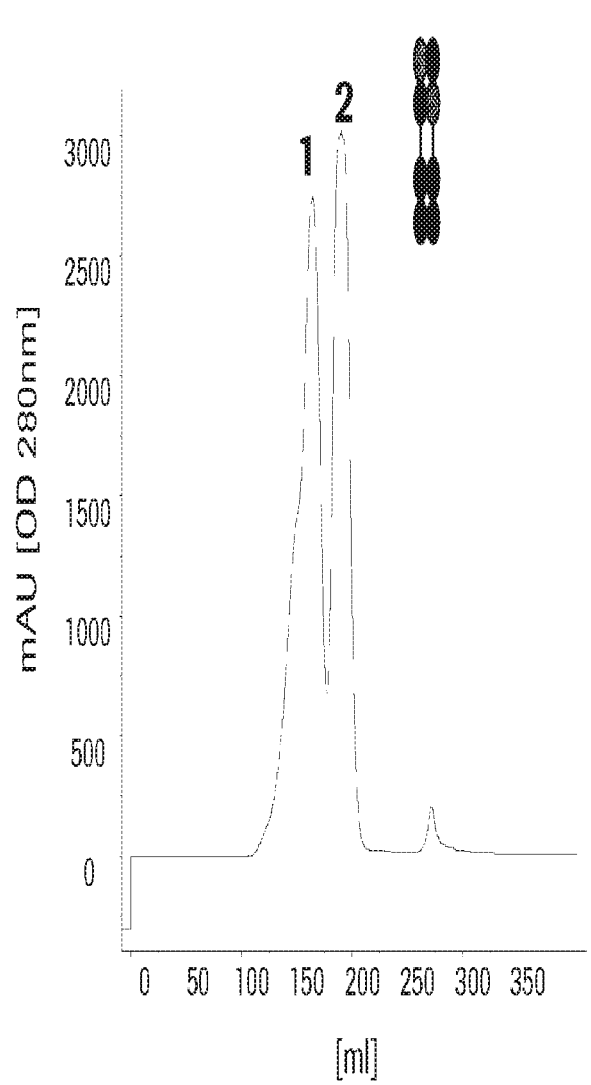
FIGS. 4A-4C Biochemical characterization of monovalent MoAb IGF1R (IGF1R AK18 MoAb ("wt")).
Figure 4B:
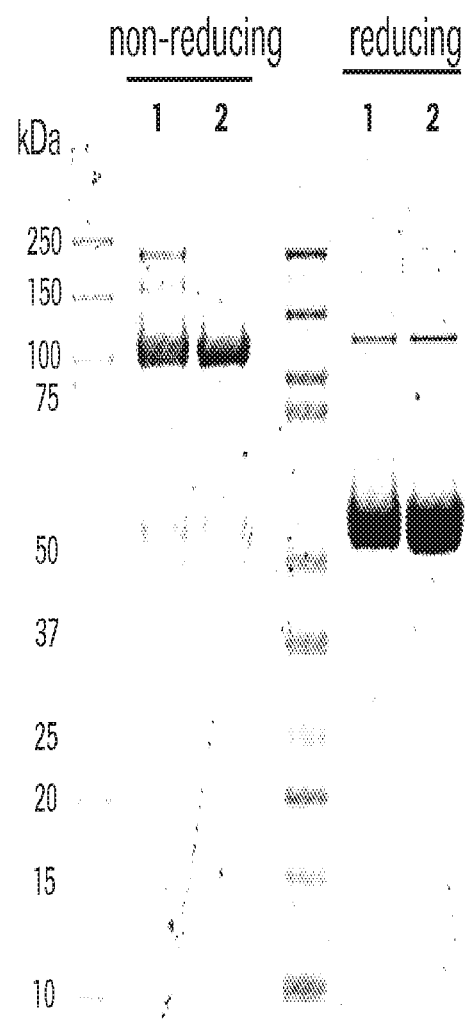
Figure 4C:
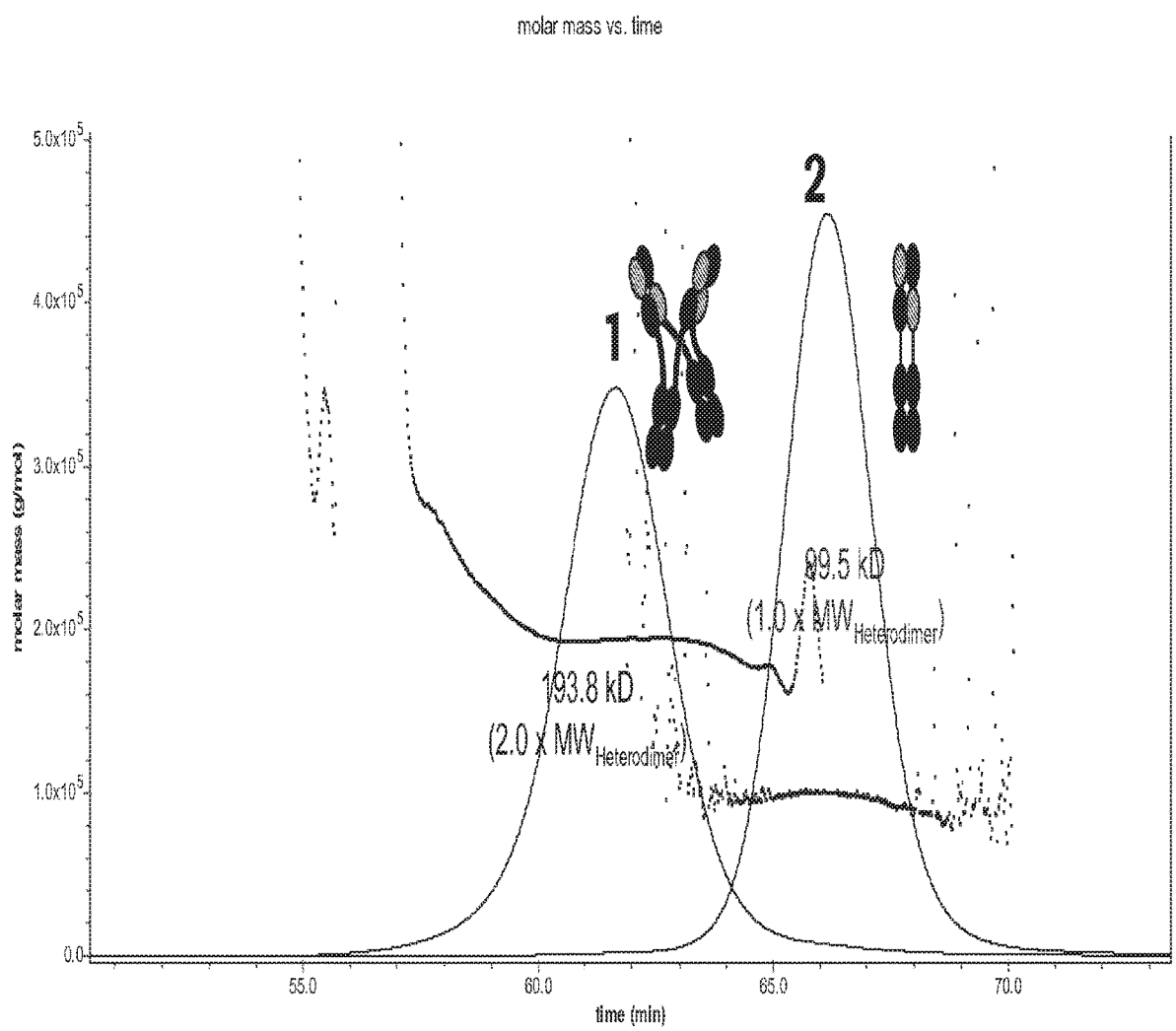
Figure 5A:
FIGS. 5A and 5B Biochemical characterization of MoAb Her3 (Her3 205 MoAb ("wt")).
Figure 5B:
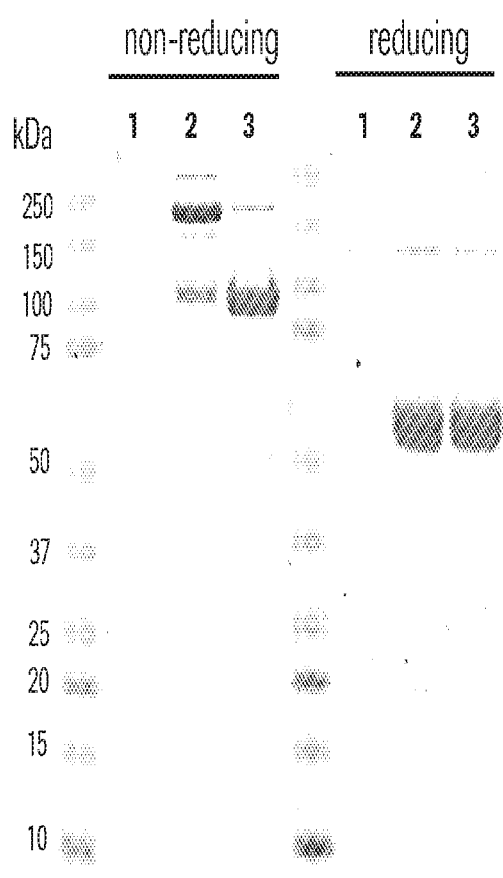
Figure 6A:
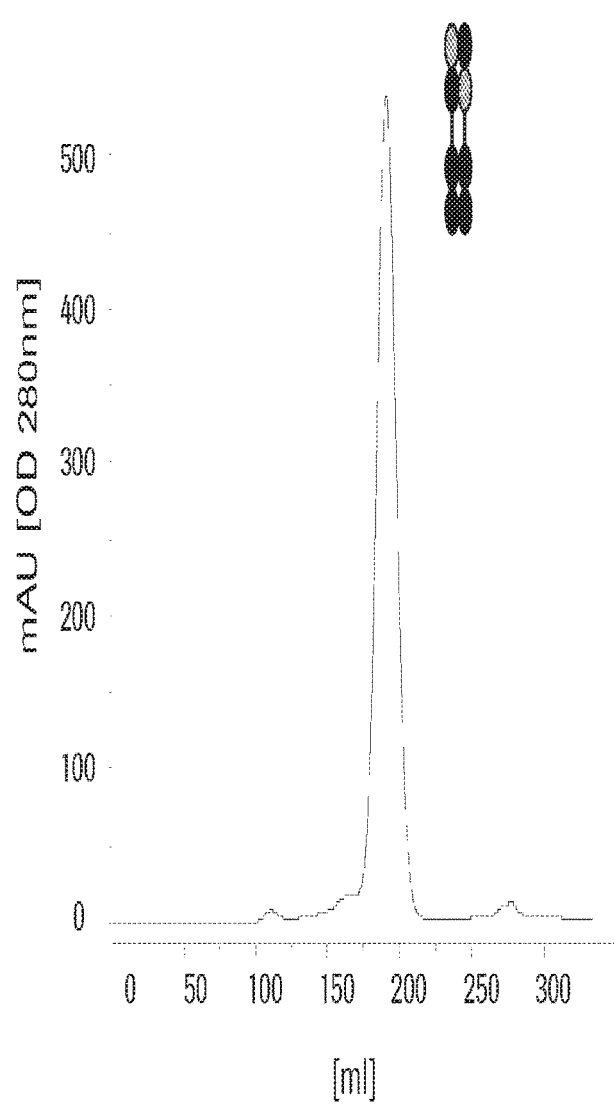
FIGS. 6A and 6B Biochemical characterization of MoAb Her3 with KiH mutations (Her3 205 MoAb KiH).
Figure 6B:
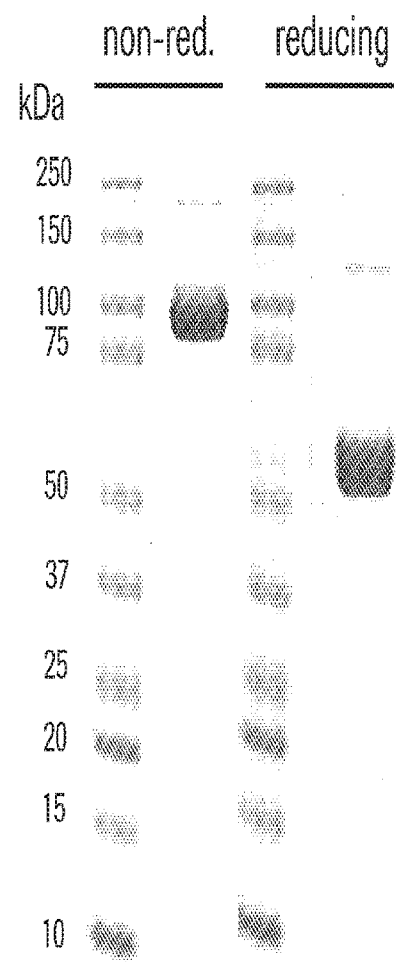
Figure 7A:
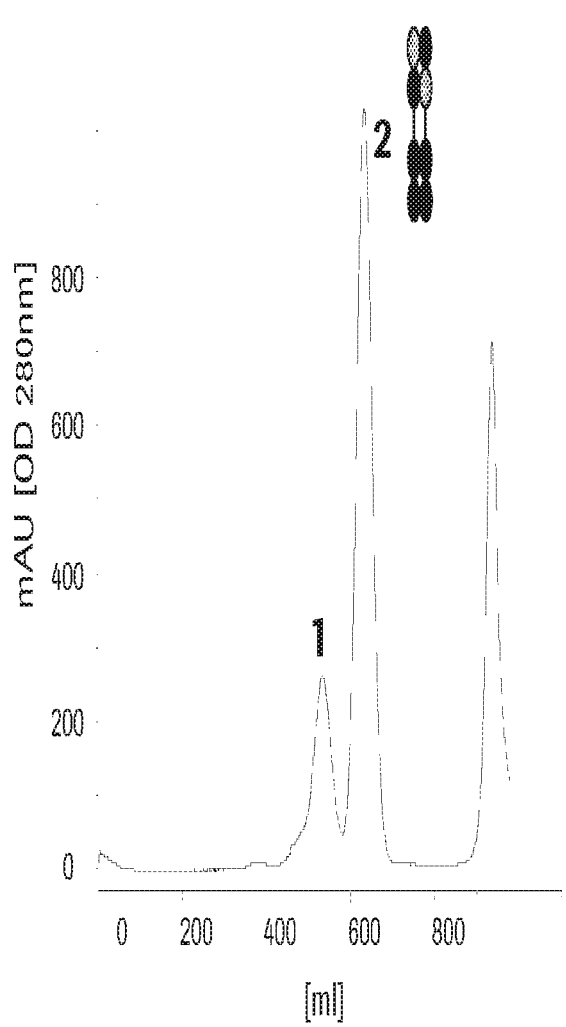
FIGS. 7A and 7B Biochemical characterization of MoAb IGF1R with KiH mutations (IGF1R AK18 MoAb KiH).
Figure 7B:
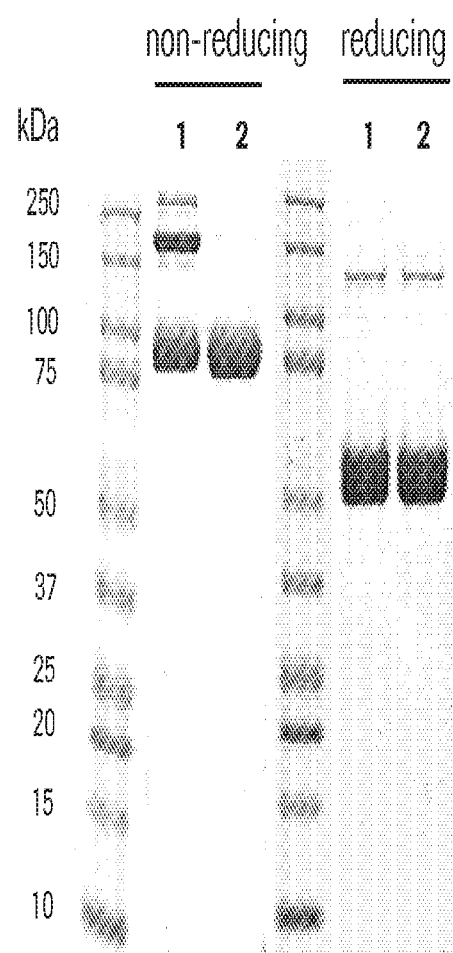

The size of the different peaks was confirmed by SEC-MALLS (FIG. 4C) and the identity of the isolated proteins was confirmed by mass spectrometry. Taken together these data show that the CH1-CL crossover allows the easy purification of a pure monovalent antibody (peak 3 in FIG. 3, peak 2 in FIG. 4, peak 3 in FIG. 5) without the need to include knobs-into-holes into the Fc proportion to enforce heterodimerization. This product can be baseline separated by size exclusion chromatography from a bivalent, dimeric form of the antigen binding protein (MoAb-Dimer) as byproduct as depicted in FIG. 1C that precedes the peak for the monovalent antigen binding protein. Most of the cysteine bridges in the bivalent, dimeric construct which crosslink the dimer are not closed which leads to the observation that under non-reducing conditions in SDS-PAGE a main product is observed at 100 kDa and not as would be expected at 200 kDa (peak 2 in FIG. 3, peak 1 in FIG. 4, peak 2 in FIG. 5). The additional peak (peak 1 in FIG. 3, peak 1 in FIG. 5) observable for c-Met 5D5 MoAb ("wt") and Her3 205 MoAb ("wt") depict higher molecular weight aggregates. This is in contrast to the monovalent antibody as described in WO/2007/048037 where the mixture of heterodimeric and homodimeric monovalent antibody (FIG. 2) cannot be separated by conventional means.

FIG. 6A, 6B, 7A, 7B, 8A, and 8B depict the chromatograms of the size exclusion chromatography of the three different monovalent antigen binding proteins with knobs-into-holes as well as the corresponding SDS-PAGE under non-reducing and reducing conditions.

By applying this knobs-into-holes technology for Fc-heterodimerization the relative yields of heterodimeric monovalent antigen binding protein compared to the bivalent MoAb-Dimer could be enhanced as shown in FIGS. 6A, 6B, 7A, 7B, 8A and 8B.

Example 2 c-Met Phosphorylation (FIG. 9)

c-Met has been described as oncogenic receptor tyrosine kinase which upon deregulation fosters cellular transformation. Antibodies targeting c-Met have been described in the past. MetMAb/OA-5D5 (Genentech) is one such antibody inhibiting ligand-dependent activation of c-Met. As the bivalent antibody is activatory, it was engineered as one-armed construct in which one FAb arm was deleted leaving a monovalent antibody. To demonstrate similar efficacy of OA-5D5 and monovalent antigen binding protein c-Met MoAb (c-Met 5D5 MoAb ("wt")), A549 cells were incubated with the respective antibodies in the absence or presence of HGF, the only known ligand of c-Met. In contrast to the bivalent MetMAb (MetMAb (biv. Ab)), neither of the antibodies has activatory potential in the absence of HGF. Furthermore, as to be expected c-Met MoAb (c-Met 5D5 MoAb ("wt")) is as efficacious in suppressing ligand-induced receptor phosphorylation as OA-5D5. An unspecific human IgG control antibody has no influence on HGF-dependent c-Met receptor phosphorylation.

Example 3

Figure 10:
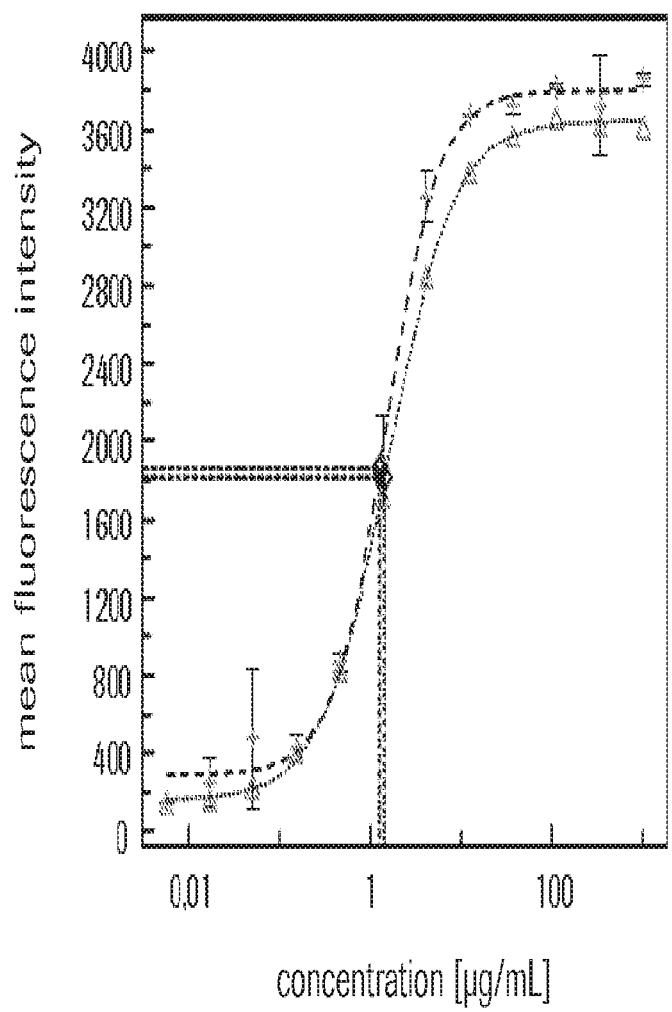
FIG. 10 Cellular binding of MoAb c-Met (c-Met 5D5 MoAb ("wt"))) to A549 cells with flow cytometric analysis. A549 cells were incubated with a dilution series of the indicated antibodies. Bound antibodies were visualized with an Fc-binding secondary fluorophor coupled antibody.

Cellular Binding to c-Met Expressing Cell Lines (FIG. 10)

Cellular binding of monovalent antigen binding protein c-Met MoAb (c-Met 5D5 MoAb ("wt")) was demonstrated on A549 cells. A cell suspension was incubated with a threefold dilution series (100-0.0003 µg/mL) of the indicated antibodies. Bound antibodies were visualized with a secondary Alexa488-coupled antibody binding to the constant region of human immunoglobulin. Fluorescence intensity of single cells was measured on a FACS Canto (BD Biosciences) flow cytometer. No differences in binding of c-Met MoAb and OA-5D5 are observable indicating that the c-Met MoAb (c-Met 5D5 MoAb ("wt")) efficiently binds to cell surface c-Met.

Half-maximal Binding
OA-5D5: 1.45 nM
c-Met MoAb 1.57 nM

Example 4

Figure 11:
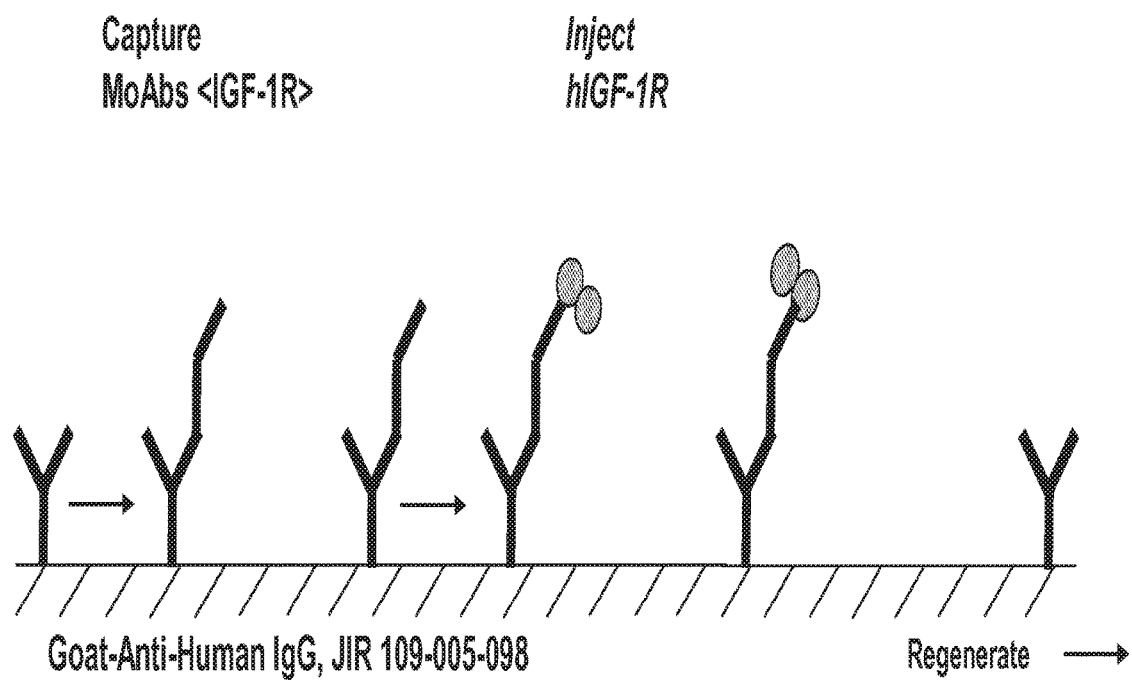
FIG. 11 Schematic picture of the surface plasmon resonance assay applied to analyze the binding affinity of the monovalent antigen binding protein IGF1R AK18 MoAb ("wt").

IGF-1R Binding Affinity (FIG. 11)

IGF-1R extracellular domain binding of the monovalent antigen binding protein IGF1R MoAb (IGF1R AK18 MoAb ("wt")) was compared to the binding of the parental <IGF-1R> IgG1 antibody by surface Plasmon resonance (SPR). FIG. 17 depicts the scheme of the SPR assay to determine the monovalent affinity. The analysis (double determination) showed that the IGF-1R binding affinity is retained in the monovalent antibody.

|  | k(on) | k(off) | KD |
| --- | --- | --- | --- |
| Mab (IGF-1R) | 1.74E+06 | 6.63E−03 | 3.80E−09 |
| MoAb (IGF-1R) | 1.3E+06 | 2.9E−03 | 2.16E−09 |
| MoAb (IGF-1R) | 2.4E+06 | 3.3E−03 | 1.4E−09 |

Example 5

Cellular Binding to IGF-1R Expressing Cell Lines (FIG. 12)

Cellular binding of monovalent antigen binding protein IGF1R MoAb (IGF1R AK18 MoAb ("wt")) was demonstrated on A549 cells. A549 cells in the logarithmic growth phase were detached with accutase (Sigma) and 2×10e5 cells were used for each individual antibody incubation. MoAb was added in a threefold dilution series (100-0.0003 µg/mL). Bound antibodies were visualized with a secondary Alexa488-coupled antibody (5 µg/mL) binding to the constant region of human immunoglobulin. Dead cells were stained with 7-AAD (BD) and excluded from the analysis. Fluorescence intensity of single cells was measured on a FACS Canto (RD Biosciences) flow cytometer. The data show that there is a difference in halfmaximal binding to cells due to the fact that the IGF-1R IgG1 antibody can bind with two arms to IGF-1R on cells and exhibits an avidity effect whereas the monovalent antibody can only bind with one arm.

Half-maximal Binding
IGF-1R (150 kDa): 0.76 nM
IGF-1R MoAb (100 kDa): 5.65 nM

Example 6

Figure 13:
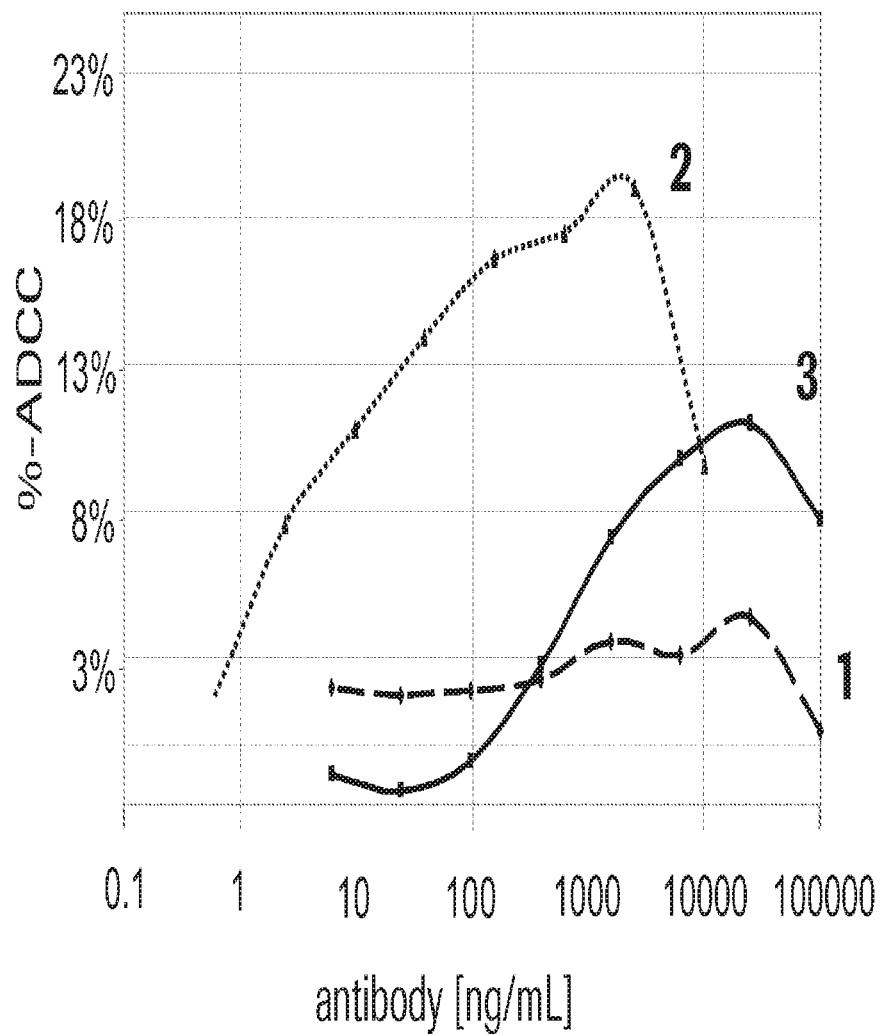
FIG. 13 ADCC Assay with parent non-glycoengineered (non-ge) IGF1R Mab and parent glycoengineered (ge) IGF1R Mab and non-glycoengineered monovalent antigen binding protein IGF1R MoAb (IGF1R AK18 MoAb ("wt")). Donor derived peripheral blood mononuclear cells (PBMC) were incubated with prostate cancer cells (DU145) in the presence of parent non-ge IGF1R Mab (=1), parent ge IGF1R Mab (=2) and non-ge monovalent antigen binding protein IGF1R MoAb (=3).

ADCC Induction (FIG. 13)

Donor-derived peripheral blood mononuclear cells (PBMC) can be used to measure effector cell recruitment by non-glycoengineered and glycoengineered antibodies to cancer cells. Lysis of cancer cells correlates with NK cell mediated cytotoxicity and is proportional to the antibody's ability to recruit NK cells. In this particular setting, DU145 prostate cancer cells were incubated in a 1:25 ratio (DU145: PBMC) ratio with PBMC in the absence or presence of the respective antibodies. After 2 hours cellular lysis was determined using the BATDA/Europium system as described above. The magnitude of cell lysis by ADCC is expressed as % of the maximum release of TDA fluorescence enhancer from the target cells lysed by detergent corrected for spontaneous release of TDA from the respective target cells. The data show that despite the lower apparent affinity for IGF-1R on cells the non-glycoengineered monovalent antigen binding protein IGF1R MoAb (IGF1R AK18 MoAb ("wt")) is superior in inducing ADCC at high concentrations compared to the non-glycoengineered parent IGF-1R antibody. Surprisingly, the non-glycoengineered monovalent antigen binding protein IGF1R MoAb (IGF1R AK18 MoAb ("wt")) is even superior in inducing ADCC at high concentrations compared to the glycoengineered parent IGF-1R antibody that shows a drop in the ADCC assay going to high concentrations. Monovalent IGF-1R antigen binding proteins (IGF1R AK18 MoAb ("wt")) that mediate reduced IGF-1R internalization and enhanced ADCC due to reduced internalization (see below) and double the amount of Fc-parts to engage FcRIIIa receptors on effector cells may thus represent a promising approach to target IGF-1R on cancer cells; as non-glycoengineered or as glycoengineered antibodies.

Example 7

Figure 14:
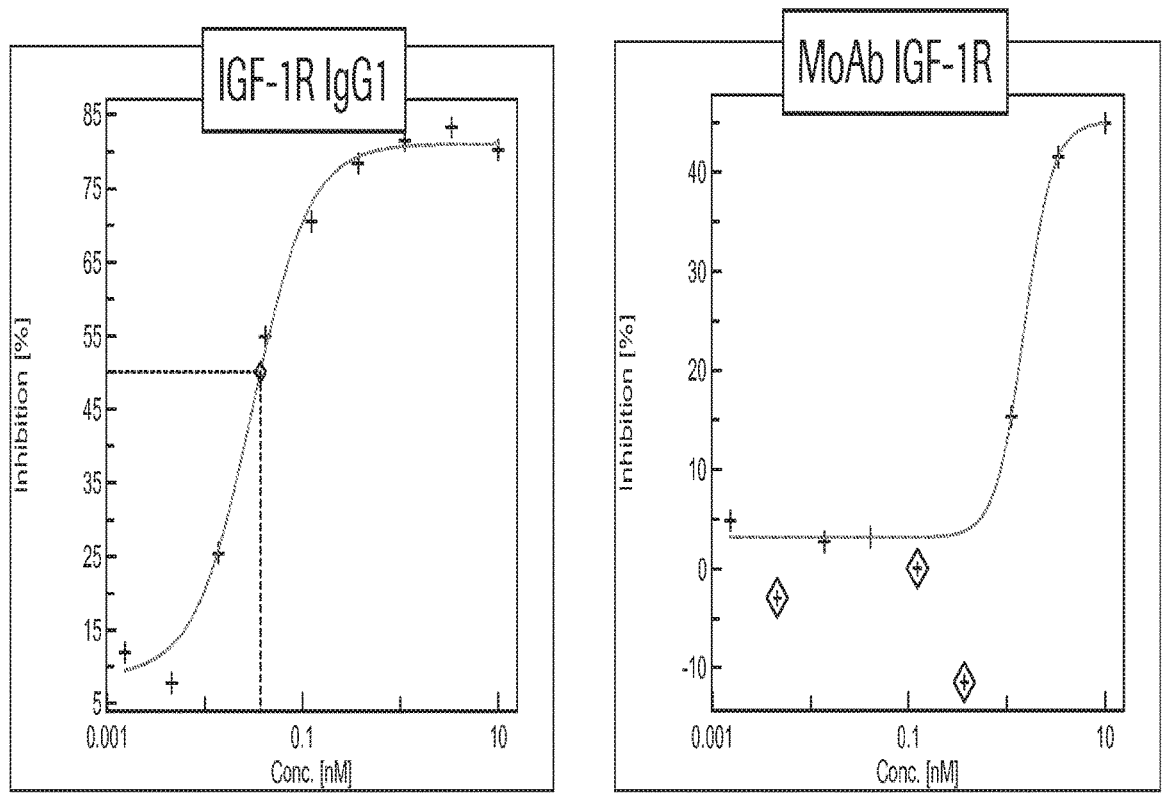
FIG. 14 Internalization of IGF-1R was assessed following incubation with parent IGF-1R IgG1 antibody and monovalent antigen binding protein IGF1R MoAb (IGF1R AK18 MoAb ("wt")), the data show that internalization of IGF-1R is reduced in terms of potency and absolute internalization when the monovalent antigen binding protein IGF1R MoAb (IGF1R AK18 MoAb ("wt")) is bound.

IGF-1R Internalization Assay (FIG. 14)

Targeting IGF-1R by bivalent parent IGF-1R antibodies results in internalization of IGF-1R. We investigated the internalization properties of the monovalent antigen binding protein IGF1R MoAb (IGF1R AK18 MoAb ("wt")). The data in FIG. 14 show that internalization of IGF-1R is reduced in terms of potency and absolute internalization when the monovalent antigen binding protein IGF1R MoAb (IGF1R AK18 MoAb ("wt")) is bound.

The targeting IGF-1R on tumor cells by bivalent IGF-1R antibodies results in internalization and lysosomal degradation of IGF-1R. We investigated the internalization properties of the monovalent antigen binding protein IGF1R MoAb (IGF1R AK18 MoAb ("wt")). For this purpose. HT29 colon cancer cells were treated for 18 hours with different concentrations of monovalent antigen binding protein IGF1R MoAb (IGF1R AK18 MoAb ("wt")) and bivalent parent IGF-1R antibody. After lysis of the cells, the remaining levels of IGF-1R protein were determined by IGF-1R specific ELISA.

The data in FIG. 14 show that internalization of IGF-1R is reduced in terms of potency and absolute internalization when the monovalent antigen binding protein IGF1R MoAb (IGF1R AK18 MoAb ("wt")) is bound. Maximum internalization was reduced from 83% (IgG1) to 48% (MoAb), the concentration required for halfmax inhibition increased from 0.027 nM (IgG1) to 1.5 nM (MoAb).

Example 8

Figure 15:
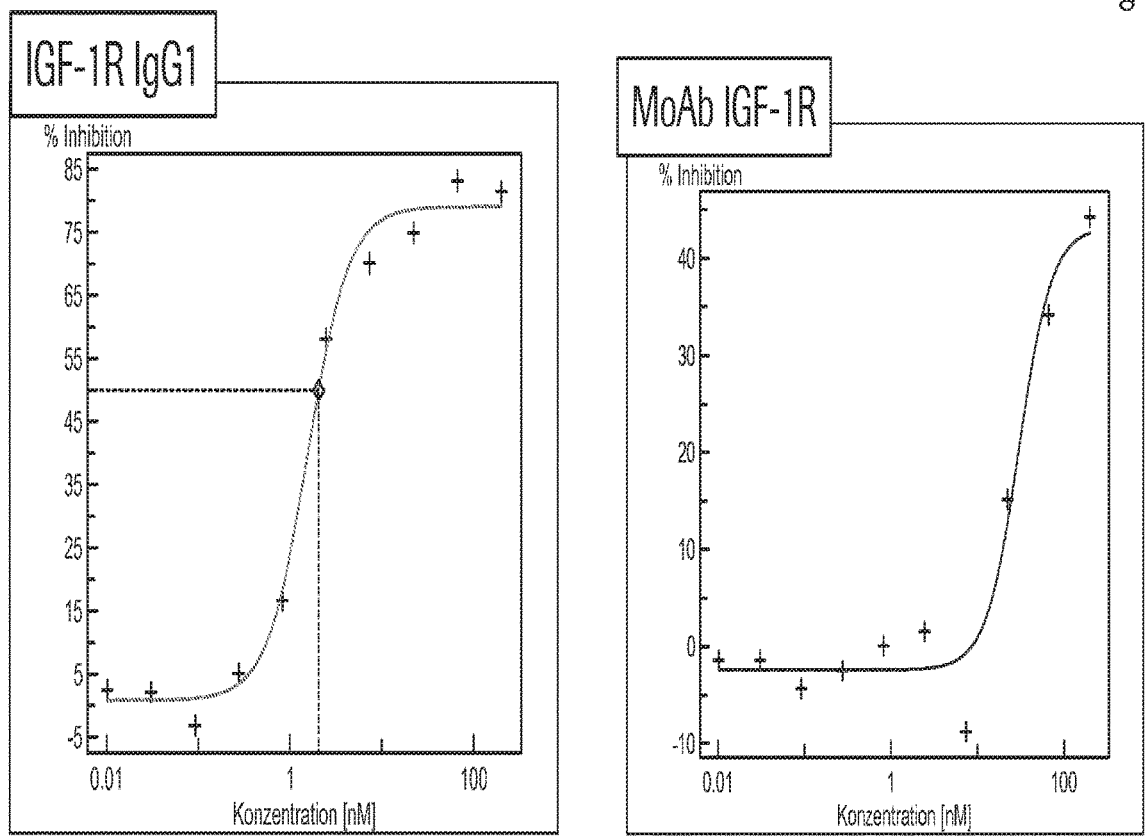
FIG. 15 IGF-1 induced autophosphorylation of IGF-1R was assessed following incubation with IGF-1R IgG1 antibody and monovalent antigen binding protein IGF1R MoAb (IGF1R AK18 MoAb ("wt")), the data show that IGF-1 induced autophosphorylation of IGF-1R is reduced in terms of potency when the monovalent antigen binding protein IGF1R MoAb (IGF1R AK18 MoAb ("wt")) is bound.

IGF-1R Autophosphorylation (IGF-1 Stimulation) (FIG. 15)

Targeting IGF-1R by IGF-1R antibodies results in inhibition of IGF-1 induced autophosphorylation. We investigated the inhibition of autophosphorylation of the monovalent antigen binding protein IGF1R MoAb (IGF1R AK18 MoAb ("wt")) compared to the parent IGF-1R IgG1 antibody. For this purpose 3T3-IGF-1R cells, a murine fibroblast cell line overexpressing human IGF-1R, were treated for 10 minutes with 10 nM recombinant human IGF-1 in the presence of different concentrations of monovalent antigen binding protein IGF1R MoAb (IGF1R AK18 MoAb ("wt")) and bivalent parent IGF-1R antibody. After lysis of the cells, the levels of phosphorylated IGF-1R protein were determined by a phospho-IGF-1R specific ELISA, combining a human IGF-1R specific capture antibody and a phospho-Tyrosine specific detection antibody.

The data in FIG. 15 show that the monovalent antigen binding protein IGF1R MoAb (IGF1R AK18 MoAb ("wt")) can inhibit IGF-1 induced autophosphorylation although at a higher concentration due to monovalent binding on cells (lack of avidity effect due to bivalent binding). The concentration required for halfmax inhibition increased from 1.44 nM (IgG1) to 27.9 nM (MoAb). Since the difference in IC50 values of monovalent and bivalent antibodies is slightly less pronounced in IGF-1R autophosphorylation (19 fold) compared to IGF-1R downregulation (59 fold), the reduced impact of monovalent binding on downregulation cannot solely explained by reduced affinity to the IGF-1R.

Example 9

Figure 16:
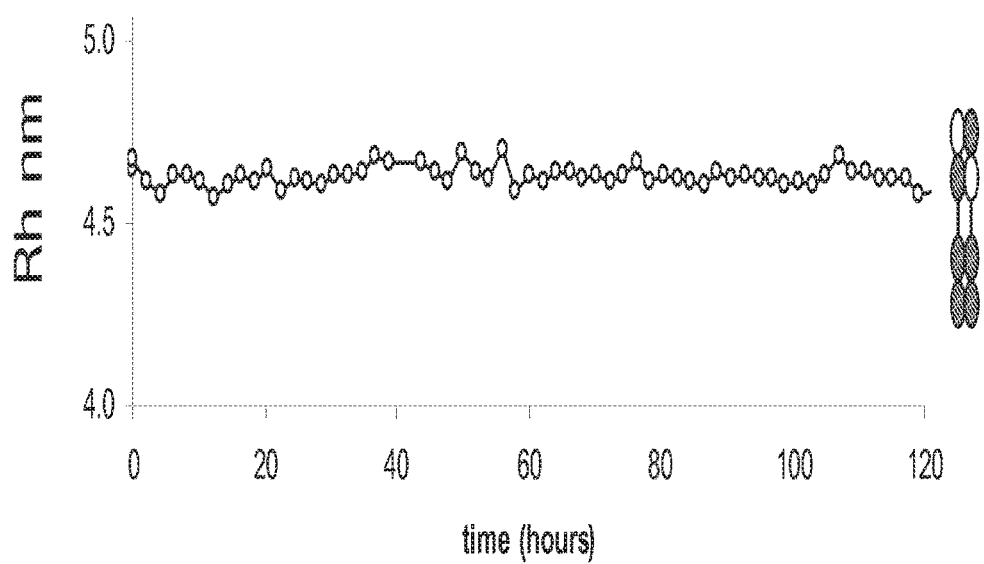
FIG. 16 Aggregation tendency of the monovalent antigen binding protein IGF1R MoAb (IGF1R AK18 MoAb ("wt")) was assessed by a DLS timecourse experiment. Over a period of five days, no measurable increase in the hydrodynamic radius (Rh) of the isolated monomer fraction (see FIGS. 4A-4C) could be detected.

Stability of IGF-1R Monovalent Antigen Binding Protein (FIG. 16)

The stability of the monovalent antigen binding protein IGF1R MoAb (IGF1R AK18 MoAb ("wt")) was studied by dynamic light scattering as described above. Briefly, aggregation tendency of the monovalent antigen binding protein IGF1R MoAb was assessed by a DLS timecourse experiment at 40° C. Over a period of five days, no measurable increase in the hydrodynamic radius (Rh) of the isolated monomer fraction (c.f. FIG. 10) could be detected (FIG. 16).

Example 10

Determination of PK Properties

Pharmacokinetic properties of the monovalent antibodies according to the invention were determined in NMRI mice, female, fed, 23-32 g body weight at the time point of compound administration mice in a single dose PK study, as described above (in the methods sections).

The PK properties are given in the subsequent table and indicate that the monovalent antigen binding protein IGF1R MoAb (IGF1R AK18 MoAb ("wt")) has improved PK properties compared to the parental <IGF-1R> IgG1 antibody.

TABLE 2

Summary of PK properties

|  |  | <IGF-1R> IgG1 antibody | <IGF1R> MoAb |
|---|---|---|---|
| C0 | μg/mL | 81.9 | 298.32 |
| Cmax | μg/mL | 80.7 | 290.2 |
| Tmax | h | 0.5 | 0.5 |
| AUC0-inf | h*μg/mL | 9349 | 20159 |
| term t½ | h | 106.2 | 148.9 |
| Cl | mL/min/kg | 0.018 | 0.0083 |
| Vss | L/kg | 0.16 | 0.082 |

Example 11

Figure 18:
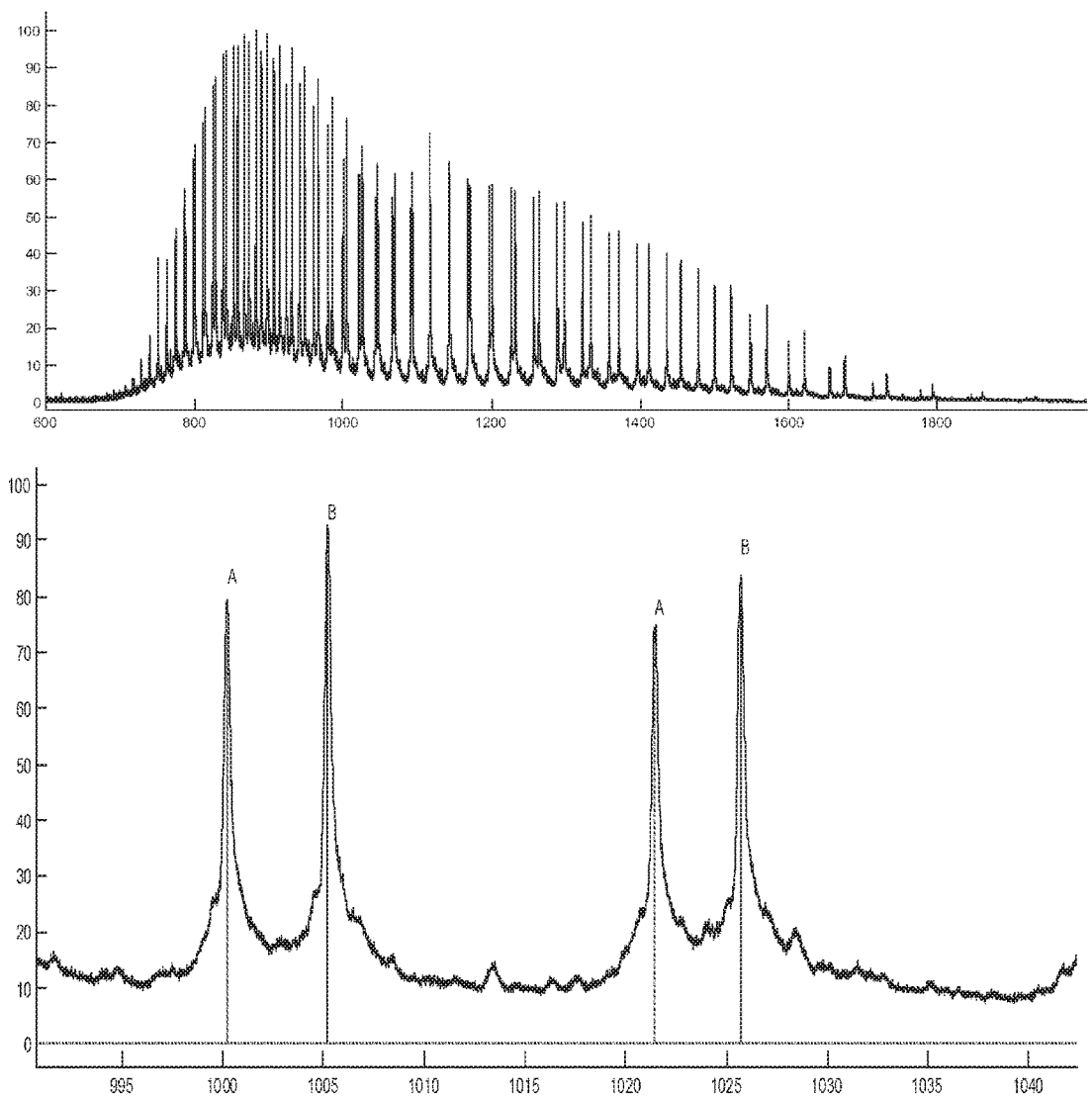
FIG. 18 ESI-MS spectrum of the IGF-1R monovalent antigen binding protein IGF1R MoAb (IGF1R AK18 MoAb ("wt")) after deglycosylation and reduction.

ESI-MS experiment IGF-1R MoAb (FIGS. 17 and 18)

The monovalent antigen binding protein IGF1R MoAb (IGF1R AK18 MoAb ("wt")) was transiently expressed and purified via Protein A affinity and size exclusion chromatography. After preparative SEC the antibody eluted within two separate peaks (peak 1 and peak 2), which were collected. Analytical SEC from the fraction 2 (peak 2) corresponds to a molecular weight of 100 kDa indicating a defined monomer. SEC-MALS confirmed the initial SEC result and shows for the fraction 2 (monomer,) a MW of 99.5 kDa. SDS-PAGE analysis of this fraction under denaturing and reducing conditions shows one major band with an apparent molecular weight of 50-60 kDa. Under non reducing conditions fraction 2 (monomer) shows a major band around a MW of 100 kDa.

Fraction 1=165 mL

Fraction 2=190 mL

ESI-MS spectra of deglycosylated MoAbs from fraction 2 show one peak series corresponding to a monomer with a mass of 98151 Da.

TABLE 3

Summary of MS data from non reducing ESI-MS measurements from fraction 2.

| Fraction | Molecular weight, monomer (theor. 98162 Da) |
|---|---|
| Fraction 2 | 98151 Da |

MS measurements under reducing conditions of fraction 2 show the correct sequence and expression of the construct. The MS data from fraction 2 show two different heavy chains with a molecular weight of 47959 Da and 50211 Da in approximately equal amounts.

TABLE 4

Summary of MS data from reducing ESI-MS measurements under reducing conditions from fraction 2.

| Fraction | Molecular weight, heavy chain 1 (theor. 50226 Da) | Molecular weight, heavy chain 2 (theor. 47961 Da) |
|---|---|---|
| Fraction 2 | 50211 Da (pyro Glu at N-term.) | 47959 Da |

Example 12

Production of Glycoengineered Antigen Binding Proteins

For the production of the glycoengineered antigen binding protein, HEK-EBNA cells are transfected, using the calcium phosphate method, with four plasmids. Two encoding the antibody chains, one for a fusion GnTIII polypeptide expression (a GnT-III expression vector), and one for mannosidase II expression (a Golgi mannosidase II expression vector) at a ratio of 4:4:1:1, respectively. Cells are grown as adherent monolayer cultures in T flasks using DMEM culture medium supplemented with 10% FCS, and are transfected when they are between 50 and 80% confluent. For the transfection of a T150 flask, 15 million cells are seeded 24 hours before transfection in 25 ml DMEM culture medium supplemented with FCS (at 10% V/V final), and cells are placed at 37° C. in an incubator with a 5% $CO_2$ atmosphere overnight. For each T150 flask to be transfected, a solution of DNA, $CaCl_2$ and water is prepared by mixing 94 μg total plasmid vector DNA divided equally between the light and heavy chain expression vectors, water to a final volume of 469 μl and 469 μl of a 1M $CaCl_2$ solution. To this solution, 938 μl of a 50 mM HEPES, 280 mM NaCl, 1.5 mM $Na_2HPO_4$ solution at pH 7.05 are added, mixed immediately for 10 sec and left to stand at room temperature for 20 sec. The suspension is diluted with 10 ml of DMEM supplemented with 2% FCS, and added to the T150 in place of the existing medium. Then additional 13 ml of transfection medium are added. The cells are incubated at 37° C., 5% $CO_2$ for about 17 to 20 hours, then medium is replaced with 25 ml DMEM, 10% FCS. The conditioned culture medium is harvested approx. 7 days post-media exchange by centrifugation for 15 min at 210× g, the solution is sterile filtered (0.22 um filter) and sodium azide in a final concentration of 0.01% w/v is added, and kept at 4° C.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for the preparation of a monovalent antigen binding protein comprising the steps of
    a) transforming a host cell with vectors comprising nucleic acid molecules encoding a monovalent antigen binding protein, wherein the monovalent antigen binding protein comprises
        i) a modified heavy chain of an antibody which specifically binds to an antigen, wherein the VH domain is replaced by the VL domain of said antibody; and
        ii) a modified heavy chain of said antibody, wherein the CH1 domain is replaced by the CL domain of said antibody;
    b) culturing the host cell under conditions that allow synthesis of said monovalent antigen binding protein;
    c) recovering said monovalent antigen binding protein from said culture; and
    d) separating the monovalent antigen binding protein from a high molecular weight tetrameric byproduct by molecular weight separation;
    wherein the preparation is free of detectable homodimers.

2. The method of claim 1, wherein the molecular weight separation is size exclusion chromatography.

3. The method according to claim 1, wherein the monovalent antigen binding protein comprises:
    the modified heavy chain of the antibody of i) comprises a CH3 domain;
    the modified heavy chain of antibody of ii) comprises a CH3 domain; wherein
    the CH3 domain of the modified heavy chain of the antibody of i) and the CH3 domain of the modified heavy chain of the antibody of ii) each meet at an interface which comprises an original interface between the antibody CH3 domains;
    wherein said interface is altered to promote the formation of the monovalent antigen binding protein, wherein:
        a CH3 domain of one heavy chain is altered, so that within the original interface the CH3 domain of one heavy chain that meets the original interface of the CH3 domain of the other heavy chain within the monovalent antigen binding protein, an amino acid residue is replaced with an amino acid residue having a larger side chain volume, thereby generating a protuberance within the interface of the CH3 domain of one heavy chain which is positionable in a cavity within the interface of the CH3 domain of the other heavy chain
    and
    the CH3 domain of the other heavy chain is altered, so that within the original interface of the second CH3 domain that meets the original interface of the first CH3 domain within the monovalent antigen binding protein, an amino acid residue is replaced with an amino acid residue having a smaller side chain volume, thereby generating a cavity within the interface of the second CH3 domain within which a protuberance within the interface of the first CH3 domain is positionable.

4. The method according to claim 3, wherein said amino acid residue having a larger side chain volume is selected from the group consisting of arginine (R), phenylalanine (F), tyrosine (Y), tryptophan (W), and said amino acid residue having a smaller side chain volume is selected from the group consisting of alanine (A), serine (S), threonine (T), valine (V).

5. The method according to claim 4, wherein both CH3 domains are further altered by the introduction of cysteine (C) as amino acid in the corresponding positions of each CH3 domain such that a disulfide bridge between both CH3 domains can be formed.

6. The method according to claim 1, wherein said modified heavy chains of i) and ii) are of human IgG1 isotype.

7. The method according to claim 1, wherein the monovalent antigen binding protein comprises
    i) a modified heavy chain comprising the amino acid sequence of SEQ ID NO: 1; and
    ii) a modified heavy chain comprising the amino acid sequence of SEQ ID NO: 2; or
    i) a modified heavy chain comprising the amino acid sequence of SEQ ID NO: 3; and
    ii) a modified heavy chain comprising the amino acid sequence of SEQ ID NO: 4; or
    i) a modified heavy chain comprising the amino acid sequence of SEQ ID NO: 5; and
    ii) a modified heavy chain comprising the amino acid sequence of SEQ ID NO: 6; or
    i) a modified heavy chain comprising the amino acid sequence of SEQ ID NO: 7; and
    ii) a modified heavy chain comprising the amino acid sequence of SEQ ID NO: 8; or
    i) a modified heavy chain comprising the amino acid sequence of SEQ ID NO: 9; and
    ii) a modified heavy chain comprising the amino acid sequence of SEQ ID NO: 10; or
    i) a modified heavy chain comprising the amino acid sequence of SEQ ID NO: 11; and
    ii) a modified heavy chain comprising the amino acid sequence of SEQ ID NO: 12.

8. The method of claim 1, wherein the modified heavy chains of the monovalent antigen binding protein of i) and ii) are of IgG1 isotype, and the antigen binding protein is a fucosylated with an amount of fucose of 80% or less of the total amount of oligosaccharides at Asn297, wherein amino acid position 297 is numbered according to the EU Index of Kabat.

* * * * *